United States Patent
Kim

(10) Patent No.: US 10,036,013 B2
(45) Date of Patent: Jul. 31, 2018

(54) NEXT-GENERATION SEQUENCING LIBRARIES

(71) Applicant: ABBOTT MOLECULAR INC., Des Plaines, IL (US)

(72) Inventor: Dae Hyun Kim, Northbrook, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 705 days.

(21) Appl. No.: 14/463,498

(22) Filed: Aug. 19, 2014

(65) Prior Publication Data

US 2015/0051116 A1 Feb. 19, 2015

Related U.S. Application Data

(60) Provisional application No. 61/867,224, filed on Aug. 19, 2013.

(51) Int. Cl.
*C12N 15/10* (2006.01)
*C12Q 1/68* (2018.01)
*C40B 50/06* (2006.01)
*C12Q 1/6806* (2018.01)

(52) U.S. Cl.
CPC ....... *C12N 15/1086* (2013.01); *C12Q 1/6806* (2013.01); *C40B 50/06* (2013.01)

(58) Field of Classification Search
None
See application file for complete search history.

(56) References Cited

U.S. PATENT DOCUMENTS

| | | |
|---|---|---|
| 4,988,617 A | 1/1991 | Landegren et al. |
| 5,242,794 A | 9/1993 | Whiteley et al. |
| 5,494,810 A | 2/1996 | Barany et al. |
| 5,604,097 A | 2/1997 | Brenner |
| 5,636,400 A | 6/1997 | Young |
| 5,695,934 A | 12/1997 | Brenner |
| 5,846,719 A | 12/1998 | Brenner et al. |
| 5,863,722 A | 1/1999 | Brenner |
| 5,912,148 A | 6/1999 | Eggerding |
| 6,130,073 A | 10/2000 | Eggerding |

(Continued)

FOREIGN PATENT DOCUMENTS

| | | |
|---|---|---|
| WO | WO-9902726 A1 | 1/1999 |
| WO | WO-9949403 A1 | 9/1999 |

(Continued)

OTHER PUBLICATIONS

El-Sagheer A.H., et al., "Biocompatible Artificial DNA Linker that is Read through by DNA Polymerases and is Functional in *Escherichia coli*," Proceedings of the National Academy of Sciences of the United States of America, 2011, vol. 108 (28), pp. 11338-11343.

(Continued)

*Primary Examiner* — Kaijiang Zhang
(74) *Attorney, Agent, or Firm* — Casimir Jones S.C.; David Casimir; Thomas Isenbarger

(57) ABSTRACT

Provided herein is technology relating to next-generation sequencing and particularly, but not exclusively, to methods and compositions for preparing a next-generation sequencing library comprising short overlapping DNA fragments and using the library to sequence one or more target nucleic acids.

11 Claims, 22 Drawing Sheets

(56) References Cited

U.S. PATENT DOCUMENTS

| | | |
|---|---|---|
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,210,891 B1 | 4/2001 | Nyren et al. |
| 6,235,475 B1 | 5/2001 | Brenner et al. |
| 6,258,568 B1 | 7/2001 | Nyren |
| 6,329,178 B1 | 12/2001 | Patel et al. |
| 6,352,828 B1 | 3/2002 | Brenner |
| 6,395,524 B2 | 5/2002 | Loeb et al. |
| 6,582,938 B1 | 6/2003 | Su et al. |
| 6,602,695 B2 | 8/2003 | Patel et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| RE39,793 E | 8/2007 | Brenner |
| 7,282,337 B1 | 10/2007 | Harris |
| 7,302,146 B2 | 11/2007 | Turner et al. |
| 7,313,308 B2 | 12/2007 | Turner et al. |
| 7,315,019 B2 | 1/2008 | Turner et al. |
| 7,329,492 B2 | 2/2008 | Hardin et al. |
| 7,393,665 B2 | 7/2008 | Brenner |
| 7,405,281 B2 | 7/2008 | Xu et al. |
| 7,476,503 B2 | 1/2009 | Turner et al. |
| 7,482,120 B2 | 1/2009 | Buzby et al. |
| 7,501,245 B2 | 3/2009 | Quake et al. |
| 7,537,897 B2 | 5/2009 | Brenner et al. |
| 7,544,473 B2 | 6/2009 | Brenner |
| 7,668,697 B2 | 2/2010 | Volkov et al. |
| 2004/0259118 A1 | 12/2004 | Macevicz |
| 2007/0036511 A1 | 2/2007 | Lundquist et al. |
| 2007/0048748 A1 | 3/2007 | Williams et al. |
| 2007/0072196 A1 | 3/2007 | Xu et al. |
| 2007/0077564 A1 | 4/2007 | Roitman et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0081330 A1 | 4/2008 | Kahvejian |
| 2008/0090738 A1 | 4/2008 | Kwan et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2008/0242560 A1* | 10/2008 | Gunderson et al. . B01J 19/0046 506/26 |
| 2009/0026082 A1 | 1/2009 | Rothberg et al. |
| 2009/0035777 A1 | 2/2009 | Kokoris et al. |
| 2009/0047680 A1 | 2/2009 | Lok |
| 2009/0127589 A1 | 5/2009 | Rothberg et al. |
| 2010/0035253 A1 | 2/2010 | Gordon et al. |
| 2010/0063743 A1 | 3/2010 | Gordon et al. |
| 2010/0137143 A1 | 6/2010 | Rothberg et al. |
| 2010/0145037 A1 | 6/2010 | Makarov et al. |
| 2010/0152050 A1 | 6/2010 | Gordon et al. |
| 2010/0159531 A1 | 6/2010 | Gordon et al. |
| 2010/0188073 A1 | 7/2010 | Rothberg et al. |
| 2010/0197507 A1 | 8/2010 | Rothberg et al. |
| 2010/0204050 A1 | 8/2010 | Donner et al. |
| 2010/0301398 A1 | 12/2010 | Rothberg et al. |
| 2010/0323350 A1 | 12/2010 | Gordon et al. |
| 2011/0104763 A1 | 5/2011 | Gardner et al. |
| 2011/0257889 A1 | 10/2011 | Klammer et al. |
| 2011/0270533 A1 | 11/2011 | Zhang et al. |
| 2012/0156753 A1 | 6/2012 | Jendrisak et al. |
| 2012/0165202 A1 | 6/2012 | Porreca et al. |
| 2013/0143774 A1 | 6/2013 | Actis et al. |
| 2013/0303461 A1 | 11/2013 | Iafrate et al. |
| 2015/0050697 A1 | 2/2015 | Kim |
| 2015/0051113 A1 | 2/2015 | Kim |

FOREIGN PATENT DOCUMENTS

| | | |
|---|---|---|
| WO | 02/061428 | 8/2002 |
| WO | WO-2007084433 A2 | 7/2007 |
| WO | WO-2010056728 A1 | 5/2010 |
| WO | 2012/06116 | 1/2012 |
| WO | WO-2014110006 A1 | 7/2014 |
| WO | WO-2014150851 A1 | 9/2014 |
| WO | WO-2015026845 A2 | 2/2015 |

OTHER PUBLICATIONS

International Search Report for Application No. PCT/US2014/51739, dated Feb. 9, 2015, 6 pages.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Kent W.J., et al, "Assembly of the Working Draft of the Human Genome with Gigassembler." Genome research, 2001, vol. 11 (9), pp. 1541-1548.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

Loman N.J., et al., "Performance Comparison of Benchtop High-Throughput Sequencing Platforms," Nature Biotechnology, 2012, vol. 30 (5), pp. 434-439.

Lundin S., et al., "Hierarchical Molecular Tagging to Resolve Long Continuous Sequences by Massively Parallel Sequencing," Scientific Reports, 2013, vol. 3, p. 1186.

Maclean D., et al., "Application of 'next-generation' Sequencing Technologies to Microbial Genetics," Nature Reviews Microbiology, 2009, vol. 7 (4), pp. 287-296.

Maniatis T., et al., Molecular Cloning: A Laboratory manual, Cold Spring Harbor Laboratory, New York, 1982, pp. 280-281.

Margulies M., et al., "Genome Sequencing in Microfabricated High-Density Picolitre Reactors," Nature, 2005, vol. 437 (7057), pp. 376-380.

Motahari A., et al., "Optimal DNA Shotgun Sequencing: Noisy Reads are as good as Noiseless Reads," IEEE International Symposium on Information Theory, Apr. 9, 2013, DOI: 10.1109/ISIT.2013.6620505.

Moudrianakis E.N., et al., "Base Sequence Determination in Nucleic Acids with the Electron Microscope, III. Chemistry and Microscopy of Guanine-Labeled DNA," Proceedings of the National Academy of Science, 1965, vol. 53 (3), pp. 564-571.

Mullikin J.C., et al., "The Phusion Assembler," Genome Research, 2003, vol. 13 (1), pp. 81-90.

(56) References Cited

OTHER PUBLICATIONS

Parameswaran P., et al., "A Pyrosequencing-Tailored Nucleotide Barcode Design Unveils Opportunities for Large-Scale Sample Multiplexing," Nucleic Acids Research, 2007, vol. 35 (19), p. E130.
Pennisi E., "Genomics. Semiconductors Inspire New Sequencing Technologies," Science, 2010, vol. 327 (5970), pp. 1190.
Roach J.C., et al., "Pairwise End Sequencing: a Unified Approach to Genomic Mapping and Sequencing," Genomics, 1995, vol. 26 (2), pp. 345-353.
Sanger F., et al., "A Rapid Method for Determining Sequences in DNA by Primed Synthesis with DNA Polymerase," Journal of Molecular Biology, 1975, vol. 94 (3), pp. 441-446.
Sanger F., et al., "DNA Sequencing with Chain-Terminating Inhibitors," Proceedings of the National Academy of Sciences, 1977, vol. 74 (12), pp. 5463-5467.
Siegel A.F., et al., "Modeling the Feasibility of Whole Genome Shotgun Sequencing Using a Pairwise End Strategy," Genomics, 2000, vol. 68 (3), pp. 237-246.
Soni G.V., et al., "Progress toward Ultrafast DNA Sequencing Using Solid-State Nanopores," Clinical Chemistry, 2007, vol. 53 (11), pp. 1996-2001.
Voelkerding K.V., et al., "Next-Generation Sequencing: from Basic Research to Diagnostics," Clinical Chemistry, 2009, vol. 55 (4), pp. 641-658.
Zagordi D., et al., "Error Correction of Next-Generation Sequencing Data and Reliable Estimation of HIV Quasispecies," Nucleic Acids Research, 2010, doi: 10.1093/nar/gkq655 First published online: Jul. 29, 2010, pp. 1-10.
Office action issued in corresponding Chinese Patent Application No. 201480057285.0, dated Apr. 5, 2017.
Extended European Search Report issued in corresponding European Patent Application No. 14837282.4, dated May 19, 2017.
Partial Supplementary European Search Report issued in corresponding European Patent Application No. 14837282.4, dated Feb. 10, 2017.

\* cited by examiner

FIG. 4E

SEQ ID NO: 32
SEQ ID NO: 33
SEQ ID NO: 35
SEQ ID NO: 36
SEQ ID NO: 38

FIG. 4G

Illumina MiSeq Run
- 35bp reads
- 127bp consensus read
- Sequence run time = 2.5 hr
- (~13 hrs for 127 cycles)

NO: 34

ID NO: 37

—SEQ ID NO: 39

FIG. 4H

SEQ ID NO: 40

SEQ ID NO: 42

SEQ ID NO: 41

SEQ ID NO: 43

FIG. 4J

NEXT-GENERATION SEQUENCING LIBRARIES

This application claims priority to U.S. provisional patent application Ser. No. 61/867,224, filed Aug. 19, 2013, which is incorporated herein by reference in its entirety.

FIELD OF INVENTION

Provided herein is technology relating to next-generation sequencing and particularly, but not exclusively, to methods, compositions, kits, and systems for preparing a next-generation sequencing library comprising overlapping DNA fragments and using the library to sequence one or more target nucleic acids.

BACKGROUND

Nucleic acid sequences encode the necessary information for living things to function and reproduce. Determining such sequences is therefore a tool useful in pure research into how and where organisms live, as well as in applied sciences such as drug development. In medicine, sequencing tools are used for diagnosis and to develop treatments for a variety of pathologies, including cancer, infectious disease, heart disease, autoimmune disorders, multiple sclerosis, and obesity. In industry, sequencing is used to design improved enzymatic processes and synthetic organisms. In biology, such tools are used to study the health of ecosystems, for example, and thus have a broad range of utility.

One focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible for sequencing. These goals can be reached through using sequencing platforms and methods that provide sample preparation for larger quantities of samples of significant complexity, sequencing larger numbers of complex samples, and/or providing a high volume of information generation and analysis in a short period of time. Various methods, such as, for example, sequencing by synthesis, sequencing by hybridization, and sequencing by ligation are evolving to meet these challenges.

Many next-generation sequencing (NGS) platforms are available for the high-throughput, massively parallel sequencing of nucleic acids. Many of these systems, such as the HiSeq and MiSeq systems produced by Illumina, use a sequencing-by-synthesis (SBS) approach, wherein a nucleotide sequence is determined using base-by-base detection and identification. Using this particular approach, identifying 1 base requires 1 cycle of the SBS chemistry process (which may involve four separate reactions separated by washes).

Currently, these technologies provide a maximum achievable read length of ~250 bases, which can be extended to ~400 (2×250 bases with sufficient overlap for assembly) if two high-quality paired-end reads are acquired from the same template and assembled. Each SBS cycle takes approximately 4 minutes to complete; thus, in a paired-end approach to acquire ~400 bases of sequence information, the 500 cycles of SBS required to produce the two reads of ~250 bases takes approximately 37 hours to complete. In addition, most of the cyclic sequencing technologies' performance and quality substantially decrease after determining ~100 bases, introducing a degree of uncertainty associated with individual sequence reads longer than ~100 bases and the longer sequence assemblies in which they are used. Due to these quality and time limitations of current NGS platforms, the ever-increasing demands for long, high-quality nucleotide sequences are saturating the output capabilities of the installed base of sequencing apparatuses. Consequently, technologies are needed that provide high-quality sequences of ~500 bases or more from a much shorter sequencing run-time of several hours rather than several days.

SUMMARY

Some attempts to acquire longer sequences by NGS technology have applied the approach of assembling multiple short reads to produce a longer sequence. For example, the Moleculo technology provided by Illumina initially isolates a single copy of a long (~10 Kbp) DNA fragment. This long DNA fragment is clonally amplified and subsequently fragmented into smaller pieces of approximately 300-800 bases. Finally, adaptors with barcodes are appended to the smaller pieces using a transposase to generate the sequencing library. A standard SBS protocol is used to acquire ~300-500 bases of sequence from the target template (2×150 bases or 2×250 bases) and, once the sequences are generated, the barcodes are used to parse and assemble the reads to provide the sequence of the original ~10 Kbp DNA. Another method involves creation of an overlapping fragment library suitable for an Illumina sequencer, which produces reads ranging from ~400-460 bases by assembling two ~250-base reads that overlap by ~20-50 bases (see, e.g., Lundin, et al. (2012) *Scientific Reports* 3: 1186). This overlapping library is constructed mainly by tagging fragments with specific adaptor sequences, followed by a digestion step and a precise size selection process.

Accordingly, provided herein is a technology for sequencing that utilizes a relatively short read length (e.g., less than 300 or less than 200 bases, e.g., ~30-50 bases) to achieve a high-quality, long contiguous sequence comparable or superior to conventional technologies. In contrast to conventional technologies, the technology provided requires only a short period of run-time (e.g., ~3-4 hours) on a sequencer (e.g., Illumina MiSeq platform), thus dramatically decreasing the time dedicated to use of the sequencing apparatus required to complete a sequencing run. Moreover, the technology results in longer sequences (e.g., ~500 bp to 1000 bp or more of high quality sequence) than conventional technology. Also, run-time does not increase as a function of the size of the nucleic acid to be sequenced because the short read size (e.g., ~30-50) remains the same regardless of the size of the nucleic acid to be sequenced.

The technology is not limited to any particular sequencing platform, but is generally applicable and platform independent. For example, in addition to decreases in run-time on Illumina systems, similar time reductions are achieved for sequences acquired using, e.g., Life Technologies Ion Torrent and Qiagen GeneReader systems. In particular, while acquiring a ~400 base sequence using conventional Ion Torrent sample preparation and sequencing technology requires approximately 4 hours, the technology provided herein reduces that time to approximately 20 to 30 minutes. In some embodiments, the technology is applicable to emulsion PCR-based methods, bead-based, and non-based methods, and thus finds use in the Life Technologies SOLiD systems and the Qiagen NGS sequencing platforms.

This technology provides high quality sequence in a decreased sequencing time relative to conventional technologies. The technology is platform agnostic and thus is compatible with extant sequencing apparatuses. The technology, in some embodiments, enhances existing NGS platforms by, e.g., increasing the read length of extant platforms and shortening the time to sequence acquisition. Furthermore, an added advantage of the present technology is that it reduces consumption of expensive sequencing reagents and thus can decrease the overall per-base cost of sequencing.

In short, the technology involves producing a set of defined overlapping short sequence library inserts (e.g., less than 300 or less than 200 bases, e.g., ~30-50 bases) tiled over a region of a nucleic acid to be sequenced and offset from one another by, e.g., 1-20, 1-10, or 1-5 bases (e.g., in some embodiments, by 1 base). After producing the set of sequences using the overlapping libraries, bioinformatic assembly algorithms are used to "stitch" the tiled set of short overlapping sequences together to produce the sequence of the nucleic acid.

First, sequence quality is high because each base in the nucleic acid to be sequenced is sequenced with high coverage (e.g., 10-fold to 1000-fold coverage, e.g., 50-fold to 500-fold coverage) depending on the length of the short sequences acquired and the offset between adjacent tiled sequences. The high sampling rate at each base minimizes or eliminates sequencing errors by providing increased information to the assembly process that determines the consensus identity of each base. In addition, the first bases (e.g., the first ~20-100 bases) determined in a sequencing run generally have the best quality. Thus, by using these initial bases determined during the first part of each sequencing run (e.g., the first ~30-50 bases), high quality sequence information is used in the assembly. The technology thus minimizes sequencing errors, especially in applications where long sequence reads are desired that retain phasing and linkage information associated with the reads and assemblies.

Second, sequencer time is reduced because determining each short sequence (e.g., ~30-50 bases) requires only a small number of sequencing cycles (e.g., 1 cycle per base, e.g., ~30-50 cycles) on the sequencing apparatus. By determining all the short sequences in the set of short sequences in parallel, the sequencing time needed to provide the sequence of the nucleic acid to be sequenced is greatly reduced, e.g., to one-eighth to one-tenth of the time needed by conventional technologies to sequence the same nucleic acid to be sequenced.

This technology for NGS library preparation and sequencing and the subsequent short-read parsing and assembly provides acquisition of more than ~500 bp (e.g., 600, 700, 800 bp or more) of high-quality contiguous sequence with phase information. The technology finds use, e.g., in sequencing unknown regions starting from a known region, for example, to interrogate structural variants such as gene translocations, e.g., the detection and identification of unknown gene fusion partners. Moreover, the technology enhances existing NGS platforms' sequencing capabilities relative to read length, run time, and cost without any upgrades and/or changes to existing installed hardware and extant sequencing chemistries.

In some embodiments, the technology is related to a method for determining a target nucleotide sequence, the method comprising determining a first nucleotide subsequence of the target nucleotide sequence, said first nucleotide subsequence having a 5' end at nucleotide $x1$ of the target nucleotide sequence and having a 3' end at nucleotide $y1$ of the target nucleotide sequence; determining a second nucleotide subsequence of the target nucleotide sequence, said second nucleotide subsequence having a 5' end at nucleotide $x2$ of the target nucleotide sequence and having a 3' end at nucleotide $y2$ of the target nucleotide sequence; assembling the first nucleotide subsequence and the second nucleotide subsequence to provide a consensus sequence for the target nucleotide sequence, wherein $x2<y1$; and $(y1-x1)<100$, $(y2-x2)<100$, and $(y2-y1)<5$. In some embodiments, the fragments are less than 100 bp, less than 90 bp, less than 80 bp, less than 70 bp, less than 60 bp, less than 55 bp, less than 50 bp, less than 45 bp, less than 40 bp, or less than 35 bp. Accordingly, in some embodiments, $(y1-x1)<100$, 90, 80, 70, 60, 55, 50, 45, 40, or 35 and $(y2-x2)<100$, 90, 80, 70, 60, 55, 50, 45, 40, or 35. In some embodiments, the fragments are less than 50 bp; accordingly, in some embodiments, $(y1-x1)<50$ and $(y2-x2)<50$.

In some embodiments, the 3' ends of the fragments differ with respect to the target sequence by less than 4 or less than 3 bases; accordingly, in some embodiments, $(y2-y1)<4$ or $(y2-y1)<3$. In some embodiments, the 3' ends of the fragments differ with respect to the target sequence by 1 base; accordingly, in some embodiments $(y2-y1)=1$.

In some embodiments, a unique index (a "marker" in some embodiments) is used to associate a fragment with the template nucleic acid from which it was produced. In some embodiments, a unique index is a unique sequence of synthetic nucleotides or a unique sequence of natural nucleotides that allows for easy identification of the target nucleic acid within a complicated collection of oligonucleotides (e.g., fragments) containing various sequences. In certain embodiments, unique index identifiers are attached to nucleic acid fragments prior to attaching adaptor sequences. In some embodiments, unique index identifiers are contained within adaptor sequences such that the unique sequence is contained in the sequencing reads. This ensures that homologous fragments can be detected based upon the unique indices that are attached to each fragment, thus further providing for unambiguous reconstruction of a consensus sequence. Homologous fragments may occur for example by chance due to genomic repeats, two fragments originating from homologous chromosomes, or fragments originating from overlapping locations on the same chromosome. Homologous fragments may also arise from closely related sequences (e.g., closely related gene family members, paralogs, orthologs, ohnologs, xenologs, and/or pseudogenes). Such fragments may be discarded to ensure that long fragment assembly can be computed unambiguously. The markers may be attached as described above for the adaptor sequences. The indices (e.g., markers) may be included in the adaptor sequences.

In some embodiments, the unique index (e.g., index identifier, tag, marker, etc.) is a "barcode". As used herein, the term "barcode" refers to a known nucleic acid sequence that allows some feature of a nucleic acid with which the barcode is associated to be identified. In some embodiments, the feature of the nucleic acid to be identified is the sample or source from which the nucleic acid is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some nucleic acids are of a different length than barcodes associated with other nucleic acids. In general, barcodes are of sufficient length and comprise sequences that are sufficiently different to allow the identification of samples based on barcodes with which they are associated. In some embodiments, a barcode and the sample source with which it is associated can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differs from every other barcode in the plurality at two or more nucleotide positions, such as at 2, 3, 4, 5, 6, 7, 8, 9, 10, or more positions. In some embodiments, one or more adaptors comprise(s) at least one of a plurality of barcode sequences. In some embodiments, methods of the technology further comprise identifying the sample or source from which a target nucleic acid is derived based on a barcode sequence to which the target nucleic acid is joined. In some embodiments, methods of the technology further comprise identifying the target nucleic acid based on a barcode sequence to which the target nucleic acid is joined. Some embodiments of the method further comprise identifying a source or sample of the target nucleotide sequence by determining a barcode nucleotide sequence. Some embodiments of the method further comprise molecular counting applications (e.g., digital barcode enumeration and/or binning) to determine expression levels or copy number status of desired targets. In general, a barcode may comprise a nucleic acid sequence that when joined to a target nucleic acid serves as an identifier of the sample from which the target polynucleotide was derived.

In some embodiments, the methods provide a sequence of up to 100 bases or, in some embodiments, a sequence of more than 100, 200, 300, 400, 500, 600, 700, 800, 900, 1000, or more bases. In some embodiments, the technology provides a sequence of more than 1000 bases, e.g., more than 2000, 2500, 3000, 3500, 4000, 4500, or 5000 or more bases. In some embodiments the consensus sequence comprises up to 100 bases or more, e.g., 200, 300, 400, 500, 600, 700, 800, 900, 1000, or more bases; in some embodiments the consensus sequence comprises more than 1000 bases, e.g., more than 2000, 2500, 3000, 3500, 4000, 4500, or 5000 or more bases.

In some embodiments, an oligonucleotide such as a primer, adaptor, etc. comprises a "universal" sequence. A universal sequence is a known sequence, e.g., for use as a primer or probe binding site using a primer or probe of a known sequence (e.g., complementary to the universal sequence). While a template-specific sequence of a primer, a barcode sequence of a primer, and/or a barcode sequence of an adaptor might differ in embodiments of the technology, e.g., from fragment to fragment, from sample to sample, from source to source, or from region of interest to region of interest, embodiments of the technology provide that a universal sequence is the same from fragment to fragment, from sample to sample, from source to source, or from region of interest to region of interest so that all fragments comprising the universal sequence can be handled and/or treated in a same or similar manner, e.g., amplified, identified, sequenced, isolated, etc., using similar methods or techniques (e.g., using the same primer or probe).

In particular embodiments, a primer is used comprising a universal sequence (e.g., universal sequence A), a barcode sequence, and a template-specific sequence. In particular embodiments, a first adaptor comprising a universal sequence (e.g., universal sequence B) is used and in particular embodiments, a second adaptor comprising a universal sequence (e.g., universal sequence C) is used. Universal sequence A, universal sequence B, and universal sequence C can be any sequence. This nomenclature is used to note that the universal sequence A of a first nucleic acid (e.g., a fragment) comprising universal sequence A is the same as the universal sequence A of a second nucleic acid (e.g., a fragment) comprising universal sequence A, the universal sequence B of a first nucleic acid (e.g., a fragment) comprising universal sequence B is the same as the universal sequence B of a second nucleic acid (e.g., a fragment) comprising universal sequence B, and the universal sequence C of a first nucleic acid (e.g., a fragment) comprising universal sequence C is the same as the universal sequence C of a second nucleic acid (e.g., a fragment) comprising universal sequence C. While universal sequences A, B, and C are generally different in embodiments of the technology, they need not be. Thus, in some embodiments, universal sequences A and B are the same; in some embodiments, universal sequences B and C are the same; in some embodiments, universal sequences A and C are the same; and in some embodiments, universal sequences A, B, and C are the same. In some embodiments, universal sequences A, B, and C are different.

For example, if two regions of interest are to be sequenced (e.g., from the same or different sources or, e.g., from two different regions of the same nucleic acid, chromosome, gene, etc.), two primers may be used, one primer comprising a first template-specific sequence for priming from the first region of interest and a first barcode to associate the first amplified product with the first region of interest and a second primer comprising a second template-specific sequence for priming from the second region of interest and a second barcode to associate the second amplified product with the second region of interest. These two primers, however, in some embodiments, will comprise the same universal sequence (e.g., universal sequence A) for pooling and downstream processing together. Two or more universal sequences may be used and, in general, the number of universal sequences will be less than the number of target-specific sequences and/or barcode sequences for pooling of samples and treatment of pools as a single sample (batch).

Accordingly, in some embodiments, determining the first nucleotide subsequence and the second nucleotide subsequence comprises priming from a universal sequence. In some embodiments determining the first nucleotide subsequence and the second nucleotide subsequence comprises terminating polymerization with a 3'-O-blocked nucleotide analog. For example, in some embodiments determining the first nucleotide subsequence and the second nucleotide subsequence comprises terminating polymerization with a 3'-O-alkynyl nucleotide analog, e.g., in some embodiments determining the first nucleotide subsequence and the second nucleotide subsequence comprises terminating polymerization with a 3'-O-propargyl nucleotide analog. In some embodiments determining the first nucleotide subsequence and the second nucleotide subsequence comprises terminating polymerization with a nucleotide analog comprising a reversible terminator.

The obtained short sequence reads are partitioned according to their barcode (e.g., de-multiplexed) and reads originating from the same samples, sources, regions of interest, etc. are binned together, e.g., saved to separate files or held in an organized data structure that allows binned reads to be identified as such. Then the binned short sequences are assembled into a consensus sequence. Sequence assembly can generally be divided into two broad categories: de novo assembly and reference genome mapping assembly. In de novo assembly, sequence reads are assembled together so that they form a new and previously unknown sequence. In reference genome mapping, sequence reads are assembled against an existing backbone sequence (e.g., a reference sequence, etc.) to build a sequence that is similar but not necessarily identical to the backbone sequence.

Thus, in some embodiments, target nucleic acids corresponding to each region of interest are reconstructed using a de-novo assembly. To begin the reconstruction process, short reads are stitched together bioinformatically by finding overlaps and extending them to produce a consensus sequence. In some embodiments the method further comprises mapping the consensus sequence to a reference sequence. Methods of the technology take advantage of sequencing quality scores that represent base calling confidence to reconstruct full length fragments. In addition to de-novo assembly, fragments can be used to obtain phasing (assignment to homologous copies of chromosomes) of genomic variants by observing that consensus sequences originate from either one of the chromosomes.

In some embodiments, a computer system is implemented for assembly and bioinformatic treatment of sequence information (e.g., identifying barcodes, partitioning, binning, making base calls, determining a consensus identity of each base, stitching reads, assessing quality scores, aligning reads and/or consensus sequences to a reference sequence, etc.). In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. The memory also can be used for storing temporary variables or other intermediate information during execution of instructions to be executed by the processor. In various embodiments, the computer system further includes a read only memory (ROM) or other static storage device coupled to the bus for storing static information and instructions for the processor. In some embodiments, a storage device, such as a solid state drive (e.g., "flash" memory), a magnetic disk, or an optical disk, is provided and coupled to the bus for storing information and instructions.

In various embodiments, the computer system is coupled via the bus to a display, such as a cathode ray tube (CRT) or liquid crystal display (LCD), for displaying information to a computer user. In some embodiments, an input device, including alphanumeric and other keys, is coupled to the bus for communicating information and command selections to the processor. Another type of user input device is a cursor control, such as a mouse, a trackball, or cursor direction keys for communicating direction information and command selections to the processor and for controlling cursor movement on the display.

In some embodiments, a computer system performs aspects of the present technology. Consistent with certain embodiments of the technology, results are provided by the computer system in response to the processor executing one or more sequences of one or more instructions contained in memory. Such instructions can be read into memory from another computer-readable medium, such as the storage device. Alternatively, hard-wired circuitry can be used in place of or in combination with software instructions to implement the present technology. Thus implementations of the present teachings are not limited to any specific combination of hardware circuitry and software. For example, as described herein, embodiments of the technology comprise the use of storage and transfer of data using "cloud" computing technology, wired (e.g., fiber optic, cable, copper, ADSL, Ethernet, and the like), and/or wireless technology (e.g., IEEE 802.11 and the like). As described herein, in some embodiments, components of the technology are connected via a local area network (LAN), wireless local area network (WLAN), wide area network (WAN) such as the internet, or any other network type, topology, and/or protocol. In some embodiments, the technology comprises use of a portable device such as a hand-held computer, smartphone, tablet computer, laptop computer, palmtop computer, hiptop computer, e.g., to display results, accept input from a user, provide instructions to another computer, store data, and/or perform other steps of methods provided herein. Some embodiments provide for the use of a thin client terminal to display results, accept input from a user, provide instructions to another computer, store data, and/or perform other steps of methods provided herein.

Some embodiments provide a method for determining a target nucleotide sequence, the method comprising determining n nucleotide subsequences of the target nucleotide sequence (indexed over m), wherein the mth nucleotide subsequence has a 5' end at nucleotide $x_m$ of the target nucleotide sequence and has a 3' end at nucleotide $y_m$ of the target nucleotide sequence; the (m+1)th nucleotide subsequence has a 5' end at nucleotide $x_{m+1}$ of the target nucleotide sequence and has a 3' end at nucleotide $y_{m+1}$ of the target nucleotide sequence; and assembling the n nucleotide subsequences to provide a consensus sequence for the target nucleotide sequence, wherein m ranges from 1 to n; $x_{m+1} < y_m$; and $(y_m - x_m) < 100$, 90, 80, 70, 60, 50, 55, 50, 45, 40, 35, or 30 or less, $(y_{m+1} - x_{m+1}) < 100$, 90, 80, 70, 60, 50, 55, 50, 45, 40, 35, or 30 or less, and $(y_{m+1} - y_m) < 20$, 10 or less, or less than 5, 4, or 3, or is equal to 1. In some embodiments the fragments are less than 50 bp; accordingly, in some embodiments $(y_m - x_m) < 50$ and $(y_{m+1} - x_{m+1}) < 50$. In some embodiments the fragments are less than 40 bp; accordingly in some embodiments $(y_m - x_m) < 40$ and $(y_{m+1} - x_{m+1}) < 40$. In some embodiments the fragments are less than 30 bp; accordingly, in some embodiments $(y_m - x_m) < 30$ and $(y_{m+1} - x_{m+1}) < 30$.

In some embodiments the 3' ends of the fragments differ by 4 or 3 bases with respect to the target nucleic acid sequence. Accordingly, in some embodiments $(y_{m+1} - y_m) < 4$ or $(y_{m+1} - y_m) < 3$. In some embodiments the 3' ends of the fragments differ by 1 base with respect to the target nucleic acid sequence. Thus, in some embodiments $(y_{m+1} - y_m) = 1$.

In some embodiments, determining the n nucleotide subsequences comprises priming from a universal sequence. In some embodiments, determining the n nucleotide subsequences comprises terminating polymerization with a 3'-O-blocked nucleotide analog. In some embodiments determining the first nucleotide subsequence and the second nucleotide subsequence comprises terminating polymerization with a 3'-O-alkynyl nucleotide analog. In some embodiments determining the first nucleotide subsequence and the second nucleotide subsequence comprises terminating polymerization with a 3'-O-propargyl nucleotide analog. In some embodiments determining the first nucleotide subsequence and the second nucleotide subsequence comprises terminating polymerization with a nucleotide analog comprising a reversible terminator.

In some embodiments, methods for generating a next-generation sequencing library are provided. In some embodiments the methods comprise amplifying a target nucleotide sequence using a primer comprising a target specific sequence, a universal sequence A, and a barcode nucleotide sequence associated with the target nucleic acid to provide an identifiable amplicon; ligating a first adaptor oligonucleotide comprising a universal sequence B to the 3' end of the amplicon to form an adaptor-amplicon; circularizing the adaptor-amplicon to form a circular template; generating a ladder fragment library from the circular template using a 3'-O-blocked nucleotide analog; and ligating a second adaptor oligonucleotide comprising a universal sequence C to the 3' ends of the fragments of the ladder fragment library to generate the next-generation sequencing library (e.g., using a ligase or a chemical ligation by, e.g., click chemistry, e.g., a copper catalyzed reaction of an alkyne (e.g., a 3' alkyne) and an azide (e.g., a 5' azide)).

In some embodiments, the barcode nucleotide sequence comprises 1 to 20 nucleotides. In some embodiments, the first adaptor oligonucleotide comprises 10 to 80 nucleotides. In some embodiments the nucleotide sequences of the fragments of the ladder fragment library correspond to overlapping nucleotide subsequences within the target nucleotide sequence and the nucleotide sequences of the fragments have 3' ends corresponding to different nucleotides of the target nucleotide sequence. In some embodiments the nucleotide sequences of the fragments of the ladder fragment library comprise less than 100 nucleotides, e.g., less than 90, 80, 70, 60, 50, or 40 nucleotides, e.g., 15 to 50, e.g., 15 to 40 nucleotides.

In some embodiments the first adaptor oligonucleotide comprises a single-stranded DNA and/or the second adaptor oligonucleotide comprises a single-stranded DNA.

In some embodiments generating a ladder fragment library comprises using an oligonucleotide primer complementary to the universal sequence A.

In some embodiments, the methods further comprise amplifying the next-generation sequencing library.

In some embodiments the 3'-O-alkynyl nucleotide analog is a 3'-O-propargyl nucleotide analog. In some embodiments the nucleotide analog comprises a reversible terminator.

The technology further provides methods for determining a sequence of a nucleic acid. For example, in some embodiments, the method comprises generating a next-generation sequencing library according to the technology provided herein; determining a nucleotide sequence of a fragment of the ladder fragment library, said nucleotide sequence comprising a nucleotide subsequence of the target nucleotide sequence; and determining a barcode nucleotide sequence of the fragment of the ladder fragment library.

In some embodiments, determining the nucleotide sequence of a fragment of the ladder fragment library comprises using an oligonucleotide primer complementary to universal sequence C. In addition, in some embodiments determining the barcode nucleotide sequence of the fragment of the ladder fragment library comprises using an oligonucleotide primer complementary to universal sequence B.

In some embodiments the nucleotide sequence of a fragment of the ladder fragment library comprises less than 100 nucleotides, e.g., 15 to 50 nucleotides, e.g., 20 to 50, e.g., 25 to 50, e.g., 30 to 50, e.g., 35 to 50, e.g., 40 to 50 nucleotides. In some embodiments the methods further comprise associating the barcode nucleotide sequence with a source of the target nucleotide sequence.

In some embodiments the methods further comprise collecting or binning nucleotide sequences of fragments of the ladder fragment library having the same barcode nucleotide sequence. In some embodiments, the methods further comprise assembling a plurality of nucleotide sequences of fragments of the ladder fragment library to provide a consensus sequence. In some embodiments the methods further comprise mapping the consensus sequence to a reference sequence.

In some embodiments, to provide for reconstruction of a consensus sequence, the technology includes attaching labels to the nucleic acids, such as nucleic acid binding proteins, optical labels, nucleotide analogs, and others known in the art.

The technology provides related compositions comprising a next-generation sequencing library, wherein the next-generation sequencing library comprises a plurality of nucleic acids, each nucleic acid comprising a universal sequence A, a barcode nucleotide sequence, a second universal sequence B, a nucleotide subsequence of a target nucleotide sequence, and a universal sequence C. In some embodiments the compositions comprise n nucleic acids, wherein, the mth nucleotide subsequence has a 5' end at nucleotide $x_m$ of the target nucleotide sequence and has a 3' end at nucleotide $y_m$ of the target nucleotide sequence; the (m+1)th nucleotide subsequence has a 5' end at nucleotide $x_{m+1}$ of the target nucleotide sequence and has a 3' end at nucleotide $y_{m+1}$ of the target nucleotide sequence; m ranges from 1 to n; $x_m = x_{m+1}$; and $(y_{m+1}-y_m)<20$, 10, or less than 5, 4, 3, or 2. In some embodiments the 3' ends of the fragments of the sequencing library are offset with respect to each other and the target nucleotide sequence by 4 or 3 bases; accordingly, in some embodiments $(y_{m+1}-y_m)<4$ or $(y_{m+1}-y_m)<3$. In some embodiments the 3' ends of the fragments of the sequencing library are offset with respect to each other and the target nucleotide sequence by 1 base; accordingly, in some embodiments $(y_{m+1}-y_m)=1$.

In some embodiments, the universal sequence B comprises 10 to 100 nucleotides and/or the barcode nucleotide sequence comprises 1 to 20 nucleotides.

In some embodiments the compositions further comprise a 3'-O-blocked nucleotide analog such as a 3'-O-alkynyl nucleotide analog, e.g., a 3'-O-propargyl nucleotide analog. In some embodiments the compositions further comprise a sequencing primer. For example, in some embodiments the compositions further comprise a sequencing primer complementary to the universal sequence C and/or a sequencing primer complementary to the universal sequence B.

In some embodiments, the barcode nucleotide sequence is associated with the target nucleotide sequence. In some embodiments the plurality of nucleic acids comprises nucleic acids having different barcode nucleotide sequences and different nucleotide subsequences of a target nucleotide sequence, wherein each barcode nucleotide sequence is associated with the target nucleotide sequence. In some embodiments, the barcode nucleotide sequence is associated with one-to-one correspondence with the target nucleotide sequence.

In some embodiments each nucleic acid of the next-generation sequencing library comprises a 3'-O-blocked nucleotide analog, e.g., a 3'-O-alkynyl nucleotide analog, e.g., a 3'-O-propargyl nucleotide analog. In some embodiments each nucleic acid of the next-generation sequencing library comprises a nucleotide analog comprising a reversible terminator.

Also provided are kits for producing a NGS sequencing library and/or for obtaining sequence information from a target nucleic acid. In some embodiments of the technology are provided a kit comprising a nucleotide analog, e.g., for producing a nucleotide fragment ladder according to the methods provided herein. In some embodiments, the nucleotide analog is a 3'-O-blocked nucleotide analog, e.g., a 3'-O-alkynyl nucleotide analog, e.g., a 3'-O-propargyl nucleotide analog. In some embodiments, conventional A, C, G, U, and/or T nucleotides are provided in a kit as well as one or more (e.g., 1, 2, 3, or 4) A, C, G, U, and/or T nucleotide analogs.

In some embodiments, kits comprise a polymerase (e.g., a natural polymerase, a modified polymerase, and/or an engineered polymerase, etc.), e.g., for amplification (e.g., by thermal cycling, isothermal amplification) or for sequencing, etc. In some embodiments, kits comprise a ligase, e.g., for attaching adaptors to a nucleic acid such as an amplicon or a ladder fragment or for circularizing an adaptor-amplicon. Some embodiments of kits comprise a copper-based catalyst reagent, e.g., for a click chemistry reaction, e.g., to react an azide and an alkynyl group to form a triazole link. Some kit embodiments provide buffers, salts, reaction vessels, instructions, and/or computer software.

In some embodiments, kits comprise primers and/or adaptors. In some embodiments, the adaptors comprise a chemical modification suitable for attaching the adaptor to the nucleotide analog, e.g., by click chemistry. For example, in some embodiments, the kit comprises a nucleotide analog comprising an alkyne group and an adaptor oligonucleotide comprising an azide ($N_3$) group. In some embodiments, a "click chemistry" process such as an azide-alkyne cycloaddition is used to link the adaptor to the fragment via formation of a triazole.

Some embodiments of the technology provide systems for obtaining sequence information. For example, system embodiments comprise a nucleotide analog for producing a fragment ladder from a target nucleic acid and a computer readable medium storing instructions for determining the sequence of the target nucleic acid from assembling short sequence reads. In some embodiments, systems comprise one or more adaptor oligonucleotides (e.g., suitable for attachment to the nucleotide analogs) or other kit components as described above.

For example, some system embodiments are associated with assembling (stitching, reconstructing) a nucleic acid sequence. Embodiments of such systems include various components such as, e.g., a nucleic acid sequencer, a sample sequence data storage, a reference sequence data storage, and an analytics computing device/server/node. In some embodiments, the analytics computing device/server/node is a workstation, mainframe computer, personal computer, mobile device, etc. In some embodiments, the systems comprise functionalities for identifying a barcode, parsing sequences based on a barcode, and binning sequences having common barcodes.

In some embodiments, the nucleic acid sequencer is configured to analyze (e.g., interrogate) a nucleic acid fragment (e.g., a single fragment, a mate-pair fragment, a paired-end fragment, etc.) utilizing all available varieties of techniques, platforms, or technologies to obtain nucleic acid sequence information. In some embodiments, the systems comprise functionalities for making base calls, assessing quality scores, aligning sequences, identifying a barcode, parsing sequences based on a barcode, and binning sequences having common barcodes.

In various embodiments, the nucleic acid sequencer communicates with the sample sequence data storage either directly via a data cable (e.g., a serial cable, a direct cable connection, etc.) or a bus linkage or, alternatively, through a network connection (e.g., internet, LAN, WAN, WLAN, VPN, etc.). In various embodiments, the network connection is a hardwired physical connection. For example, some embodiments provide that the nucleic acid sequencer is communicatively connected (via Category 5 (CAT5), fiber optic, or equivalent cabling) to a data server that is, in turn, communicatively connected (via CAT5, fiber optic, or equivalent cabling) through the internet and to the sample sequence data storage. In various embodiments, the network connection is a wireless network connection (e.g., Wi-Fi, WLAN, etc.), for example, utilizing an IEEE 802.11 (e.g., a/b/g/n, etc.) or equivalent transmission format. In practice, the network connection utilized is dependent upon the particular requirements of the system. In various embodiments, the sample sequence data storage is an integrated part of the nucleic acid sequencer.

In some embodiments, the sample sequence data storage is a database storage device, system, or implementation (e.g., data storage partition, etc.) that is configured to organize and store nucleic acid sequence read data generated by a nucleic acid sequencer (e.g., the short overlapping sequence reads of less than 300 or less than 200 bases, e.g., ~30-50 bases and associated index information such as barcode sequence and metadata associated with the barcode such as sample source, type, target nucleic acid, region of interest, experimental conditions, clinical data, etc.) such that the data can be searched (e.g., by barcode sequence or associated metadata) and retrieved manually (e.g., by a database administrator/client operator) or automatically by way of a computer program/application/software script. In various embodiments, the reference data storage can be any database device, storage system, or implementation (e.g., data storage partition, etc.) that is configured to organize and store reference sequences (e.g., whole/partial genome, whole/partial exome, gene, region, chromosome, BAC, etc.) such that the data can be searched and retrieved manually (e.g., by a database administrator/client operator) or automatically by way of a computer program/application/software script. In various embodiments, the sample nucleic acid sequencing read data is stored on the sample sequence data storage and/or the reference data storage in a variety of different data file types/formats, including, but not limited to: *.fasta, *.csfasta, *seq.txt, *qseq.txt, *.fastq, *.sff, *prb.txt, *.sms, *srs and/or *.qv.

In some embodiments, the sample sequence data storage and the reference data storage are independent standalone devices/systems or implemented on different devices. In some embodiments, the sample sequence data storage and the reference data storage are implemented on the same device/system. In some embodiments, the sample sequence data storage and/or the reference data storage are implemented on the analytics computing device/server/node.

In some embodiments, the analytics computing device/server/node is in communication with the sample sequence data storage and the reference data storage either directly via a data cable (e.g., a serial cable, a direct cable connection, etc.) or a bus linkage or, alternatively, through a network connection (e.g., internet, LAN, WAN, VPN, etc.). In various embodiments, the analytics computing device/server/node hosts an assembler, e.g., a reference mapping engine or a de novo mapping module, and/or a tertiary analysis engine.

In some embodiments, the de novo mapping module is configured to assemble sample nucleic acid sequence reads from the sample data storage into new and previously unknown sequences.

In some embodiments, the reference mapping engine is configured to obtain sample nucleic acid sequence reads (e.g., having a common barcode and having been binned together) from the sample data storage and map them against one or more reference sequences obtained from the reference data storage to assemble the reads into a sequence that is similar but not necessarily identical to the reference sequence using all varieties of reference mapping/alignment techniques and methods. The reassembled sequence can then be further analyzed by one or more optional tertiary analysis engines to identify differences in the genetic makeup (genotype, haplotype), gene expression, or epigenetic status of individuals that can result in large differences in physical characteristics (phenotype). For example, in various embodiments, the tertiary analysis engine is configured to identify various genomic variants (in the assembled sequence) due to mutations, recombination/crossover, or genetic drift; to identify phasing of genetic information; to identify phylogenetic and/or taxonomic information; to identify an individual; to identify a species, genus, or other phylogenetic classification; to identify a drug resistance or a drug susceptibility (sensitivity) marker; to identify a gene fusion; to identify a copy number variation; to identify a methylation status; to associate the sequence with a disease state; etc. Examples of types of genomic variants include, but are not limited to: single nucleotide polymorphisms (SNPs), copy number variations (CNVs), insertions/deletions ("indels"), inversions, duplications, translocations, integrations, etc.

It should be understood, however, that the various engines and modules hosted on the analytics computing device/server/node can be combined or collapsed into a single engine or module, depending on the requirements of the particular application or system architecture. Moreover, in various embodiments, the analytics computing device/server/node hosts additional engines or modules as needed by the particular application or system architecture.

In some embodiments, the mapping and/or tertiary analysis engines are configured to process the nucleic acid and/or reference sequence reads in color space. In various embodiments, the mapping and/or tertiary analysis engines are configured to process the nucleic acid and/or reference sequence reads in base space. It should be understood, however, that the mapping and/or tertiary analysis engines can process or analyze nucleic acid sequence data in any schema or format as long as the schema or format conveys the base identity and position of the nucleic acid sequence.

In some embodiments, the sample nucleic acid sequencing read and referenced sequence data are supplied to the analytics computing device/server/node in a variety of different input data file types/formats, including, but not limited to: *.fasta, *.csfasta, *seq.txt, *qseq.txt, *.fastq, *.sff, *prb.txt, *.sms, *srs and/or *.qv.

Some embodiments provide a client terminal. The client terminal is, in some embodiments, a thin client or, in some embodiments, a thick client computing device. In some embodiments, the client terminal comprises a web browser (e.g., Internet Explorer, Firefox, Safari, Chrome, etc.) that is used to control the operation of the reference mapping engine, the de novo mapping module, and/or the tertiary analysis engine. That is, the client terminal can access the reference mapping engine, the de novo mapping module, and/or the tertiary analysis engine using a browser to control their functions. For example, the client terminal can be used to configure the operating parameters (e.g., mismatch constraint, quality value thresholds, etc.) of the various engines, depending on the requirements of the particular application. Similarly, the client terminal can also comprise a display to display the results of the analysis performed by the assembler, the reference mapping engine, the de novo mapping module, and/or the tertiary analysis engine.

The technology provided herein, in method, composition, kit, and system embodiments, finds use, e.g., to prepare a NGS library for sequencing, to acquire a nucleotide sequence, to map a single nucleotide polymorphism, to distinguish alleles, to sequence a genome, to identify rare minor population variants (e.g., somatic mutations in cancer or a low-abundance pathogen against a large background of host or non-pathogen DNA), etc.

Sequencing may be by any method known in the art. In certain embodiments, sequencing is sequencing by synthesis. In other embodiments, sequencing is single molecule sequencing by synthesis. In certain embodiments, sequencing involves hybridizing a primer to the template to form a template/primer duplex, contacting the duplex with a polymerase enzyme in the presence of detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotides determines the sequence of the nucleic acid. Exemplary detectable labels include radiolabels, florescent labels, enzymatic labels, etc. In particular embodiments, the detectable label may be an optically detectable label, such as a fluorescent label. Exemplary fluorescent labels (for sequencing and/or other purposes such as labeling a nucleic acid, primer, probe, etc.) include cyanine, rhodamine, fluorescein, coumarin, BODIPY, alexa, or conjugated multi-dyes.

Some embodiments provide a method for generating a next-generation sequencing library, the method comprising amplifying a target nucleotide sequence using a primer comprising a target specific sequence, a universal sequence A, and a barcode nucleotide sequence (e.g., comprising 1 to 20 nucleotides) associated with the target nucleic acid to provide an identifiable amplicon; ligating a first adaptor oligonucleotide (e.g., a single-stranded DNA, e.g., comprising 10 to 80 nucleotides) comprising a universal sequence B to the 3' end of the amplicon to form an adaptor-amplicon; circularizing the adaptor-amplicon to form a circular template; generating from the circular template by use of a primer complementary to the universal sequence A and a 3'-O-blocked nucleotide analog (e.g., a 3'-O-alkynyl nucleotide analog, a 3'-O-propargyl nucleotide analog, or comprising a reversible terminator) a ladder fragment library comprising a plurality of fragments; and ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library, wherein the nucleotide sequences of the fragments of the ladder fragment library comprise 15 to 40 nucleotides, the nucleotide sequences of the fragments of the ladder fragment library correspond to overlapping nucleotide subsequences within the target nucleotide sequence, and the nucleotide sequences of the fragments of the ladder fragment library have 3' ends corresponding to different nucleotides of the target nucleotide sequence.

Some embodiments provide a method for determining a target nucleotide sequence, the method comprising amplifying a target nucleotide sequence using a primer comprising a target specific sequence, a universal sequence A, and a barcode nucleotide sequence (e.g., comprising 1 to 20 nucleotides) associated with the target nucleic acid to provide an amplicon; ligating a first adaptor oligonucleotide (e.g., a single-stranded DNA, e.g., comprising 10 to 80 nucleotides) comprising a universal sequence B to the 3' end of the amplicon to form an adaptor-amplicon; circularizing the adaptor-amplicon to form a circular template; generating from the circular template by use of a primer complementary to the universal sequence A and a 3'-O-blocked nucleotide analog (e.g., a 3'-O-alkynyl nucleotide analog, a 3'-O-propargyl nucleotide analog, or comprising a reversible terminator) a ladder fragment library comprising a plurality of fragments; ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library; determining a nucleotide sequence of a fragment of the ladder fragment library (e.g., using an oligonucleotide primer complementary to universal sequence C), said nucleotide sequence comprising a nucleotide subsequence of the target nucleotide sequence; determining a barcode nucleotide sequence of the fragment of the ladder fragment library (e.g., using an oligonucleotide primer complementary to universal sequence B); associating the barcode nucleotide sequence with a source of the target nucleotide sequence; binning nucleotide sequences of fragments of the ladder fragment library having the same barcode nucleotide sequence; assembling a plurality of nucleotide sequences of fragments of the ladder fragment library to provide a consensus sequence; and mapping the consensus sequence to a reference sequence, wherein the nucleotide sequences of the fragments of the ladder fragment library comprise 15 to 50, 15 to 40, or 15 to 30 nucleotides, the nucleotide sequences of the fragments of the ladder fragment library correspond to overlapping nucleotide subsequences within the target nucleotide sequence, the nucleotide sequences of the fragments of the ladder fragment library have 3' ends corresponding to different nucleotides of the target nucleotide sequence, and the consensus sequence retains phasing and/or linkage information of the target nucleic acid.

Some embodiments are related to methods, compositions, kits, and systems for sequencing a nucleic acid (e.g., by NGS) by generating a next-generation sequencing library using modified nucleotides, e.g., one or more 3'-O-modified nucleotides such as 3'-O-alkynyl modified nucleotides. In some embodiments, the 3'-O-modified nucleotides are 3'-O-propargyl nucleotides (e.g., 3'-O-propargyl-dNTP, e.g., 3'-O-propargyl-dATP, 3'-O-propargyl-dCTP, 3'-O-propargyl-dGTP, 3'-O-propargyl-dTTP; see, e.g., U.S. patent application Ser. Nos. 14/463,412 and 14/463,416; and Int'l Pat. App. PCT/US2014/051726, each of which is incorporated herein by reference in its entirety for all purposes). For example, embodiments of the technology are related to generating a sequencing library (e.g., for NGS) comprising a nucleic acid fragment ladder produced by incorporating chain-terminating 3'-O-modified nucleotides by a polymerase during the in vitro synthesis of a nucleic acid.

Particular embodiments are related to generating a nucleic acid fragment ladder using a polymerase reaction comprising standard dNTPs and 3'-O-propargyl-dNTPs at a molar ratio of from 1:500 to 500:1 (e.g., a ratio of standard dNTPs to 3'-O-propargyl-dNTPs that is 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1). Terminated nucleic acid fragments produced by methods described herein comprise a propargyl group on their 3' ends. Further embodiments are related to attaching an adaptor to the 3' ends of the nucleic acid fragments using chemical conjugation. For example, in some embodiments a 5'-azido-modified oligonucleotide (e.g., a 5'-azido-methyl-modified oligonucleotide) is conjugated to the 3'-propargyl-terminated nucleic acid fragments by click chemistry (e.g., in a reaction catalyzed by a copper (e.g., copper (I)) reagent). In some embodiments, a target region is first amplified (e.g., by PCR) to produce a target amplicon for sequencing. In some embodiments, amplifying the target region comprises amplification of the target region for 5 to 15 cycles (e.g., a "low-cycle" amplification).

Further embodiments provide that the target amplicon comprises a tag (e.g., comprises a barcode sequence), e.g., the target amplicon is an identifiable amplicon. In some embodiments, a primer used in the amplification of the target region comprises a tag (e.g., comprising a barcode sequence) that is subsequently incorporated into the target amplicon (e.g., in a "copy and tag" reaction) to produce an identifiable amplicon. In some embodiments, an adaptor comprising the tag (e.g., comprising a barcode sequence) is ligated to the target amplicon after amplification (e.g., in a ligase reaction) to produce an identifiable adaptor-amplicon. In some embodiments, the primer used to produce an identifiable amplicon in a copy and tag reaction comprises a 3' region comprising a target-specific priming sequence and a 5' region comprising two different universal sequences (e.g., a universal sequence A and a universal sequence B) flanking a degenerate sequence. In some embodiments, an adaptor ligated to an amplicon to produce an identifiable adaptor-amplicon is a double stranded adaptor, e.g., comprising one strand comprising a degenerate sequence (e.g., comprising 8 to 12 bases) flanked on both the 5' end and the 3' end by two different universal sequences (e.g., a universal sequence A and a universal sequence B) and a second strand comprising a universal sequence C (e.g., at the 5' end) and a sequence (e.g., at the 3' end) that is complementary to the universal sequence B and that has an additional T at the 3'-terminal position.

Then, embodiments of the technology provide for the generation of nucleic acid ladder fragments from the adaptor-amplicon, e.g., to provide a sequencing library for NGS. In particular, the technology provides for the generation of a 3'-O-propargyl-dN terminated nucleic acid ladder for nucleic acid sequencing (e.g., NGS), e.g., by using a polymerase reaction comprising standard dNTPs and 3'-O-propargyl-dNTPs at a molar ratio of from 1:500 to 500:1 (standard dNTPs to 3'-O-propargyl-dNTPs). Then, in some embodiments, the technology provides for attaching an adaptor to the 3' ends of the nucleic acid fragments using chemical conjugation. For example, in some embodiments, a 5'-azido-modified oligonucleotide (e.g., a 5'-azido-methyl-modified oligonucleotide) is conjugated to the 3'-propargyl-terminated nucleic acid fragments by click chemistry (e.g., in a reaction catalyzed by a copper (e.g., copper (I)) reagent).

Accordingly, some embodiments provide a method for generating a next-generation sequencing library, the method comprising amplifying a target nucleotide sequence using a primer comprising a target specific sequence, a universal sequence A, a universal sequence B, and a barcode nucleotide sequence (e.g., comprising 1 to 20 nucleotides) associated with the target nucleic acid to provide an identifiable amplicon; generating a nucleic acid fragment ladder from the identifiable amplicon using a 3'-O-blocked nucleotide analog (e.g., a 3'-O-alkynyl nucleotide analog, a 3'-O-propargyl nucleotide analog); and ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library, wherein the nucleotide sequences of the fragments of the ladder fragment library comprise 15 to 100 nucleotides, the nucleotide sequences of the fragments of the ladder fragment library correspond to overlapping nucleotide subsequences within the target nucleotide sequence, and the nucleotide sequences of the fragments of the ladder fragment library have 3' ends corresponding to different nucleotides of the target nucleotide sequence.

Some embodiments provide a method for generating a next-generation sequencing library, the method comprising amplifying a target nucleotide sequence to provide an amplicon; ligating an adaptor (e.g., an adaptor comprising one strand comprising a degenerate sequence (e.g., comprising 8 to 12 bases) flanked on both the 5' end and the 3' end by two different universal sequences (e.g., a universal sequence A and a universal sequence B) and a second strand comprising a universal sequence C (e.g., at the 5' end) and a sequence (e.g., at the 3' end) that is complementary to the universal sequence B and that has an additional T at the 3'-terminal position) to the amplicon to produce an adaptor-amplicon; generating a nucleic acid fragment ladder from the adaptor-amplicon using a 3'-0-blocked nucleotide analog (e.g., a 3'-O-alkynyl nucleotide analog, a 3'-O-propargyl nucleotide analog); and ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library, wherein the nucleotide sequences of the fragments of the ladder fragment library comprise 15 to 100 nucleotides, the nucleotide sequences of the fragments of the ladder fragment library correspond to overlapping nucleotide subsequences within the target nucleotide sequence, and the nucleotide sequences of the fragments of the ladder fragment library have 3' ends corresponding to different nucleotides of the target nucleotide sequence.

Some embodiments provide a method for determining a target nucleotide sequence, the method comprising amplifying a target nucleotide sequence using a primer comprising a target specific sequence, a universal sequence A, a universal sequence B, and a barcode nucleotide sequence (e.g., comprising 1 to 20 nucleotides) associated with the target nucleic acid to provide an identifiable amplicon; generating a nucleic acid fragment ladder from the identifiable amplicon using a 3'-O-blocked nucleotide analog (e.g., a 3'-O-alkynyl nucleotide analog, a 3'-O-propargyl nucleotide analog); and ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library; determining a nucleotide sequence of a fragment of the ladder fragment library (e.g., using an oligonucleotide primer complementary to universal sequence C), said nucleotide sequence comprising a nucleotide subsequence of the target nucleotide sequence; determining a barcode nucleotide sequence of the fragment of the ladder fragment library; associating the barcode nucleotide sequence with a source of the target nucleotide sequence; binning nucleotide sequences of fragments of the ladder fragment library having the same barcode nucleotide sequence; assembling a plurality of nucleotide sequences of fragments of the ladder fragment library to provide a consensus sequence; and, in some embodiments, mapping the consensus sequence to a reference sequence, wherein the nucleotide sequences of the fragments of the ladder fragment library comprise 15 to 50, 15 to 40, or 15 to 30 nucleotides, the nucleotide sequences of the fragments of the ladder fragment library correspond to overlapping nucleotide subsequences within the target nucleotide sequence, the nucleotide sequences of the fragments of the ladder fragment library have 3' ends corresponding to different nucleotides of the target nucleotide sequence, and the consensus sequence retains phasing and/or linkage information of the target nucleic acid.

Some embodiments provide a method for determining a target nucleotide sequence, the method comprising amplifying a target nucleotide sequence to provide an amplicon; ligating an adaptor (e.g., an adaptor comprising one strand comprising a degenerate sequence (e.g., comprising 8 to 12 bases) flanked on both the 5' end and the 3' end by two different universal sequences (e.g., a universal sequence A and a universal sequence B) and a second strand comprising a universal sequence C (e.g., at the 5' end) and a sequence (e.g., at the 3' end) that is complementary to the universal sequence B and that has an additional T at the 3'-terminal position) to the amplicon to produce an adaptor-amplicon; generating a nucleic acid fragment ladder from the adaptor-amplicon using a 3'-O-blocked nucleotide analog (e.g., a 3'-O-alkynyl nucleotide analog, a 3'-O-propargyl nucleotide analog); and ligating (e.g., by click chemistry, e.g., using a copper-based catalyst reagent, e.g., to form a triazole from an azide and an alkynyl) a second adaptor oligonucleotide (e.g., a single-stranded DNA) comprising a universal sequence C to the 3' ends of the fragments of the ladder fragment library to generate a next-generation sequencing library; determining a nucleotide sequence of a fragment of the ladder fragment library (e.g., using an oligonucleotide primer complementary to universal sequence C), said nucleotide sequence comprising a nucleotide subsequence of the target nucleotide sequence; determining a barcode nucleotide sequence of the fragment of the ladder fragment library; associating the barcode nucleotide sequence with a source of the target nucleotide sequence; binning nucleotide sequences of fragments of the ladder fragment library having the same barcode nucleotide sequence; assembling a plurality of nucleotide sequences of fragments of the ladder fragment library to provide a consensus sequence; and, in some embodiments, mapping the consensus sequence to a reference sequence, wherein the nucleotide sequences of the fragments of the ladder fragment library comprise 15 to 50, 15 to 40, or 15 to 30 nucleotides, the nucleotide sequences of the fragments of the ladder fragment library correspond to overlapping nucleotide subsequences within the target nucleotide sequence, the nucleotide sequences of the fragments of the ladder fragment library have 3' ends corresponding to different nucleotides of the target nucleotide sequence, and the consensus sequence retains phasing and/or linkage information of the target nucleic acid.

Some embodiments provide a method for determining a target nucleotide sequence, the method comprising determining a first nucleotide subsequence of the target nucleotide sequence (e.g., by priming from a universal sequence and, e.g., terminating polymerization with a 3'-O-blocked nucleotide analog such as a 3'-O-alkynyl nucleotide analog or a 3'-O-propargyl nucleotide analog or terminating polymerization with a nucleotide analog comprising a reversible terminator), said first nucleotide subsequence having a 5' end at nucleotide x1 of the target nucleotide sequence and having a 3' end at nucleotide y1 of the target nucleotide sequence; determining a second nucleotide subsequence of the target nucleotide sequence (e.g., by priming from a universal sequence and, e.g., terminating polymerization with a 3'-O-blocked nucleotide analog such as a 3'-O- alkynyl nucleotide analog or a 3'-O-propargyl nucleotide analog or terminating polymerization with a nucleotide analog comprising a reversible terminator), said second nucleotide subsequence having a 5' end at nucleotide x2 of the target nucleotide sequence and having a 3' end at nucleotide y2 of the target nucleotide sequence; assembling the first nucleotide subsequence and the second nucleotide subsequence to provide a consensus sequence (e.g., comprising 100, 200, 300, 400, 500, 600, 700, 800, 900, 1000, or more than 1000, e.g., 2000, 2500, 3000, 3500, 4000, 4500, or 5000, or more than 5000 bases) for the target nucleotide sequence; identifying a source or sample of the target nucleotide sequence by decoding a barcode nucleotide sequence; mapping the consensus sequence (e.g., retaining phasing and/or linkage information of the target nucleic acid) to a reference sequence, wherein x2<y1; and (y1−x1)<100 (e.g., (y1−x1)<90, 80, 70, 60, 55, 50, 45, 40, 35, or 30), (y2−x2)<100 (e.g., (y1−x1)<90, 80, 70, 60, 55, 50, 45, 40, 35, or 30), and (y2−y1)<20 (e.g., (y2−y1)<10, (y2−y1)<5, (y2−y1)<4, (y2−y1)<3, (y2−y1)<2, or (y2−y1)=1).

Some embodiments provide a method for determining a target nucleotide sequence, the method comprising determining n nucleotide subsequences of the target nucleotide sequence (e.g., by priming from a universal sequence and, e.g., terminating polymerization with a 3'-O-blocked nucleotide analog such as a 3'-O-alkynyl nucleotide analog or a 3'-O-propargyl nucleotide analog or terminating polymerization with a nucleotide analog comprising a reversible terminator), wherein the mth nucleotide subsequence has a 5' end at nucleotide $x_m$ of the target nucleotide sequence and has a 3' end at nucleotide $y_m$ of the target nucleotide sequence; and the (m+1)th nucleotide subsequence has a 5' end at nucleotide $x_{m+1}$ of the target nucleotide sequence and has a 3' end at nucleotide $y_{m+1}$ of the target nucleotide sequence; assembling the n nucleotide subsequences to provide a consensus sequence (e.g., comprising 100, 200, 300, 400, 500, 600, 700, 800, 900, 1000, or more than 1000 bases, e.g., 2000, 2500, 3000, 3500, 4000, 4500, or 5000 or more than 5000 bases) for the target nucleotide sequence; identifying a source or sample of the target nucleotide sequence by decoding a barcode nucleotide sequence; and mapping the consensus sequence to a reference sequence, wherein: m ranges from 1 to n; $x_{m+1}<y_m$; and $(y_m−x_m)<100$ (e.g., $(y_m−x_m)<90, 80, 70, 60, 55, 50, 45, 40, 35,$ or $30$), $(y_{m+1}−x_{m+1})<100$ (e.g., $(y_{m+1}−x_{m+1})<90, 80, 70, 60, 55, 50, 45, 40, 35,$ or $30$), and $(y_{m+1}−y_m)<20$ (e.g., $(y_{m+1}−y_m)<10, (y_{m+1}−y_m)<5, (y_{m+1}−y_m)<4, (y_{m+1}−y_m)<3,$ or $(y_{m+1}−y_m)=1$) and the consensus sequence retains phasing and/or linkage information of the target nucleic acid.

Some embodiments of the technology provide a composition for use as a next-generation sequencing library to obtain a sequence of a target nucleic acid, the composition comprising a 3'-O-blocked nucleotide analog, a 3'-O-alkynyl nucleotide analog, a 3'-O-propargyl nucleotide analog, or a nucleotide analog comprising a reversible terminator; a sequencing primer (e.g., complementary to a universal sequence C); a second sequencing primer (e.g., complementary to a universal sequence B); and n nucleic acids comprising a 3'-O-blocked nucleotide analog, a 3'-O-alkynyl nucleotide analog, or a 3'-O-propargyl nucleotide analog linked (e.g., by a triazole link formed, e.g., by click chemistry, e.g., by a reaction between an azide and an alkyl catalyzed by a copper-based catalyst) to an adaptor (e.g., a next-generation sequencing adaptor oligonucleotide), or a nucleotide analog comprising a reversible terminator, wherein each nucleic acid comprises a nucleotide subsequence of the target nucleic acid, a universal sequence B comprising 10 to 100 nucleotides, a universal sequence C comprising 10 to 100 nucleotides, and/or a barcode nucleotide sequence comprising 1 to 20 nucleotides, wherein the mth nucleotide subsequence has a 5' end at nucleotide $x_m$ of the target nucleotide sequence and has a 3' end at nucleotide $y_m$ of the target nucleotide sequence; the (m+1)th nucleotide subsequence has a 5' end at nucleotide $x_{m+1}$ of the target nucleotide sequence and has a 3' end at nucleotide $y_{m+1}$ of the target nucleotide sequence; m ranges from 1 to n; $x_m=x_{m+1}$; $(y_{m+1}−y_m)<20$ (e.g., $(y_{m+1}−y_m)<15, (y_{m+1}−y_m)<10, (y_{m+1}−y_m)<5, (y_{m+1}−y_m)<4, (y_{m+1}−y_m)<3,$ or $(y_{m+1}−y_m)=1$); the n nucleic acids comprises nucleic acids having different barcode nucleotide sequences and different nucleotide subsequence of a target nucleotide sequence, wherein each barcode nucleotide sequence is associated (e.g., with one-to-one correspondence) with a target nucleotide sequence.

Some embodiments of the technology provide a composition for use as a next-generation sequencing library to obtain a sequence of a target nucleic acid, the composition comprising n nucleic acids (e.g., a nucleic acid fragment library), wherein each of the n nucleic acids comprises a 3'-O-blocked nucleotide analog (e.g., a 3'-O-alkynyl nucleotide analog such as a 3'-O-propargyl nucleotide analog). In some embodiments, each nucleic acid of the n nucleic acids comprises a nucleotide subsequence of a target nucleotide sequence. In particular, embodiments provide a composition comprising n nucleic acids, wherein each of the n nucleic acids is terminated by a 3'-O-blocked nucleotide analog (e.g., a 3'-O-alkynyl nucleotide analog such as a 3'-O-propargyl nucleotide analog). Further embodiments provide a composition comprising n nucleic acids (e.g., a nucleic acid fragment library), wherein each of the n nucleic acids comprises a 3'-O-blocked nucleotide analog (e.g., a 3'-O-alkynyl nucleotide analog such as a 3'-O-propargyl nucleotide analog) and each of the n nucleic acids is conjugated (e.g., linked) to an oligonucleotide adaptor by a triazole linkage (e.g., a linkage formed from a chemical conjugation of a propargyl group and an azido group, e.g., by a click chemistry reaction). For example, some embodiments provide a composition comprising n nucleic acids (e.g., a nucleic acid fragment library), wherein each of the n nucleic acids comprises a 3'-O-propargyl nucleotide analog (e.g., a 3'-O-propargyl-dA, 3'-O-propargyl-dC, 3'-O-propargyl-dG, and/or a 3'-O-propargyl-dT) conjugated (e.g., linked) to an oligonucleotide adaptor by a triazole linkage (e.g., a linkage formed from a chemical conjugation of a propargyl group and an azido group, e.g., by a click chemistry reaction).

In some embodiments, the composition for use as a next-generation sequencing library to obtain a sequence of a target nucleic acid is produced by a method comprising synthesizing a n nucleic acids (e.g., a nucleic acid fragment library) using a mixture of dNTPs and one or more 3'-O-blocked nucleotide analog(s) (e.g., one or more 3'-O-alkynyl nucleotide analog(s) such as one or more 3'-O-propargyl nucleotide analog(s)), e.g., at a molar ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1). In some embodiments, the composition is produced using a polymerase obtained from, derived from, isolated from, cloned from, etc. a *Thermococcus* species (e.g., an organism of the taxonomic lineage Archaea; Euryarchaeota; Thermococci; Thermococcales; Thermococcaceae; *Thermococcus*). In some embodiments, the polymerase is obtained from, derived from, isolated from, cloned from, etc. a *Thermococcus* species 9°N-7. In some embodiments, the polymerase comprises amino acid substitutions that provide for improved incorporation of modified substrates such as modified dideoxynucleotides, ribonucleotides, and acyclonucleotides. In some embodiments, the polymerase comprises amino acid substitutions that provide for improved incorporation of nucleotide analogs comprising modified 3' functional groups such as the 3'-O-propargyl dNTPs described herein. In some embodiments the amino acid sequence of the polymerase comprises one or more amino acid substitutions relative to the *Thermococcus* sp. 9°N-7 wild-type polymerase amino acid sequence, e.g., a substitution of alanine for the aspartic acid at amino acid position 141 (D141A), a substitution of alanine for the glutamic acid at amino acid position 143 (E143A), a substitution of valine for the tyrosine at amino acid position 409 (Y409V), and/or a substitution of leucine for the alanine at amino acid position 485 (A485L). In some embodiments, the polymerase is provided in a heterologous host organism such as *Escherichia coli* that comprises a cloned *Thermococcus* sp. 9°N-7 polymerase gene, e.g., comprising one or more mutations (e.g., D141A, E143A, Y409V, and/or A485L). In some embodiments, the polymerase is a *Thermococcus* sp. 9°N-7 polymerase sold under the trade name THERMINATOR (e.g., THERMINATOR II) by New England BioLabs (Ipswich, Mass.).

Accordingly, the technology relates to reaction mixtures comprising a target nucleic acid, a mixture of dNTPs and one or more 3'-O-blocked nucleotide analog(s) (e.g., one or more 3'-O-alkynyl nucleotide analog(s) such as one or more 3'-O-propargyl nucleotide analog(s)), e.g., at a molar ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1), and a polymerase for synthesizing a nucleic acid using the dNTPs and one or more 3'-O-blocked nucleotide analog(s) (e.g., a polymerase obtained from, derived from, isolated from, cloned from, etc. a *Thermococcus* species). In some embodiments, the target nucleic acid is an amplicon. In some embodiments, the target nucleic acid comprises a barcode. In some embodiments, the target nucleic acid is an amplicon comprising a barcode. In some embodiments, the target nucleic acid is an amplicon ligated to an adaptor comprising a barcode. Some embodiments provide reaction mixtures that comprises a plurality of target nucleic acids, each target nucleic acid comprising a barcode associated with an identifiable characteristic of the target nucleic acid.

Some embodiments provide a reaction mixture composition comprising a template (e.g., a circular template, e.g., comprising a universal nucleotide sequence and/or a barcode nucleotide sequence) comprising a subsequence of a target nucleic acid, a polymerase, one or more fragments of a ladder fragment library, and a 3'-O-blocked nucleotide analog.

Some embodiments provide a reaction mixture composition comprising a library of nucleic acids, the library of nucleic acids comprising overlapping short nucleotide sequences tiled over a target nucleic acid (e.g., the overlapping short nucleotide sequences cover a region of the target nucleic acid comprising 100 bases, 200 bases, 300 bases, 400 bases, 500 bases, 600 bases, 700 bases, 800 bases, 900 bases, 1000 bases, or more than 1000 bases, e.g., 2000 bases, 2500 bases, 3000 bases, 3500 bases, 4000 bases, 4500 bases, 5000 bases, or more than 5000 bases) and offset from one another by 1-20, 1-10, or 1-5 bases (e.g., 1 base) and each nucleic acid of the library comprising less than 100 bases, less than 90 bases, less than 80 bases, less than 70 bases, less than 60 bases, less than 50 bases, less than 45 bases, less than 40 bases, less than 35 bases, or less than 30 bases.

Some embodiments provide a kit for generating a sequencing library, the kit comprising an adaptor oligonucleotide comprising a first reactive group (e.g., an azide), a 3'-0-blocked nucleotide analog (e.g., a 3'-O-alkynyl nucleotide analog or a 3'-O-propargyl nucleotide analog, e.g., comprising an alkyne group, e.g., comprising a second reactive group that forms a chemical bond with the first reactive group, e.g., using click chemistry), a polymerase (e.g., a polymerase for isothermal amplification or thermal cycling), a second adaptor oligonucleotide, one or more compositions comprising a nucleotide or a mixture of nucleotides, and a ligase or a copper-based click chemistry catalyst reagent.

In some embodiments of kits, kits comprise one or more 3'-O-blocked nucleotide analog(s) (e.g., one or more 3'-O-alkynyl nucleotide analog(s) such as one or more 3'-O-propargyl nucleotide analog(s) and one or more adaptor oligonucleotides comprising an azide group (e.g., a 5'-azido oligonucleotide, e.g., a 5'-azido-methyl oligonucleotide). Some kit embodiments further provide a 5'-azido-methyl oligonucleotide comprising a barcode. Some kit embodiments further provide a plurality of 5'-azido-methyl oligonucleotides comprising a plurality of barcodes (e.g., each 5'-azido-methyl oligonucleotide comprises a barcode that is distinguishable from one or more other barcodes of one or more other 5'-azido-methyl oligonucleotide(s) comprising a different barcode). Further kit embodiments comprise a click chemistry catalytic reagent (e.g., a copper(I) catalytic reagent).

Some kit embodiments comprise one or more standard dNTPs in addition to the one or more one or more 3'-O-blocked nucleotide analog(s) (e.g., one or more 3'-O-alkynyl nucleotide analog(s) such as one or more 3'-O-propargyl nucleotide analog(s). For instance, some kit embodiment provide dATP, dCTP, dGTP, and dTTP, either in separate vessels or as a mixture with one or more 3'-O-propargyl-bdATP, 3'-O-propargyl-dCTP, 3'-O-propargyl-dGTP, and/or 3'-O-propargyl-dATP.

Some kit embodiments further comprise a polymerase obtained from, derived from, isolated from, cloned from, etc. a *Thermococcus* species (e.g., an organism of the taxonomic lineage Archaea; Euryarchaeota; Thermococci; Thermococcales; Thermococcaceae; *Thermococcus*). In some embodiments, the polymerase is obtained from, derived from, isolated from, cloned from, etc. a *Thermococcus* species 9°N-7. In some embodiments, the polymerase comprises amino acid substitutions that provide for improved incorporation of modified substrates such as modified dideoxynucleotides, ribonucleotides, and acyclonucleotides. In some embodiments, the polymerase comprises amino acid substitutions that provide for improved incorporation of nucleotide analogs comprising modified 3' functional groups such as the 3'-O-propargyl dNTPs described herein. In some embodiments the amino acid sequence of the polymerase comprises one or more amino acid substitutions relative to the *Thermococcus* sp. 9°N-7 wild-type polymerase amino acid sequence, e.g., a substitution of alanine for the aspartic acid at amino acid position 141 (D141A), a substitution of alanine for the glutamic acid at amino acid position 143 (E143A), a substitution of valine for the tyrosine at amino acid position 409 (Y409V), and/or a substitution of leucine for the alanine at amino acid position 485 (A485L). In some embodiments, the polymerase is provided in a heterologous host organism such as *Escherichia coli* that comprises a cloned *Thermococcus* sp. 9°N-7 polymerase gene, e.g., comprising one or more mutations (e.g., D141A, E143A, Y409V, and/or A485L). In some embodiments, the polymerase is a *Thermococcus* sp. 9°N-7 polymerase sold under the trade name THERMINATOR (e.g., THERMINATOR II) by New England BioLabs (Ipswich, Mass.).

Accordingly, some kit embodiments comprise one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP), a mixture of standard dNTPs (e.g., dATP, dCTP, dGTP, and dTTP), one or more 5'-azido-methyl oligonucleotide adaptors, a polymerase obtained from, derived from, isolated from, cloned from, etc. a *Thermococcus* species, and a click chemistry catalyst for forming a triazole from an azide group and an alkyl group. In some embodiments, the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP) are provided together, e.g., the kit comprises a solution comprising the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP). In some embodiments, the solution comprises the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP) at a ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1).

Some embodiments of kits further comprise software for processing sequence data, e.g., to extract nucleotide sequence data from the data produced by a sequencer; to identify barcodes and target subsequences from the data produced by a sequencer; to align and/or assemble subsequences from the data produced by a sequencer to produce a consensus sequence; and/or to align subsequences and/or a consensus sequence to a reference sequence (e.g., to identify sequence differences (e.g., to identify alleles, homologs, phylogenetic relationships, chromosomes, sequence similarities or differences, mutations, and/or sequencing errors, etc.) and/or to correct sequence anomalies (e.g., sequencing errors)).

Some embodiments provide a system for sequencing a target nucleic acid, the system comprising an adaptor oligonucleotide comprising a first reactive group (e.g., an azide), a 3'-0-blocked nucleotide analog (e.g., a 3'-O-alkynyl nucleotide analog or a 3'-O-propargyl nucleotide analog, e.g., comprising an alkyne group and, e.g., comprising a second reactive group that forms a chemical bond with the first reactive group, e.g., using click chemistry, e.g., using a copper-based click chemistry catalyst), a sequencing apparatus, a nucleic acid fragment ladder (e.g., comprising a plurality of nucleic acids having 3' ends that differ by less than 20 nucleotides, less than 10 nucleotides, less than 5 nucleotides, less than 4 nucleotides, less than 3 nucleotides, or by 1 nucleotide), and software for assembling short overlapping nucleotide sequences into a consensus sequence, wherein each short nucleotide sequence has less than 100, less than 90, less than 80, less than 70, less than 60, less than 50, less than 45, less than 40, less than 35, or less than 30 bases; the short nucleotide sequences are tiled over a target nucleic acid having at least 100, 200, 300, 400, 500, 600, 700, 800, 900, 1000, 2000, 2500, 3000, 3500, 4000, 5000, or more than 5000 bases; and the short nucleotide sequences are offset from one another by 1-20, 1-10, or 1-5 bases.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 2 is a schematic depicting an embodiment of the technology for producing a library for next-generation sequencing. FIG. 2C shows another embodiment of the technology.

Figure 4H:
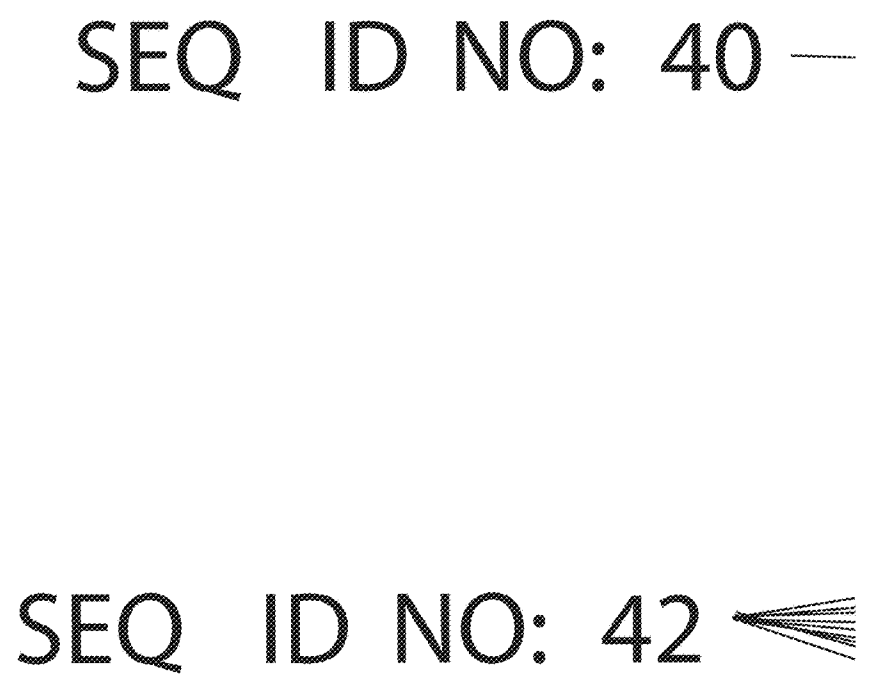
Figure 4J:
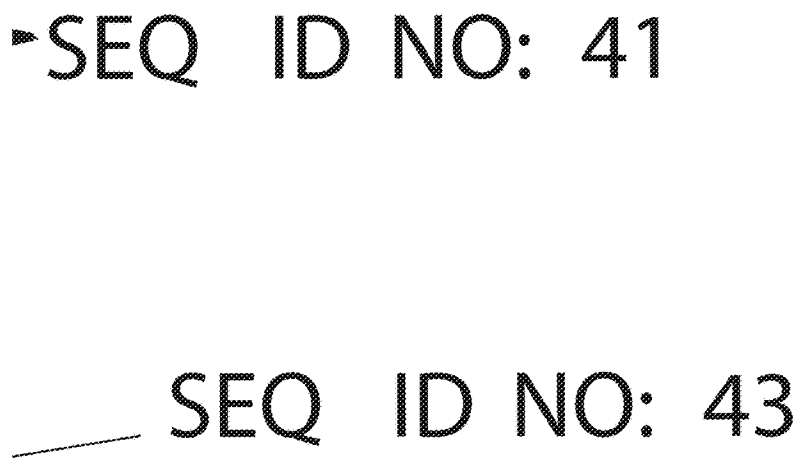

FIGS. 4A-4J show a schematic depicting an embodiment of the technology for sequencing a nucleic acid. FIGS. 4B-4J provide magnified views of subregions of the schematic. FIG. 4A provides a map indicating the relative locations of each of FIGS. 4B-4J in the schematic. The sequences shown in the schematic are provided in the sequence listing.

FIG. 5A is a flowchart showing an embodiment of the technology comprising obtaining sequence data from a NGS library and extracting the overlapping subsequences of the target sequence. FIG. 5B is a flowchart showing an embodiment of the technology for extracting sequence data comprising concatenating sequence data files, identifying and extracting target sequence, and aligning the target sequences to provide a consensus sequence.

FIG. 6A shows sequence alignment of 40-bp reads and the corresponding sequence coverage profile. The consensus and reference sequences are indicated by black bars. The reference sequence is a 177-bp sequence comprising exon 2 of human KRAS and partial flanking intron sequences as provided by SEQ ID NO: 44. The consensus sequence is the same as the reference sequence and also has the sequence provided by SEQ ID NO: 44. FIG. 6B shows the predicted short read sequence alignment and corresponding sequence coverage profile for a theoretical template reference sequence.

Figure 1:
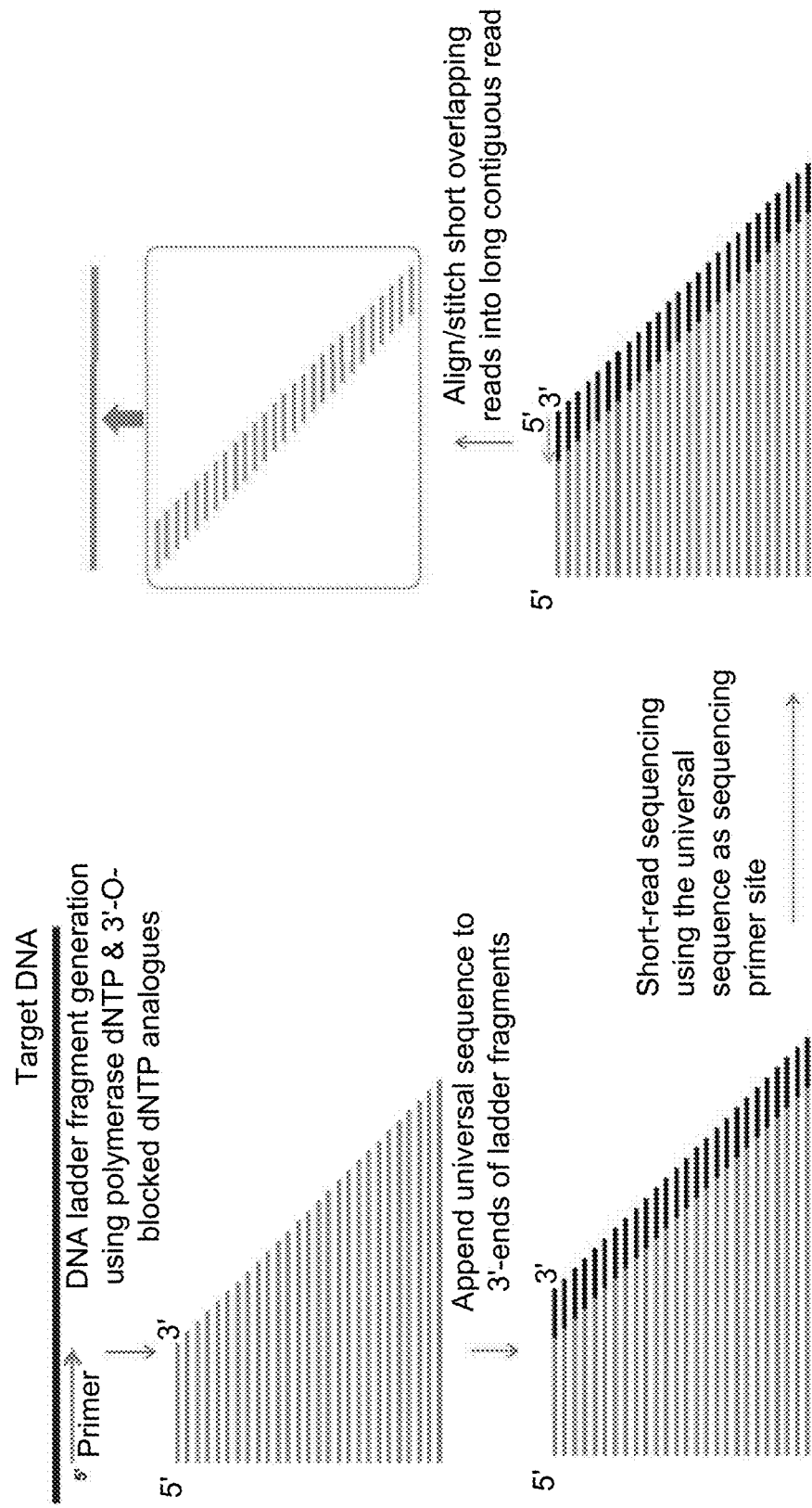
FIG. 1 is a schematic depicting an embodiment of the technology for sequencing a nucleic acid.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The technology generally relates to obtaining a nucleotide sequence, such as a consensus sequence or a haplotype sequence. In some embodiments provided herein is technology to produce a library of short overlapping DNA fragments from a larger target DNA fragment to be sequenced. The short overlapping DNA fragments have a range of lengths such that one fragment differs from another fragment by 1-5 bases, preferably 1 base, at their 3' ends (e.g., a fragment ladder similar to that produced by conventional Sanger sequencing methods). In some embodiments, the short overlapping DNA fragments are indexed to generate a next generation sequencing (NGS) library. The library finds use in performing NGS by initiating sequencing reactions from the varying 3' ends of the DNA fragments. Acquiring ~30-base to ~50-base sequence reads from the 3' ends of the short overlapping fragments produces a tiled set of ~30-base to ~50-base sequence reads spanning the larger target DNA to be sequenced and offset from one another by 1-5 bases, preferably offset by 1 base. Assembling the overlapping ~30-50 bp short sequence reads produces a long contiguous read covering a larger region (~800-1000 bp) of the target DNA fragment. Thus, each sequence read results from the highest quality bases produced by NGS (e.g., the first 20-100 bases) and each base of the assembly is the consensus of 30-50 independent high quality sequence reads.

In the description of this technology, the section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleotide" comprises a "base" (alternatively, a "nucleobase" or "nitrogenous base"), a "sugar" (in particular, a five-carbon sugar, e.g., ribose or 2-deoxyribose), and a "phosphate moiety" of one or more phosphate groups (e.g., a monophosphate, a diphosphate, or a triphosphate consisting of one, two, or three linked phosphates, respectively). Without the phosphate moiety, the nucleobase and the sugar compose a "nucleoside". A nucleotide can thus also be called a nucleoside monophosphate or a nucleoside diphosphate or a nucleoside triphosphate, depending on the number of phosphate groups attached. The phosphate moiety is usually attached to the 5-carbon of the sugar, though some nucleotides comprise phosphate moieties attached to the 2-carbon or the 3-carbon of the sugar. Nucleotides contain either a purine (in the nucleotides adenine and guanine) or a pyrimidine base (in the nucleotides cytosine, thymine, and uracil). Ribonucleotides are nucleotides in which the sugar is ribose. Deoxyribonucleotides are nucleotides in which the sugar is deoxyribose.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of a reverse transcriptase.

As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases (e.g., adenine, guanine, cytosine, and thymine/uracil) in a molecule (e.g., a whole genome, a whole transcriptome, an exome, oligonucleotide, polynucleotide, fragment, etc.) of DNA or RNA.

It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Reference to a base, a nucleotide, or to another molecule may be in the singular or plural. That is, "a base" may refer to a single molecule of that base or to a plurality of the base, e.g., in a solution.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the term "target nucleic acid" or "target nucleotide sequence" refers to any nucleotide sequence (e.g., RNA or DNA), the manipulation of which may be deemed desirable for any reason by one of ordinary skill in the art. In some contexts, "target nucleic acid" refers to a nucleotide sequence whose nucleotide sequence is to be determined or is desired to be determined. In some contexts, the term "target nucleotide sequence" refers to a sequence to which a partially or completely complementary primer or probe is generated.

As used herein, the term "region of interest" refers to a nucleic acid that is analyzed (e.g., using one of the compositions, systems, or methods described herein). In some embodiments, the region of interest is a portion of a genome or region of genomic DNA (e.g., comprising one or chromosomes or one or more genes). In some embodiments, mRNA expressed from a region of interest is analyzed.

As used herein, the term "corresponds to" or "corresponding" is used in reference to a contiguous nucleic acid or nucleotide sequence (e.g., a subsequence) that is complementary to, and thus "corresponds to", all or a portion of a target nucleic acid sequence.

As used herein, the phrase "a clonal plurality of nucleic acids" refers to the nucleic acid products that are complete or partial copies of a template nucleic acid from which they were generated. These products are substantially or completely or essentially identical to each other, and they are complementary copies of the template nucleic acid strand from which they are synthesized, assuming that the rate of nucleotide misincorporation during the synthesis of the clonal nucleic acid molecules is 0%.

As used herein, the term "library" refers to a plurality of nucleic acids, e.g., a plurality of different nucleic acids.

As used herein, a "subsequence" of a nucleotide sequence refers to any nucleotide sequence contained within the nucleotide sequence, including any subsequence having a size of a single base up to a subsequence that is one base shorter than the nucleotide sequence.

As used herein, the term "consensus sequence" refers to a sequence that is common to, or otherwise present in the largest fraction, of an aligned group of sequences. The consensus sequence shows the nucleotide most commonly found at each position within the nucleic acid sequences of the group of sequences. A consensus sequence is often "assembled" from shorter sequence reads.

As used herein, "assembly" refers to generating nucleotide sequence information from shorter sequences, e.g., experimentally acquired sequence reads. Sequence assembly can generally be divided into two broad categories: de novo assembly and reference genome mapping assembly. In de novo assembly, sequence reads are assembled together so that they form a new and previously unknown sequence. In reference genome "mapping", sequence reads are assembled against an existing "reference sequence" to build a sequence that is similar to but not necessarily identical to the reference sequence.

The phrase "sequencing run" refers to any step or portion of a sequencing experiment performed to determine some information relating to at least one biomolecule (e.g., nucleic acid molecule).

As used herein, the phrase "dNTP" means deoxynucleotidetriphosphate, where the nucleotide comprises a nucleotide base, such as A, T, C, G or U.

The term "monomer" as used herein means any compound that can be incorporated into a growing molecular chain by a given polymerase. Such monomers include, without limitations, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors or any other molecule that can be incorporated into a growing polymer chain by a given polymerase.

As used herein, "complementary" generally refers to specific nucleotide duplexing to form canonical Watson-Crick base pairs, as is understood by those skilled in the art. However, complementary also includes base-pairing of nucleotide analogs that are capable of universal base-pairing with A, T, G or C nucleotides and locked nucleic acids that enhance the thermal stability of duplexes. One skilled in the art will recognize that hybridization stringency is a determinant in the degree of match or mismatch in the duplex formed by hybridization.

A "polymerase" is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* (Taq) DNA polymerase, *Thermus thermophilus* (Tth) DNA polymerase, Vent DNA polymerase (New England Biolabs), Deep Vent DNA polymerase (New England Biolabs), *Bacillus stearothermophilus* (Bst) DNA polymerase, DNA Polymerase Large Fragment, Stoeffel Fragment, 9°N DNA Polymerase, 9°Nm polymerase, *Pyrococcus furiosis* (Pfu) DNA Polymerase, *Thermus filiformis* (Tfi) DNA Polymerase, RepliPHI Phi29

Polymerase, *Thermococcus litoralis* (Tli) DNA polymerase, eukaryotic DNA polymerase beta, telomerase, Therminator (e.g., THERMINATOR I, THERMINATOR II, etc.) polymerase (New England Biolabs), KOD HiFi. DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting and/or molecular evolution, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants such as exo⁻ polymerases; polymerases with minimized, undetectable, and/or decreased 3'→5' proofreading exonuclease activity, and other mutants, e.g., that tolerate labeled nucleotides and incorporate them into a strand of nucleic acid. In some embodiments, the polymerase is designed for use, e.g., in real-time PCR, high fidelity PCR, next-generation DNA sequencing, fast PCR, hot start PCR, crude sample PCR, robust PCR, and/or molecular diagnostics. Such enzymes are available from many commercial suppliers, e.g., Kapa Enzymes, Finnzymes, Promega, Invitrogen, Life Technologies, Thermo Scientific, Qiagen, Roche, etc.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, an "adaptor" is an oligonucleotide that is linked or is designed to be linked to a nucleic acid to introduce the nucleic acid into a sequencing workflow. An adaptor may be single-stranded or double-stranded (e.g., a double-stranded DNA or a single-stranded DNA). As used herein, the term "adaptor" refers to the adaptor nucleic in a state that is not linked to another nucleic acid and in a state that is linked to a nucleic acid.

At least a portion of the adaptor comprises a known sequence. For example, some embodiments of adaptors comprise a primer binding sequence for amplification of the nucleic acid and/or for binding of a sequencing primer. Some adaptors comprise a sequence for hybridization of a complementary capture probe. Some adaptors comprise a chemical or other moiety (e.g., a biotin moiety) for capture and/or immobilization to a solid support (e.g., comprising an avidin moiety). Some embodiments of adaptors comprise a marker, index, barcode, tag, or other sequence by which the adaptor and a nucleic acid to which it is linked are identifable.

Some adaptors comprise a universal sequence. A universal sequence is a sequence shared by a plurality of adaptors that may otherwise have different sequences outside of the universal sequence. For example, a universal sequence provides a common primer binding site for a collection of nucleic acids from different target nucleic acids, e.g., that may comprise different barcodes.

Some embodiments of adaptors comprise a defined but unknown sequence. For example, some embodiments of adaptors comprise a degenerate sequence of a defined number of bases (e.g., a 1- to 20-base degenerate sequence). Such a sequence is defined even if each individual sequence is not known—such a sequence may nevertheless serve as an index, barcode, tag, etc. marking nucleic acid fragments from, e.g., the same target nucleic acid.

Some adaptors comprise a blunt end and some adaptors comprise an end with an overhang of one or more bases.

In particular embodiments provided herein, an adaptor comprises an azido moiety, e.g., the adaptor comprises an azido (e.g., an azido-methyl) moiety on its 5' end. Thus, some embodiments are related to adaptors that are or that comprise a 5'-azido-modified oligonucleotide or a 5'-azido-methyl-modified oligonucleotide.

As used herein, a "system" denotes a set of components, real or abstract, comprising a whole where each component interacts with or is related to at least one other component within the whole.

As used herein, "index" shall generally mean a distinctive or identifying mark or characteristic. One example of an index is a short nucleotide sequence used as a "barcode" to identify a longer nucleotide comprising the barcode and other sequence.

As used herein, the term "phase" or "phasing" refers to the unique content of the two chromosomes inherited from each parent and/or separating maternally and paternally derived sequence information present on a nucleic acid (e.g., a chromosome) For example, haploytpe phasing information describes which nucleotides (e.g., a SNP), regions, portions, or fragments originated from each of the parental chromosomes (or are associated with a specific minor viral quasi-species).

As used herein a "Sanger ladder", "DNA ladder", "fragment ladder", or "ladder" refers to a library of nucleic acids (e.g., DNA) that each differ in length by a small number of bases, e.g., one to five bases and in some preferred embodiments by one base. In some embodiments, the nucleic acids in the ladder have 5' ends that correspond to the same nucleotide position (or fall within a small range of nucleotide positions, e.g., 1-10 nucleotide positions) in the template from which they were made and have different 3' ends that correspond to a range of nucleotide positions in the template from which they were made. See, e.g., exemplary ladders and/or ladders similar to those provided herein in Sanger & Coulson (1975) "A rapid method for determining sequences in DNA by primed synthesis with DNA polymerase" *J Mol Biol* 194(3):441-8; Sanger et al (1977) "DNA sequencing with chain-terminating inhibitors" *Proc Natl Acad Sci USA* 74 (12): 5463-7.

DESCRIPTION

In some embodiments, the technology provided herein provides methods and compositions to create short overlapping DNA fragments that span over a larger region of DNA fragment. In particular, the short DNA fragments compose a population of DNA fragments having a range of sizes that increase in size from one fragment to the next larger fragment by, for example, 1 to 20 base pairs, 1 to 10 base pairs, or 1 to 5 base pairs, preferably by 1 base pair (e.g., as in the case of fragments generated by Sanger sequencing). In some embodiments, a short nucleic acid having a universal sequence is appended to the 3' ends of each fragment (e.g., the end of the fragment where the ladder is generated). Subsequently, the fragments are sequenced using a sequencing primer complementary to the universal sequence. As such, the sequences generated have a range of 5' (first) bases corresponding to bases distributed along the length of the larger DNA from the first base attached to the universal sequence up to 500 bases or more. Preferably, the sequences generated have a range of 5' (first) bases corresponding to each base distributed along the length of the larger DNA. With this method, short NGS reads (~30 to ~50 bases) are used to assemble a long contiguous read that retains phase and/or linkage information (see, e.g., FIG. 1).

1. Methods of Producing Libraries for NGS

Figure 2A:
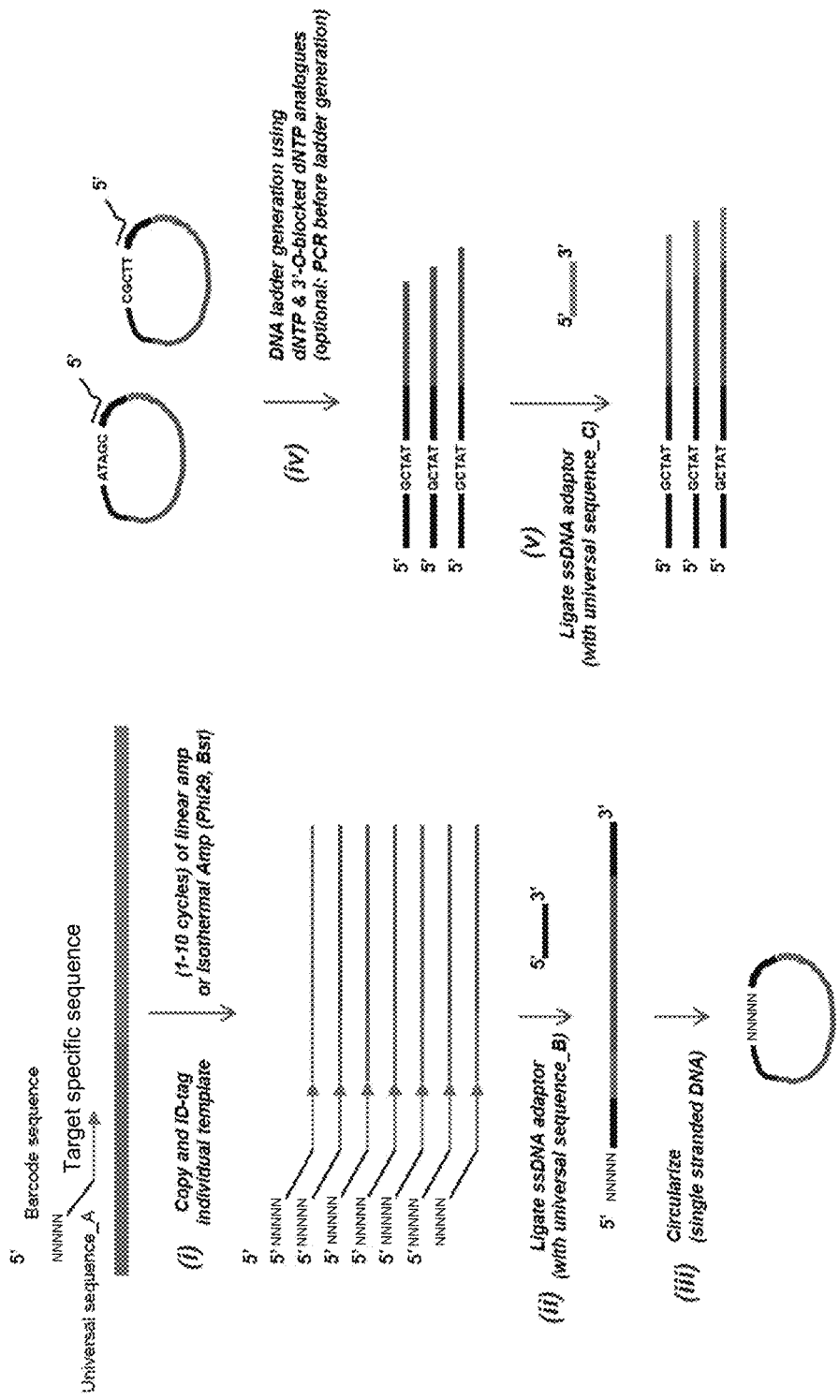
FIG. 2A shows one embodiment of the technology and FIG. 2B shows another embodiment of the technology.

Embodiments of the technology are depicted by the schematic shown in FIG. 2. First, in some embodiments, a target nucleic acid is amplified using one or more target specific primers (see, e.g., FIG. 2A, step i; FIG. 2C, step i). The target nucleic acid may be a DNA or an RNA, e.g., a genomic DNA; mRNA; a cosmid, fosmid, or bacterial artificial chromosome (e.g., comprising an insert), a gene, a plasmid, etc. In some embodiments, an RNA is first reverse transcribed to produce a DNA. Amplification may be PCR, limited cycle (low cycle, e.g., 5-15 cycles (e.g., 8 cycles)) PCR, isothermal PCR, amplification with Phi29 or Bst enzymes, etc., e.g., as shown in FIG. 2A and in FIG. 2C.

In some embodiments, the target specific primers include both a universal sequence (e.g., universal sequence A) and a uniquely identifying index sequence (e.g., a barcode sequence; see FIG. 2A, "NNNNN" barcode sequence) that allows tracking and/or identifying the target nucleic acid from which the amplified product (amplicon) was produced. Generally, barcode sequences may consist of 1 to 10 or more nucleotides. For example, a 10-base barcode sequence provides 1,048,576 ($4^{10}$) combinations of uniquely identifiable target-specific primer molecules. Consequently, with an appropriately designed barcode length, a starting material containing a small to a very large number of target DNA fragments can be reliably tagged and indexed without duplicate tagging with the same barcode sequence.

Figure 9:
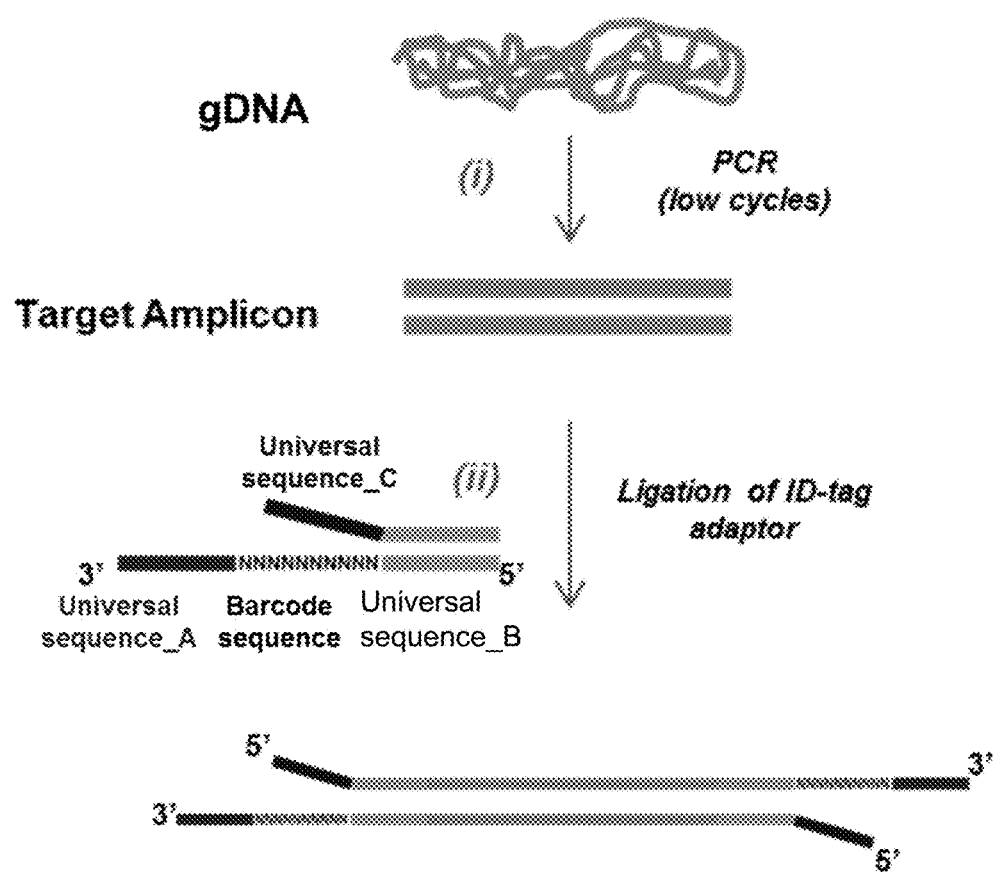
FIG. 9 shows a scheme for an adaptor ligation based molecular barcoding strategy according to particular embodiments of the technology.

In some embodiments, the primers are used for amplification (e.g., do not comprise a barcode) and the target amplicon is ligated to an adaptor that comprises one or more universal sequences and/or one or more barcode sequences (see, e.g., FIG. 2C, "NNNNNNNNNN" barcode sequence, step ii). Thus, in some embodiments a next step comprises ligating an adaptor to the target amplicon. In some embodiments, the adaptor comprises first strand comprising a stretch of degenerate sequence (e.g., comprising 8 to 12 bases) flanked on both the 5' end and the 3' end by two different universal sequences (e.g., universal sequence A and universal sequence B; see FIG. 9) and a second strand comprising a universal sequence C (e.g., at the 5' end) and a sequence (e.g., at the 3' end) that is complementary to universal sequence B and that has an additional T at the 3'-terminal position.

Embodiments are provided herein for producing a fragment ladder from a circularized template (see, e.g., FIG. 2A and FIG. 2B) and embodiments are provided herein for producing a fragment ladder from a linear template (see, e.g., FIG. 2C). Accordingly, in some embodiments, a next step comprises ligating the uniquely barcoded individual amplicons at their 3' ends to an adaptor oligonucleotide approximately 10 to 80 bases in length and comprising a second universal sequence (e.g., universal sequence B) (see, e.g., FIG. 2A, step iv). After ligation, the adaptor-amplicon nucleic acids are self-ligated (e.g., circularized) to form a circular template (see, e.g., FIG. 2A, step iii). The circularization brings the universal sequence at the 3' end adjacent to the barcode sequence at the 5' end. Intramolecular ligation may be effected using a ligase. For example, CircLigase II (Epicentre) is a thermostable single-stranded DNA ligase that catalyzes intramolecular ligation of single-stranded DNA templates having a 5' phosphate and a 3' hydroxyl group.

Then, in embodiments related to using a circularized template, a Sanger fragment-like DNA ladder is generated by a polymerase reaction using a primer complementary to universal sequence A and a mix of dNTPs and 3'-O-blocked dNTP analogs as described herein (see, e.g., FIG. 2A, step iv). In some embodiments, the 3'-O-blocked dNTP analog is a 3'-O-alkynyl nucleotide analog (e.g., an alkyl, having a saturated position ($sp^3$-hybridized) on a molecular framework next to an alkynyl group, and substituted variants thereof). In some embodiments, the 3'-O-blocked dNTP analog is a 3'-O-propargyl nucleotide analog having a structure as shown below:

where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.) and P comprises a phosphate moiety. In some embodiments, P comprises a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate. Other alkynyl groups are contemplated by the technology and find use in the technology, e.g., butynyl, etc. In some embodiments, the nucleotide analog is as described in other sections herein.

Alternatively, in embodiments related to the use of a linear template (see, e.g., FIG. 2C), a Sanger fragment-like DNA ladder is generated by a polymerase reaction using a primer complementary to a sequence in the adaptor and a mix of dNTPs and 3'-O-blocked dNTP analogs as described herein (see, e.g., FIG. 2C, step iii). In some embodiments, the 3'-O-blocked dNTP analog is a 3'-O-alkynyl nucleotide analog (e.g., an alkyl having a saturated position (spa-hybridized) on a molecular framework next to an alkynyl group, and substituted variants thereof). In some embodiments, the 3'-O-blocked dNTP analog is a 3'-O-propargyl nucleotide analog having a structure as shown below:

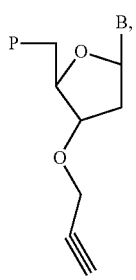

where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.) and P comprises a phosphate moiety. In some embodiments, P comprises a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate. Other alkynyl groups are contemplated by the technology and find use in the technology, e.g., butynyl, etc. In some embodiments, the nucleotide analog is as described in other sections herein.

Embodiments of the technology provide advantages over existing technologies. For example, in some embodiments the technology provides high quality sequence from a small amount of input nucleic acid (e.g., less than 10 ng of nucleic acid, e.g., less than 10 ng of genomic DNA). The technology provides for the robust tagging of individual templates. Production of libraries is efficient because the methods comprise few manipulations (and thus few clean-up steps) and each of the manipulations has a sufficient yield.

In some embodiments, the nucleotide analog comprises a reversible terminator that comprises a blocking group that can be removed to unblock the nucleotide. In some embodiments, the nucleotide analog comprises a functional terminator, e.g., that provides a particular desired reactivity for subsequent steps.

The nucleotide analogs result in the production of a fragment ladder having fragments over a range of sizes. For example, in some embodiments, the fragments have lengths ranging from approximately 10 to approximately 50 bp, approximately 10 to approximately 100 bp, and up to approximately 100 bp to approximately 700 or approximately 800 bp or more bp; furthermore, in some embodiments lengths greater than 1000 bp are achieved by adjusting the ratio of dNTPs and 3'-O-blocked dNTP analogs in the reaction mixture (e.g., using a ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1).

Conventional dideoxynucleotide (ddNTP) sequencing technologies (e.g., Sanger-type sequencing chemistries) are not appropriate for this step in these embodiments because the lack of a 3'-OH group in the terminating ddNTP creates a non-reactive terminal 3' end that cannot accept the ligation of the second adaptor oligonucleotide in the subsequent step.

Once the nucleic acid fragment ladder is generated with reactive (e.g., ligatable) 3' ends, a second adaptor oligonucleotide comprising a universal sequence (e.g., universal sequence C) is ligated (enzymatically or chemically) to the 3' ends of the fragments of the nucleic acid fragment ladder to produce a NGS library. (see, e.g., FIG. 2A, step v; FIG. 2C, step (iv)). In some embodiments, limited cycle PCR or another amplification method is performed to amplify the final product.

In some embodiments, the methods find use in acquiring short sequences, e.g., of ~420-200 bp. Such embodiments find use, e.g., in assessing cancer genes, e.g., to assess mutations of a cancer panel. In some embodiments, the technology finds use in acquiring sequences of 500 bp, 1000 bp, or more. For example, in some embodiments, a target nucleic acid is amplified using one or more target specific primers (see, e.g., FIG. 2B, step i; FIG. 2C, step (i)). The target nucleic acid may be a DNA or an RNA, e.g., a genomic DNA; mRNA; a cosmid, fosmid, or bacterial artificial chromosome (e.g., comprising an insert), a gene, a plasmid, etc. In some embodiments, an RNA is first reverse transcribed to produce a DNA. Amplification may be PCR, limited cycle PCR, isothermal PCR, amplification with Phi29 or Bst enzymes, etc., e.g., as shown in FIG. 2B and in FIG. 2C.

In some embodiments, the target specific primers include both a universal sequence (e.g., universal sequence A) and a uniquely identifying index sequence (e.g., a barcode sequence; see FIG. 2B, "NNNNN" barcode sequence) that allows tracking and/or identifying the target nucleic acid from which the amplified product (amplicon) was produced. Generally, barcode sequences may consist of 1 to 10 or more nucleotides. For example, a 10-base barcode sequence provides 1,048,576 ($4^{10}$) combinations of uniquely identifiable target-specific primer molecules. Consequently, with an appropriately designed barcode length, a starting material containing a small to a very large number of target DNA fragments can be reliably tagged and indexed without duplicate tagging with the same barcode sequence.

Figure 2B:
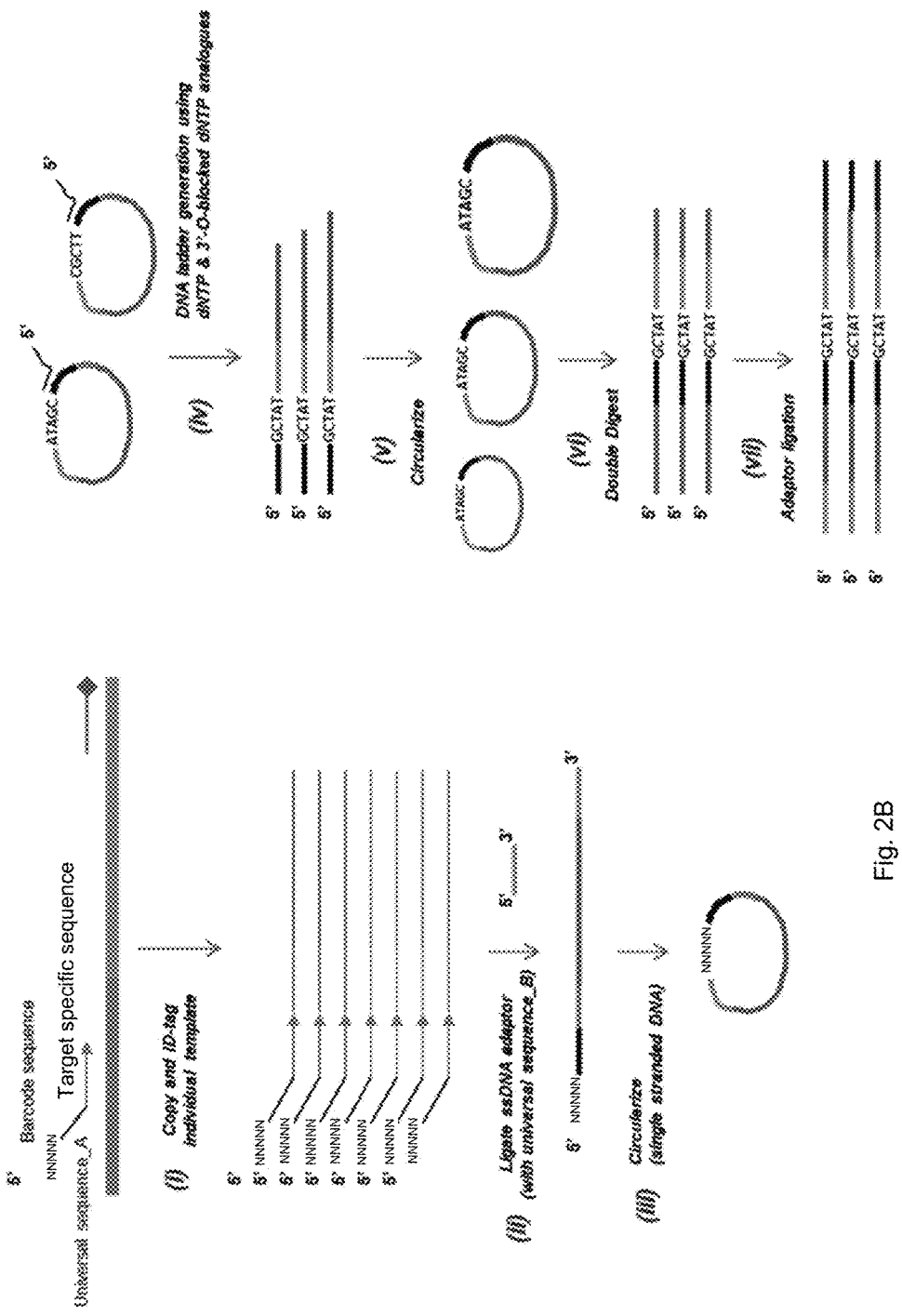

In some embodiments, a next step comprises ligating the uniquely barcoded individual amplicons at their 3' ends to an adaptor oligonucleotide approximately 10 to 80 bases in length and comprising a second universal sequence (e.g., universal sequence B) (see, e.g., FIG. 2B, step ii). After ligation, the adaptor-amplicon nucleic acids are self-ligated (e.g., circularized) to form a circular template (see, e.g., FIG. 2B, step iii). The circularization brings the universal sequence at the 3' end adjacent to the barcode sequence at the 5' end. Intramolecular ligation may be effected using a ligase. For example, CircLigase II (Epicentre) is a thermostable single-stranded DNA ligase that catalyzes intramolecular ligation of single-stranded DNA templates having a 5' phosphate and a 3' hydroxyl group.

Using the circularized template, a Sanger fragment-like DNA ladder is generated by a polymerase reaction using a primer complementary to universal sequence A and a mix of dNTPs and 3'-O-blocked dNTP analogs as described herein (see, e.g., FIG. 2B, step iv). In some embodiments, the 3'-O-blocked dNTP analog is a 3'-O-alkynyl nucleotide analog (e.g., an alkyl, having a saturated position (spa-hybridized) on a molecular framework next to an alkynyl group, and substituted variants thereof). In some embodiments, the 3'-O-blocked dNTP analog is a 3'-O-propargyl nucleotide analog having a structure as shown below:

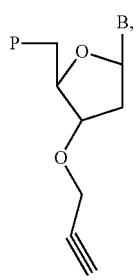

where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.) and P comprises a phosphate moiety. In some embodiments, P comprises a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate. Other alkynyl groups are contemplated by the technology and find use in the technology, e.g., butynyl, etc. In some embodiments, the nucleotide analog is as described in other sections herein. Other alkynyl groups are contemplated by the technology and find use in the technology, e.g., butynyl, etc. In some embodiments, the nucleotide analog is as described in other sections herein.

In some embodiments, the nucleotide analog comprises a reversible terminator that comprises a blocking group that can be removed to unblock the nucleotide. In some embodiments, the nucleotide analog comprises a functional terminator, e.g., that provides a particular desired reactivity for subsequent steps. The nucleotide analogs result in the production of a fragment ladder having fragments over a range of sizes. For example, in some embodiments, the fragments have lengths ranging from ~100 bp to ~700 or 800 bp; furthermore, in some embodiments, sequence lengths greater than 1000 bp to greater than 10,000 bp are achieved, e.g., by adjusting the ratio of dNTPs and 3'-O-blocked dNTP analogs in the reaction mixture.

Conventional dideoxynucleotide (ddNTP) sequencing technologies (e.g., Sanger-type sequencing chemistries) are not appropriate for this step in these embodiments because the lack of a 3'-OH group in the terminating ddNTP creates a non-reactive terminal 3' end that cannot accept the ligation of the second adaptor oligonucleotide in the subsequent step.

Then, the nucleic acid fragment ladder is circularized to form a nucleic acid circle library (see, e.g., FIG. 2B, step v). After a digestion with one or more restriction enzymes (see, e.g., FIG. 2B, step vi), a second adaptor oligonucleotide (e.g., comprising a universal sequence, e.g., universal sequence C) is ligated (enzymatically or chemically) to the 3' ends of the digestion products of the nucleic acid circle library to produce a NGS library. (see, e.g., FIG. 2B, step vii). In some embodiments, limited cycle PCR or another amplification method is performed to amplify the final product. Without being limited to any particular method or length of time to perform any steps of the methods provided, in some embodiments the methods described take from ~6 (e.g., ~6.5) hours to ~9 (e.g., ~8.5) hours to complete.

In some embodiments (e.g., embodiments using 3'-O-alkynyl nucleotide analog terminators such as 3'-O-propargyl nucleotide analogs), the fragments comprise a 3' alkyne. Then, in some embodiments, the second adaptor oligonucleotide comprising a universal sequence (e.g., universal sequence C) comprises a 5' azide ($N_3$) group that is reactable with the fragment 3' alkyne group. Then, in some embodiments, a "click chemistry" process such as an azide-alkyne cycloaddition is used to link the adaptor to the fragment via formation of a triazole

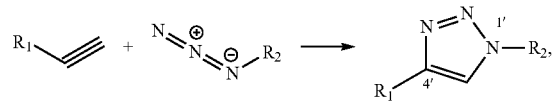

where $R_1$ and $R_2$ are individually any chemical structure or chemical moiety.

In some embodiments, the triazole ring linkage has a structure according to:

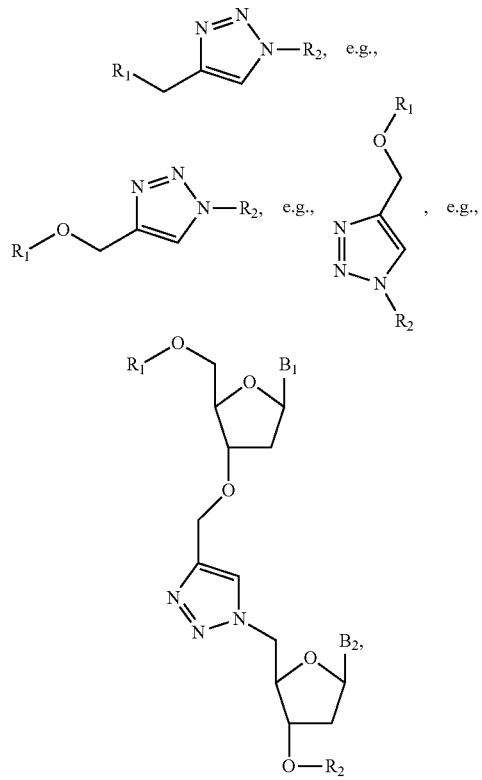

where $R_1$ and $R_2$ are individually any chemical structure or chemical moiety (and not necessarily the same from structure to structure) and B, $B_1$, and $B_2$ individually indicate the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

The triazole ring linkage formed by the alkyne-azide cycloaddition has similar characteristics (e.g., physical, biological, chemical characteristics) as a natural phosphodiester bond present in nucleic acids and therefore is a nucleic acid backbone mimic. Consequently, conventional enzymes that recognize natural nucleic acids as substrates also recognize as substrates the products formed by alkyne-azide cycloaddition as provided by the technology described herein. See, e.g., El-Sagheer, et al. (2011) "Biocompatible artificial DNA linker that is read through by DNA polymerases and is functional in *Escherichia coli*" *Proc Natl Acad Sci USA* 108 (28): 11338-43, which is incorporated herein by reference in its entirety).

Figure 3:
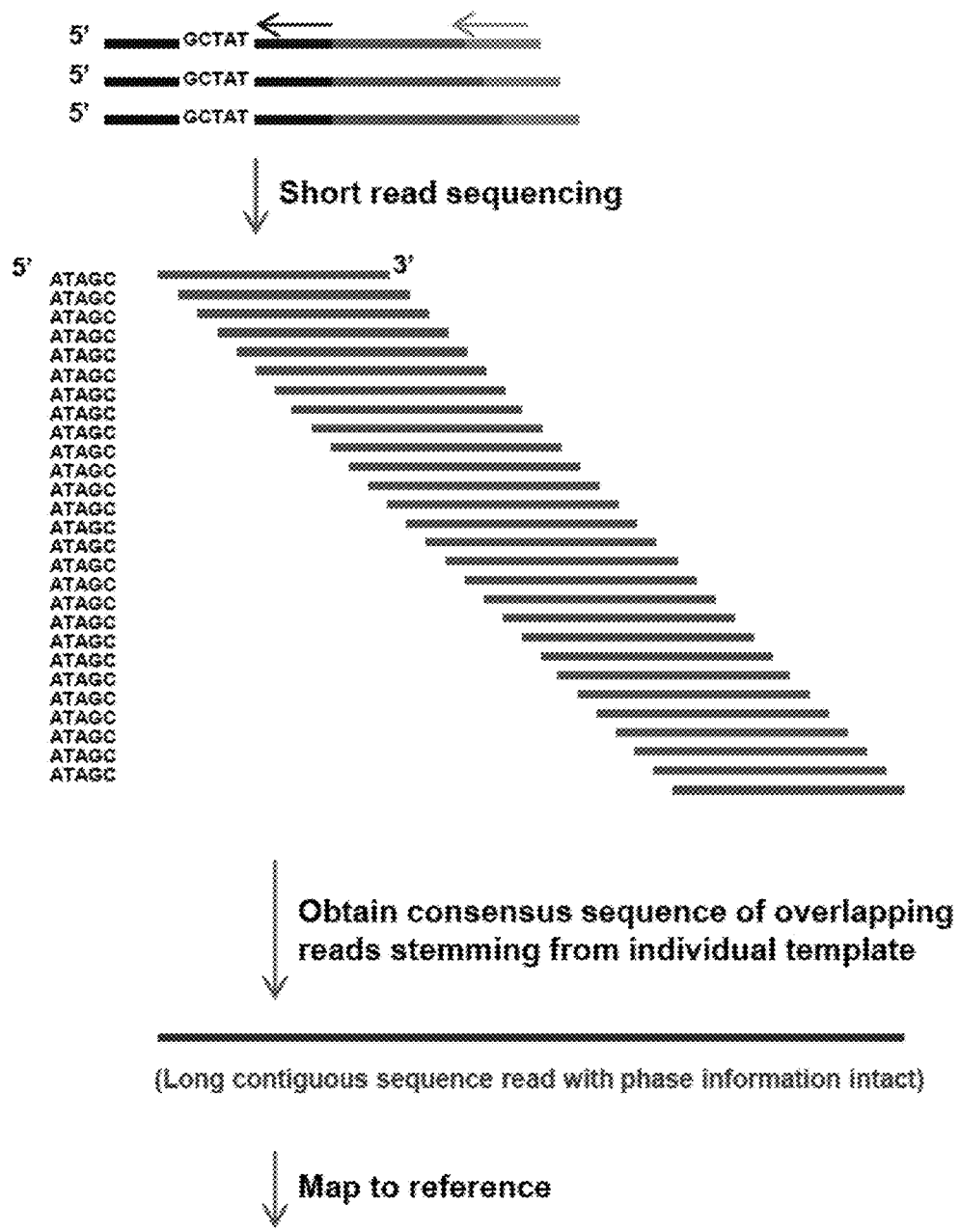
FIG. 3 is a schematic depicting an embodiment of the technology for sequencing a nucleic acid.
Figure 4A:
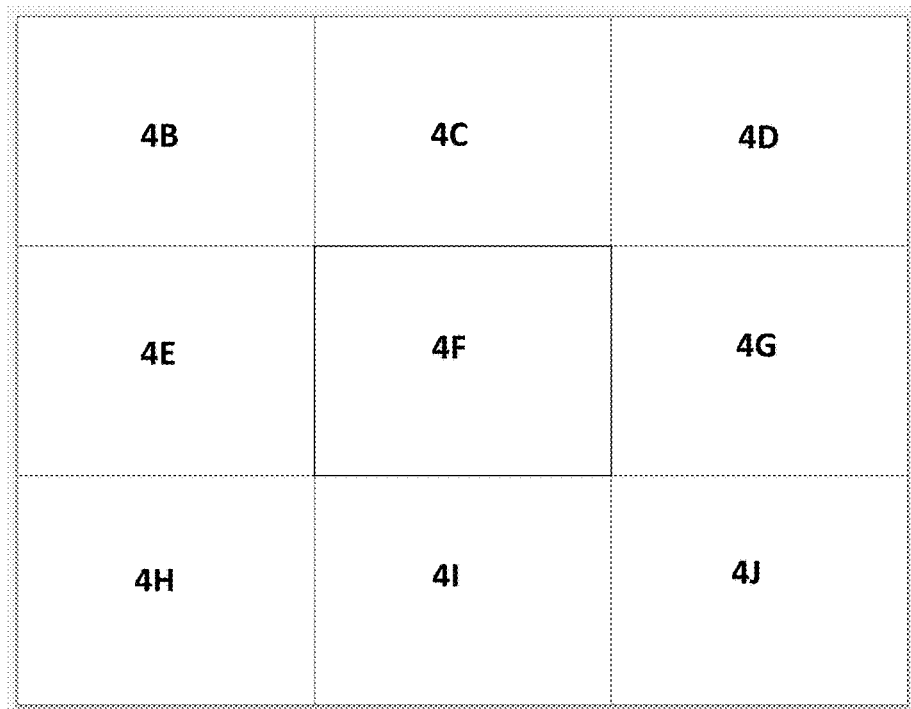
Figure 4B:
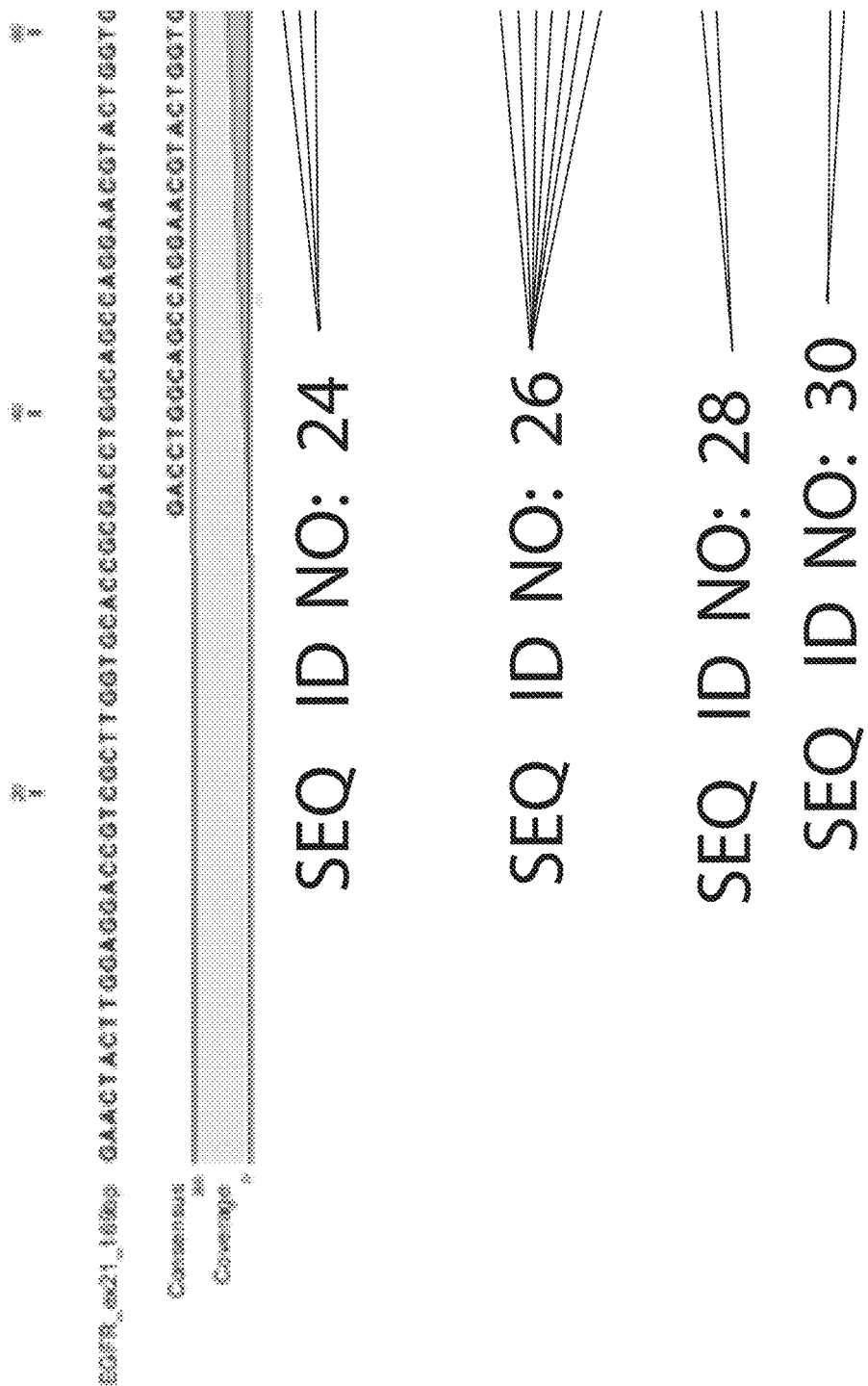
Figure 4C:
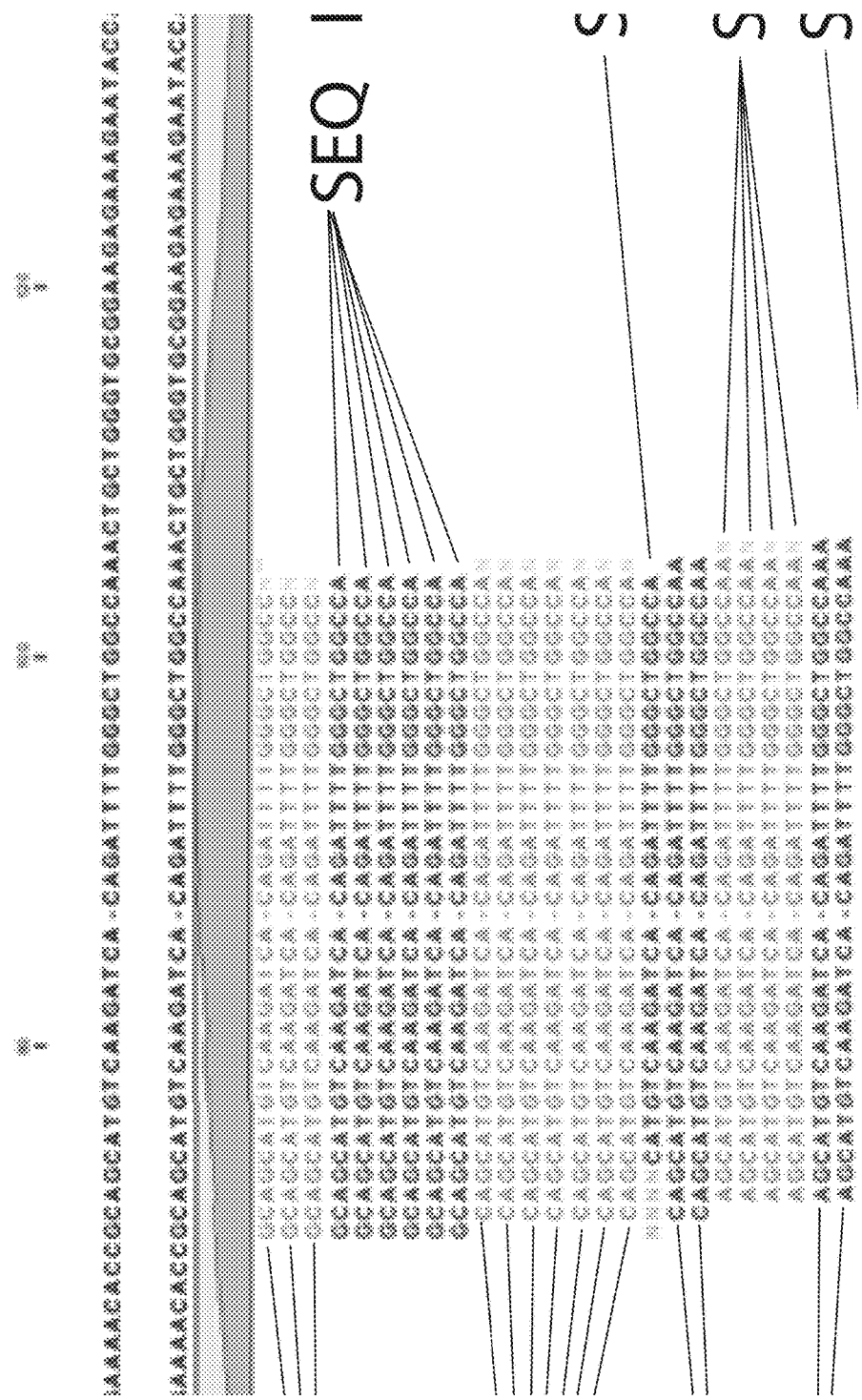
Figure 4D:
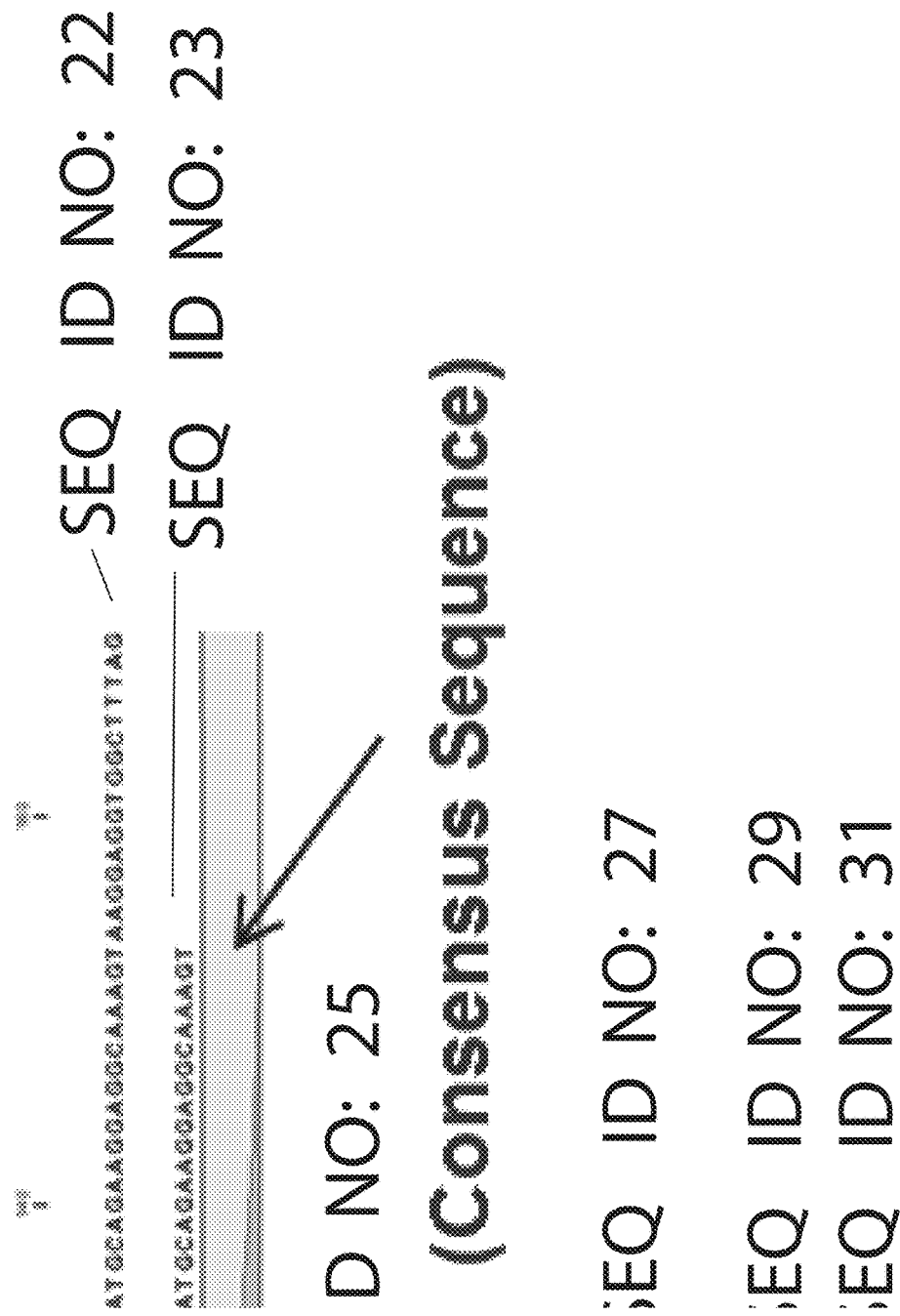
Figure 4F:
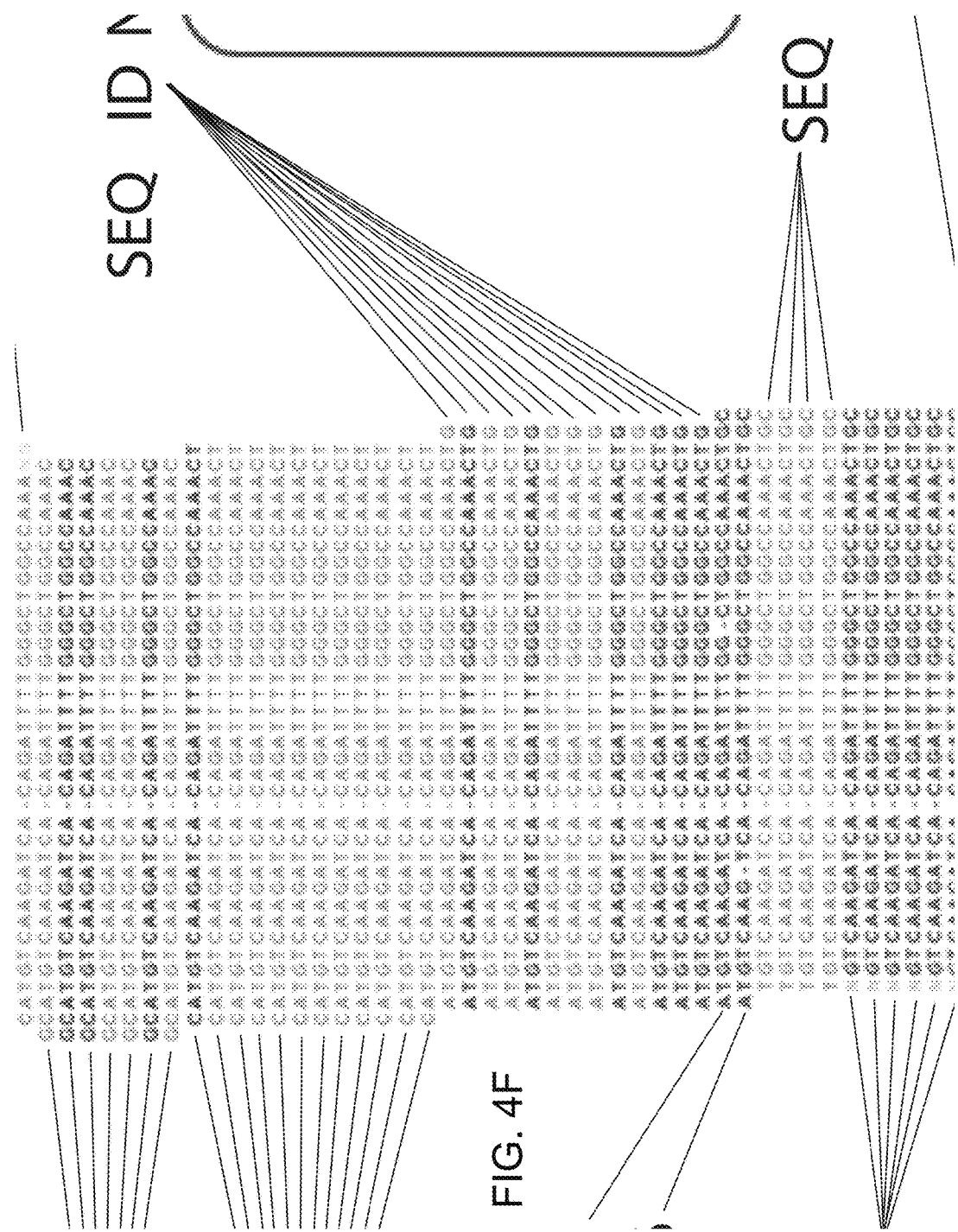
Figure 4I:
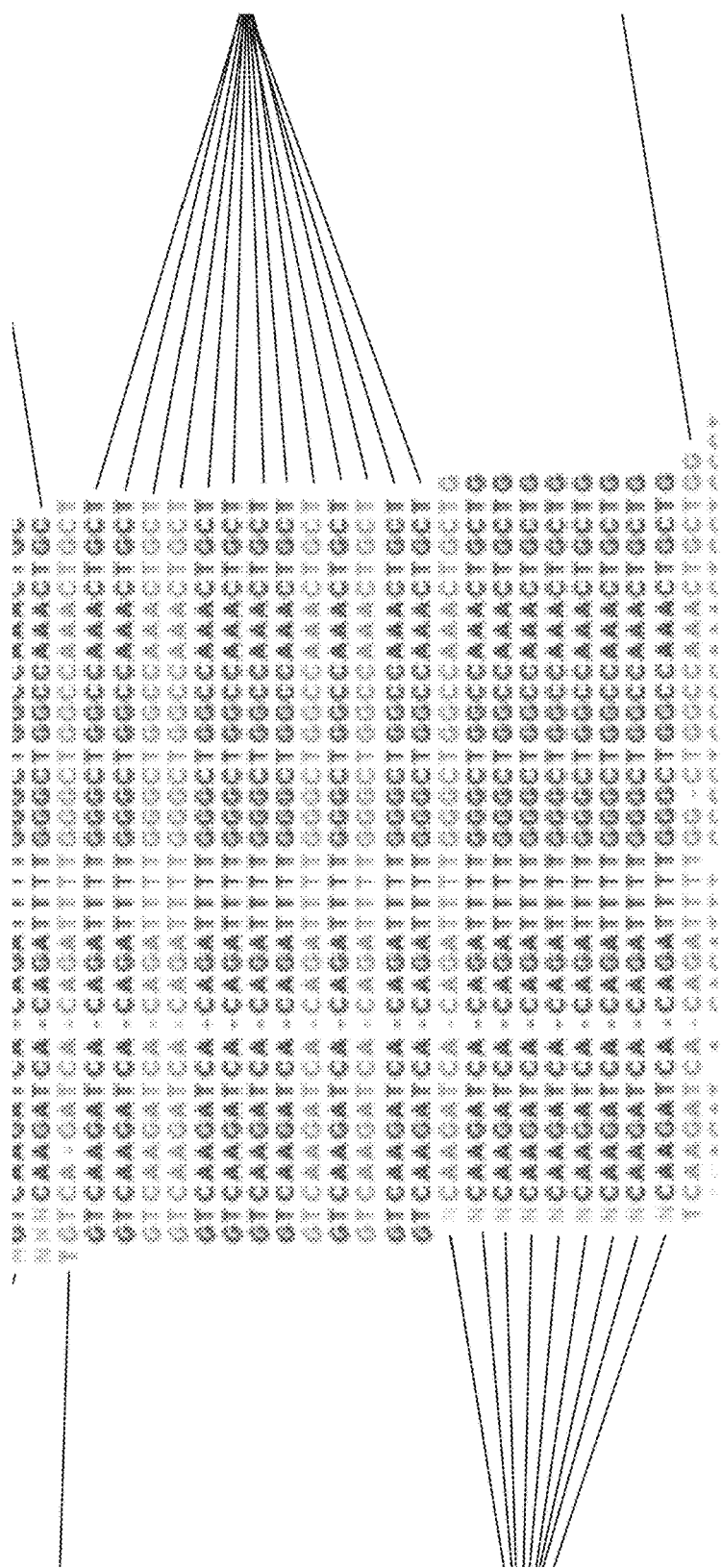

The final NGS fragment library is then used as the input to a NGS system for sequencing. During sequencing, ~20 to 50 bases of DNA adjacent to the adaptor comprising universal sequence C are sequenced (corresponding to ~20 to 50 bases of the target nucleic acid) and the barcode adjacent to the adaptor comprising universal sequence B is sequenced (see, e.g., FIG. 3). Once the sequences are obtained, the sequence reads are parsed into bins by the barcode sequences to collect sequence reads that originated from a template molecule tagged with that particular unique barcode sequence (see, e.g., FIG. 3). The sequence reads in each bin (for each barcode sequence) are aligned to each other and assembled to construct a longer contiguous consensus sequence with phase information intact. This sequence can be aligned to an appropriate reference sequence for downstream sequence analysis.

Various exemplary nucleic acid sequencing platforms, nucleic acid assembly, and/or nucleic acid mapping systems (e.g., computer software and/or hardware) are described, e.g., in U.S. Pat. Appl. Pub. No. 2011/0270533, which is incorporated herein by reference. The techniques of "paired-end", "mate-pair", and other assembly-related sequencing are generally known in the art of molecular biology (Siegel A. F. et al., *Genomics* 2000, 68: 237-246; Roach J. C. et al., *Genomics* 1995, 26: 345-353). These sequencing techniques allow the determination of multiple "reads" of sequence, each from a different place on a single polynucleotide. Typically, the distance between the reads or other information regarding a relationship between the reads is known. In some situations, these sequencing techniques provide more information than does sequencing multiple stretches of nucleic acid sequences in a random fashion. With the use of appropriate software tools for the assembly of sequence information (e.g., Millikin S. C. et al., Genome Res. 2003, 13: 81-90; Kent, W. J. et al., Genome Res. 2001, 11: 1541-8) it is possible to make use of the knowledge that the sequences are not completely random, but are known to occur a known distance apart and/or to have some other relationship, and are therefore linked in the genome. This information can aid in the assembly of whole nucleic acid sequences into a consensus sequence.

2. Nucleotide Analogs

In some embodiments a nucleotide analog finds use as a functional nucleotide terminator (e.g., in embodiments of compositions, methods, kits, and systems described herein). A functional nucleotide terminator both terminates polymerization of a nucleic acid, e.g., by blocking the 3' hydroxyl from participating further in the polymerization reaction, and comprises a functional reactive group that can participate in other chemical reactions with other chemical moieties and groups.

For example, a nucleotide analog comprising an alkynyl group finds use in some embodiments, e.g., having a structure according to:

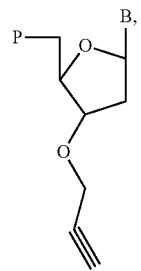

wherein B is a base, e.g., adenine, guanine, cytosine, thymine, or uracil, e.g., having a structure according to:

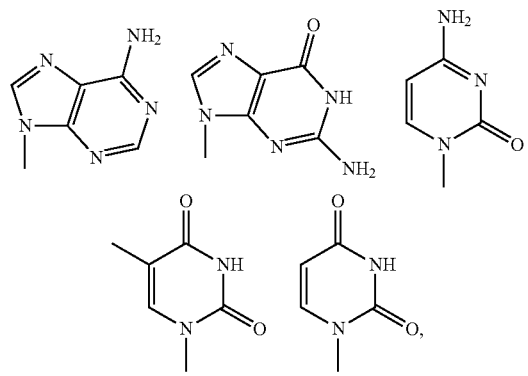

or a modified base or analog of a base, and P comprises a phosphate moiety, e.g., to provide a nucleotide having a structure according to:

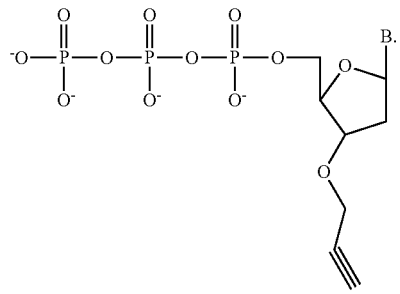

In some embodiments, P comprises a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate. In some embodiments, P comprises an azide (e.g., $N_3$, e.g., $N{=}N{=}N$), thus providing, in some embodiments, a directional, bi-functional polymerization agent. In some embodiments, the technology comprises use of a nucleotide analog as described in co-pending U.S. patent application Ser. Nos. 14/463,412 and 14/463,416; and Int'l Pat. App. PCT/US2014/051726, each of which is incorporated herein by reference in its entirety.

In some embodiments, the nucleotide analog is a 3'-O-alkynyl nucleotide analog; in some embodiments the nucleotide analog is a 3'-O-propargyl nucleotide analog such as a 3'-O-propargyl .dNTP (wherein N=A, C, G, T, or U). A propargyl nucleotide analog is a nucleotide analog comprising a base (e.g., adenine, guanine, cytosine, thymine, or uracil), a deoxyribose, and an alkyne chemical moiety attached to the 3'-oxygen of the deoxyribose. Chemical ligation between the polymerase extension products and appropriate conjugation partners (e.g., azide modified molecules) is achieved with high efficiency and specificity using, e.g., click chemistry.

The 3' hydroxyl group of the nucleotide analog is capped by a chemical moiety, e.g., an alkyne (e.g., a carbon-carbon triple bond), that halts further elongation of the nucleic acid (e.g., DNA, RNA) chain when incorporated by polymerase (e.g., DNA or RNA polymerase). The alkyne chemical moiety is a well-known conjugation partner of an azide ($N_3$) group, e.g., in a copper (I)-catalyzed 1,3-dipolar cycloaddition reaction (e.g., a "click chemistry" reaction). Reaction of the alkyne with the azide forms a five-membered triazole ring, which thereby creates a covalent linkage. The triazole ring linkage, in certain positional arrangements, has characteristics that are similar to a natural phosphodiester bond as found in a conventional nucleic acid backbone and therefore the triazole link is a nucleic acid backbone mimic. As provided by some embodiments herein, use of 3'-O-propargyl-dNTPs creates nucleic acid fragments that have a terminal 3'-O-alkyne group. Accordingly, these nucleic acid fragments can then be chemically ligated using click chemistry to any azide-modified molecules, such as 5'-azide-modified oligonucleotides (e.g., such as adaptors as provided herein or a solid support). The triazole chemical bond is compatible with typical reactions and enzymes used for biochemistry and molecular biology and, as such, does not inhibit enzymatic reactions. Accordingly, the chemically ligated nucleic acid fragments can then be used in subsequent enzymatic reactions, such as a polymerase chain reaction, a sequencing reaction, etc.

In some embodiments, the nucleotide analog comprises a reversible terminator. For example, in a nucleotide analog comprising a reversible terminator, the 3' hydroxyl groups are capped with a chemical moiety that can be removed with a specific chemical reaction, thus regenerating a free 3' hydroxyl. As such, some embodiments comprise a reaction to remove the reversible terminator and, in some embodiments, an additional purification step to remove the free capping (terminator) moiety. In some embodiments, a nucleotide comprising a reversible terminator is as described in U.S. Pat. App. Ser. No. 61/791,730 and/or in International Application Number PCT/US14/24391, each incorporated herein by reference in its entirety.

3. Adaptors

Methods of the technology involve attaching an adaptor to a nucleic acid (e.g., an amplicon or a ladder fragment as described herein). In certain embodiments, the adaptors are attached to a nucleic acid with an enzyme. The enzyme may be a ligase or a polymerase.

The ligase may be any enzyme capable of ligating an oligonucleotide (single stranded RNA, double stranded RNA, single stranded DNA, or double stranded DNA) to another nucleic acid molecule. Suitable ligases include T4 DNA ligase and T4 RNA ligase (such ligases are available commercially, e.g., from New England BioLabs). Methods for using ligases are well known in the art. The ligation may be blunt ended or via use of complementary over hanging ends. In certain embodiments, the ends of nucleic acids may be phosphorylated (e.g., using T4 polynucleotide kinase), repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3' end of the fragments, thus producing a single A overhanging. This single A is used to guide ligation of fragments with a single T overhanging from the 5' end in a method referred to as T-A cloning. The polymerase may be any enzyme capable of adding nucleotides to the 3' and the 5' terminus of template nucleic acid molecules.

In some embodiments an adaptor comprises a functional moiety for chemical ligation to a nucleotide analog. For example, in some embodiments an adaptor comprises an azide group (e.g., at the 5' end) that is reactive with an alkynyl group (e.g., a propargyl group, e.g., at the 3' end of a nucleic acid comprising the nucleotide analog), e.g., by a click chemistry reaction (e.g., using a copper-based catalyst reagent).

In some embodiments, the adaptors comprise a universal sequence and/or an index, e.g., a barcode nucleotide sequence. Additionally, adaptors can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adaptors or subsets of different adaptors (e.g., a universal sequence), one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adaptors comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adaptor oligonucleotide. When an adaptor oligonucleotide is capable of forming secondary structure, such as a hairpin, sequence elements can be located partially or completely outside the secondary structure, partially or completely inside the secondary structure, or in between sequences participating in the secondary structure. For example, when an adaptor oligonucleotide comprises a hairpin structure, sequence elements can be located partially or completely inside or outside the hybridizable sequences (the "stem"), including in the sequence between the hybridizable sequences (the "loop"). In some embodiments, the first adaptor oligonucleotides in a plurality of first adaptor oligonucleotides having different barcode sequences comprise a sequence element common among all first adaptor oligonucleotides in the plurality. In some embodiments, all second adaptor oligonucleotides comprise a sequence element common among all second adaptor oligonucleotides that is different from the common sequence element shared by the first adaptor oligonucleotides. A difference in sequence elements can be any such that at least a portion of different adaptors do not completely align, for example, due to changes in sequence length, deletion or insertion of one or more nucleotides, or a change in the nucleotide composition at one or more nucleotide positions (such as a base change or base modification). In some embodiments, an adaptor oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adaptors with complementary overhangs comprising the random sequence. In some embodiments, an adaptor overhang is complementary to a target polynucleotide overhang produced by restriction endonuclease digestion. In some embodiments, an adaptor overhang consists of an adenine or a thymine.

In some embodiments, the adaptor sequences can contain a molecular binding site identification element to facilitate identification and isolation of the target nucleic acid for downstream applications. Molecular binding as an affinity mechanism allows for the interaction between two molecules to result in a stable association complex. Molecules that can participate in molecular binding reactions include proteins, nucleic acids, carbohydrates, lipids, and small organic molecules such as ligands, peptides, or drugs.

When a nucleic acid molecular binding site is used as part of the adaptor, it can be used to employ selective hybridization to isolate a target sequence. Selective hybridization may restrict substantial hybridization to target nucleic acids containing the adaptor with the molecular binding site and capture nucleic acids, which are sufficiently complementary to the molecular binding site. Thus, through "selective hybridization" one can detect the presence of the target polynucleotide in an unpure sample containing a pool of many nucleic acids. An example of a nucleotide-nucleotide selective hybridization isolation system comprises a system with several capture nucleotides, which are complementary sequences to the molecular binding identification elements, and are optionally immobilized to a solid support. In other embodiments, the capture polynucleotides could be complementary to the target sequences itself or a barcode or unique tag contained within the adaptor. The capture polynucleotides can be immobilized to various solid supports, such as inside of a well of a plate, mono-dispersed spheres, microarrays, or any other suitable support surface known in the art. The hybridized complementary adaptor polynucleotides attached on the solid support can be isolated by washing away the undesirable non-binding nucleic acids, leaving the desirable target polynucleotides behind. If complementary adaptor molecules are fixed to paramagnetic spheres or similar bead technology for isolation, then spheres can then be mixed in a tube together with the target polynucleotide containing the adaptors. When the adaptor sequences have been hybridized with the complementary sequences fixed to the spheres, undesirable molecules can be washed away while spheres are kept in the tube with a magnet or similar agent. The desired target molecules can be subsequently released by increasing the temperature, changing the pH, or by using any other suitable elution method known in the art.

4. Barcodes

A barcode is a known nucleic acid sequence that allows some feature of a nucleic acid with which the barcode is associated to be identified. In some embodiments, the feature of the nucleic acid to be identified is the sample or source from which the nucleic acid is derived. The barcode sequence generally includes certain features that make the sequence useful in sequencing reactions. For example, the barcode sequences are designed to have minimal or no homopolymer regions, e.g., 2 or more of the same base in a row such as AA or CCC, within the barcode sequence. In some embodiments, the barcode sequences are also designed so that they are at least one edit distance away from the base addition order when performing base-by-base sequencing, ensuring that the first and last bases do not match the expected bases of the sequence.

In some embodiments, the barcode sequences are designed such that each sequence is correlated to a particular target nucleic acid, allowing the short sequence reads to be correlated back to the target nucleic acid from which they came. Methods of designing sets of barcode sequences are shown, for example, in U.S. Pat. No. 6,235,475, the contents of which are incorporated by reference herein in their entirety. In some embodiments, the barcode sequences range from about 5 nucleotides to about 15 nucleotides. In a particular embodiment, the barcode sequences range from about 4 nucleotides to about 7 nucleotides. Since the barcode sequences are sequenced along with the ladder fragment nucleic acid, in embodiments using longer sequences the barcode length is of a minimal length so as to permit the longest read from the fragment nucleic acid attached to the barcode. In some embodiments, the barcode sequences are spaced from the fragment nucleic acid molecule by at least one base, e.g., to minimize homopolymeric combinations.

In some embodiments, lengths and sequences of barcode sequences are designed to achieve a desired level of accuracy of determining the identity of nucleic acid. For example, in some embodiments barcode sequences are designed such that after a tolerable number of point mutations, the identity of the associated nucleic acid can still be deduced with a desired accuracy. In some embodiments, a Tn-5 transposase (commercially available from Epicentre Biotechnologies; Madison, Wis.) cuts a nucleic acid into fragments and inserts short pieces of DNA into the cuts. The short pieces of DNA are used to incorporate the barcode sequences.

Attaching adaptors comprising barcodes to nucleic acid templates is shown in U.S. Pat. Appl. Pub. No. 2008/0081330 and in International Pat. Appl. No. PCT/US09/64001, the content of each of which is incorporated by reference herein in its entirety. Methods for designing sets of barcode sequences and other methods for attaching adaptors (e.g., comprising barcode sequences) are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety. In certain embodiments, a single barcode is attached to each fragment. In other embodiments, a plurality of barcodes, e.g., two barcodes, is attached to each fragment.

5. Samples

In some embodiments, nucleic acid template molecules (e.g., DNA or RNA) are isolated from a biological sample containing a variety of other components, such as proteins, lipids, and non-template nucleic acids. Nucleic acid template molecules can be obtained from any material (e.g., cellular material (live or dead), extracellular material, viral material, environmental samples (e.g., metagenomic samples), synthetic material (e.g., amplicons such as provided by PCR or other amplification technologies)), obtained from an animal, plant, bacterium, archaeon, fungus, or any other organism. Biological samples for use in the present invention include viral particles or preparations thereof. Nucleic acid template molecules can be obtained directly from an organism or from a biological sample obtained from an organism, e.g., from blood, urine, cerebrospinal fluid, seminal fluid, saliva, sputum, stool, hair, sweat, tears, skin, and tissue. Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a source for nucleic acid for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA that has been stored in a freezer.

Nucleic acid template molecules can be obtained, e.g., by extraction from a biological sample, e.g., by a variety of techniques such as those described by Maniatis, et al. (1982) *Molecular Cloning: A Laboratory Manual*, Cold Spring Harbor, N.Y. (see, e.g., pp. 280-281).

In some embodiments, size selection of the nucleic acids is performed to remove very short fragments or very long fragments. Suitable methods select a size are known in the art. In various embodiments, the size is limited to be 0.5, 1, 2, 3, 4, 5, 7, 10, 12, 15, 20, 25, 30, 50, 100 kb or longer.

In various embodiments, a nucleic acid is amplified. Any amplification method known in the art may be used. Examples of amplification techniques that can be used include, but are not limited to, PCR, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), hot start PCR, nested PCR, in situ polony PCR, in situ rolling circle amplification (RCA), bridge PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid based sequence amplification (NABSA). Other amplification methods that can be used herein include those described in U.S. Pat. Nos. 5,242,794; 5,494,810; 4,988,617; and 6,582,938.

In some embodiments, end repair is performed to generate blunt end 5' phosphorylated nucleic acid ends using commercial kits, such as those available from Epicentre Biotechnologies (Madison, Wis.).

6. Nucleic Acid Sequencing

In some embodiments of the technology, nucleic acid sequence data are generated. Various embodiments of nucleic acid sequencing platforms (e.g., a nucleic acid sequencer) include components as described below. According to various embodiments, a sequencing instrument includes a fluidic delivery and control unit, a sample processing unit, a signal detection unit, and a data acquisition, analysis and control unit. Various embodiments of the instrument provide for automated sequencing that is used to gather sequence information from a plurality of sequences in parallel and/or substantially simultaneously.

In some embodiments, the fluidics delivery and control unit includes a reagent delivery system. The reagent delivery system includes a reagent reservoir for the storage of various reagents. The reagents can include RNA-based primers, forward/reverse DNA primers, nucleotide mixtures (e.g., compositions comprising nucleotide analogs as provided herein) for sequencing-by-synthesis, buffers, wash reagents, blocking reagents, stripping reagents, and the like. Additionally, the reagent delivery system can include a pipetting system or a continuous flow system that connects the sample processing unit with the reagent reservoir.

In some embodiments, the sample processing unit includes a sample chamber, such as flow cell, a substrate, a micro-array, a multi-well tray, or the like. The sample processing unit can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber. In some embodiments, the signal detection unit can include an imaging or detection sensor. For example, the imaging or detection sensor (e.g., a fluorescence detector or an electrical detector) can include a CCD, a CMOS, an ion sensor, such as an ion sensitive layer overlying a CMOS, a current detector, or the like. The signal detection unit can include an excitation system to cause a probe, such as a fluorescent dye, to emit a signal. The detection system can include an illumination source, such as arc lamp, a laser, a light emitting diode (LED), or the like. In particular embodiments, the signal detection unit includes optics for the transmission of light from an illumination source to the sample or from the sample to the imaging or detection sensor. Alternatively, the signal detection unit may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current, voltage, or resistance are detected without the need for an illumination source.

In some embodiments, a data acquisition analysis and control unit monitors various system parameters. The system parameters can include temperature of various portions of the instrument, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of the instruments and systems are used to practice sequencing methods such as sequencing by synthesis, single molecule methods, and other sequencing techniques. Sequencing by synthesis can include the incorporation of dye labeled nucleotides, chain termination, ion/proton sequencing, pyrophosphate sequencing, or the like. Single molecule techniques can include staggered sequencing, where the sequencing reactions is paused to determine the identity of the incorporated nucleotide.

In some embodiments, the sequencing instrument determines the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In some embodiments, the nucleic acid can include or be derived from a fragment library, a mate pair library, a ChIP fragment, or the like. In particular embodiments, the sequencing instrument can obtain the sequence information from a single nucleic acid molecule or from a group of substantially identical nucleic acid molecules.

In some embodiments, the sequencing instrument can output nucleic acid sequencing read data in a variety of different output data file types/formats, including, but not limited to: *.txt, *.fasta, *.csfasta, *seq.txt, *qseq.txt, *.fastq, *.sff, *prb.txt, *.sms, *srs, and/or *.qv.

7. Next-Generation Sequencing Technologies

Particular sequencing technologies contemplated by the technology are next-generation sequencing (NGS) methods that share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), the NGS fragment library is clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, the fragments of the NGS fragment library are captured on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 100 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. No. 5,912,148; U.S. Pat. No. 6,130,073; each herein incorporated by reference in their entirety) also involves clonal amplification of the NGS fragment library by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, HeliScope by Helicos BioSciences is employed (Voelkerding et al., Clinical Chem., 55: 641-658, 2009; MacLean et al., Nature Rev. Microbiol., 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Sequencing is achieved by addition of polymerase and serial addition of fluorescently-labeled dNTP reagents. Incorporation events result in a fluor signal corresponding to the dNTP, and signal is captured by a CCD camera before each round of dNTP addition. Sequence read length ranges from 25-50 nucleotides, with overall output exceeding 1 billion nucleotide pairs per analytical run.

In some embodiments, 454 sequencing by Roche is used (Margulies et al. (2005) *Nature* 437: 376-380). 454 sequencing involves two steps. In the first step, DNA is sheared into fragments of approximately 300-800 base pairs and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., an adaptor that contains a 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a fragment of the NGS fragment library to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs. However, the cost of acquiring a pH-mediated sequencer is approximately $50,000, excluding sample preparation equipment and a server for data analysis.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781,166; each herein incorporated by reference in their entirety) in which fragments of the NGS fragment library are immobilized, primed, then subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55: 641-658, 2009; MacLean et al., Nature Rev. Microbiol., 7: 287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10^{-21}$ l). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ l). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

In some embodiments, nanopore sequencing is used (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

In some embodiments, a sequencing technique uses a chemical-sensitive field effect transistor (chemFET) array to sequence DNA (for example, as described in US Patent Application Publication No. 20090026082). In one example of the technique, DNA molecules are placed into reaction chambers, and the template molecules are hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In some embodiments, sequencing technique uses an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

In some embodiments, "four-color sequencing by synthesis using cleavable fluorescents nucleotide reversible terminators" as described in Turro, et al. PNAS 103: 19635-40 (2006) is used, e.g., as commercialized by Intelligent Bio-Systems. The technology described in U.S. Pat. Appl. Pub. Nos. 2010/0323350, 2010/0063743, 2010/0159531, 20100035253, 20100152050, incorporated herein by reference for all purposes.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.;

and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analog incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008)

"Selective aluminum passivation for targeted immobilization of single DNA polymerase molecules in zero-mode waveguide nanostructures" PNAS 105(4): 1176-81, all of which are herein incorporated by reference in their entireties.

8. Nucleic Acid Sequence Analysis

In some embodiments, a computer-based analysis program is used to translate the raw data generated by the detection assay (e.g., sequencing reads) into data of predictive value for an end user (e.g., medical personnel). The user can access the predictive data using any suitable means. Thus, in some preferred embodiments, the present technology provides the further benefit that the user, who is not likely to be trained in genetics or molecular biology, need not understand the raw data. The data is presented directly to the end user in its most useful form. The user is then able to immediately utilize the information to determine useful information (e.g., in medical diagnostics, research, or screening).

Some embodiments provide a system for reconstructing a nucleic acid sequence. The system can include a nucleic acid sequencer, a sample sequence data storage, a reference sequence data storage, and an analytics computing device/server/node. In some embodiments, the analytics computing device/server/node can be a workstation, mainframe computer, personal computer, mobile device, etc. The nucleic acid sequencer can be configured to analyze (e.g., interrogate) a nucleic acid fragment (e.g., single fragment, mate-pair fragment, paired-end fragment, etc.) utilizing all available varieties of techniques, platforms or technologies to obtain nucleic acid sequence information, in particular the methods as described herein using compositions provided herein. In some embodiments, the nucleic acid sequencer is in communications with the sample sequence data storage either directly via a data cable (e.g., serial cable, direct cable connection, etc.) or bus linkage or, alternatively, through a network connection (e.g., Internet, LAN, WAN, VPN, etc.). In some embodiments, the network connection can be a "hardwired" physical connection. For example, the nucleic acid sequencer can be communicatively connected (via Category 5 (CAT5), fiber optic or equivalent cabling) to a data server that is communicatively connected (via CAT5, fiber optic, or equivalent cabling) through the Internet and to the sample sequence data storage. In some embodiments, the network connection is a wireless network connection (e.g., Wi-Fi, WLAN, etc.), for example, utilizing an 802.11 a/b/g/n or equivalent transmission format. In practice, the network connection utilized is dependent upon the particular requirements of the system. In some embodiments, the sample sequence data storage is an integrated part of the nucleic acid sequencer.

In some embodiments, the sample sequence data storage is any database storage device, system, or implementation (e.g., data storage partition, etc.) that is configured to organize and store nucleic acid sequence read data generated by nucleic acid sequencer such that the data can be searched and retrieved manually (e.g., by a database administrator or client operator) or automatically by way of a computer program, application, or software script. In some embodiments, the reference data storage can be any database device, storage system, or implementation (e.g., data storage partition, etc.) that is configured to organize and store reference sequences (e.g., whole or partial genome, whole or partial exome, SNP, gen, etc.) such that the data can be searched and retrieved manually (e.g., by a database administrator or client operator) or automatically by way of a computer program, application, and/or software script. In some embodiments, the sample nucleic acid sequencing read data can be stored on the sample sequence data storage and/or the reference data storage in a variety of different data file types/formats, including, but not limited to: *.txt, *.fasta, *.csfasta, *seq.txt, *qseq.txt, *.fastq, *.sff, *prb.txt, *.sms, *srs and/or *.qv.

In some embodiments, the sample sequence data storage and the reference data storage are independent standalone devices/systems or implemented on different devices. In some embodiments, the sample sequence data storage and the reference data storage are implemented on the same device/system. In some embodiments, the sample sequence data storage and/or the reference data storage can be implemented on the analytics computing device/server/node. The analytics computing device/server/node can be in communications with the sample sequence data storage and the reference data storage either directly via a data cable (e.g., serial cable, direct cable connection, etc.) or bus linkage or, alternatively, through a network connection (e.g., Internet, LAN, WAN, VPN, etc.). In some embodiments, analytics computing device/server/node can host a reference mapping engine, a de novo mapping module, and/or a tertiary analysis engine. In some embodiments, the reference mapping engine can be configured to obtain sample nucleic acid sequence reads from the sample data storage and map them against one or more reference sequences obtained from the reference data storage to assemble the reads into a sequence that is similar but not necessarily identical to the reference sequence using all varieties of reference mapping/alignment techniques and methods. The reassembled sequence can then be further analyzed by one or more optional tertiary analysis engines to identify differences in the genetic makeup (genotype), gene expression or epigenetic status of individuals that can result in large differences in physical characteristics (phenotype). For example, in some embodiments, the tertiary analysis engine can be configured to identify various genomic variants (in the assembled sequence) due to mutations, recombination/crossover or genetic drift. Examples of types of genomic variants include, but are not limited to: single nucleotide polymorphisms (SNPs), copy number variations (CNVs), insertions/deletions (Indels), inversions, etc. The optional de novo mapping module can be configured to assemble sample nucleic acid sequence reads from the sample data storage into new and previously unknown sequences. It should be understood, however, that the various engines and modules hosted on the analytics computing device/server/node can be combined or collapsed into a single engine or module, depending on the requirements of the particular application or system architecture. Moreover, in some embodiments, the analytics computing device/server/node can host additional engines or modules as needed by the particular application or system architecture.

In some embodiments, the mapping and/or tertiary analysis engines are configured to process the nucleic acid and/or reference sequence reads in color space. In some embodiments, the mapping and/or tertiary analysis engines are configured to process the nucleic acid and/or reference sequence reads in base space. It should be understood, however, that the mapping and/or tertiary analysis engines disclosed herein can process or analyze nucleic acid sequence data in any schema or format as long as the schema or format can convey the base identity and position of the nucleic acid sequence.

In some embodiments, the sample nucleic acid sequencing read and referenced sequence data can be supplied to the analytics computing device/server/node in a variety of different input data file types/formats, including, but not limited to: *.txt, *.fasta, *.csfasta, *seq.txt, *qseq.txt, *.fastq, *.sff, *prb.txt, *.sms, *srs and/or *.qv.

Furthermore, a client terminal can be a thin client or thick client computing device. In some embodiments, client terminal can have a web browser that can be used to control the operation of the reference mapping engine, the de novo mapping module and/or the tertiary analysis engine. That is, the client terminal can access the reference mapping engine, the de novo mapping module and/or the tertiary analysis engine using a browser to control their function. For example, the client terminal can be used to configure the operating parameters (e.g., mismatch constraint, quality value thresholds, etc.) of the various engines, depending on the requirements of the particular application. Similarly, client terminal can also display the results of the analysis performed by the reference mapping engine, the de novo mapping module and/or the tertiary analysis engine.

The present technology also encompasses any method capable of receiving, processing, and transmitting the information to and from laboratories conducting the assays, information provides, medical personal, and subjects.

9. Uses

The technology is not limited to particular uses, but finds use in a wide range of research (basic and applied), clinical, medical, and other biological, biochemical, and molecular biological applications. Some exemplary uses of the technology include genetics, genomics, and/or genotyping, e.g., of plants, animals, and other organisms, e.g., to identify haplotypes, phasing, and/or linkage of mutations and/or alleles. Particular and non-limiting illustrative examples in the human medical context include testing for cystic fibrosis and fragile X syndrome.

In addition, the technology finds use in the field of infectious disease, e.g., in identifying infectious agents such as viruses, bacteria, fungi, etc., and in determining viral types, families, species, and/or quasi-species, and to identify haplotypes, phasing, and/or linkage of mutations and/or alleles. A particular and non-limiting illustrative example in the area of infectious disease is characterization of human immunodeficiency virus (HIV) genetic elements and identifying haplotypes, phasing, and/or linkage of mutations and/or alleles. Other particular and non-limiting illustrative examples in the area of infectious disease include characterizing antibiotic resistance determinants; tracking infectious organisms for epidemiology; monitoring the emergence and evolution of resistance mechanisms; identifying species, sub-species, strains, extra-chromosomal elements, types, etc. associated with virulence, monitoring the progress of treatments, etc.

In some embodiments, the technology finds use in transplant medicine, e.g., for typing of the major histocompatibility complex (MHC), typing of the human leukocyte antigen (HLA), and for identifying haplotypes, phasing, and/or linkage of mutations and/or alleles associated with transplant medicine (e.g., to identify compatible donors for a particular host needing a transplant, to predict the chance of rejection, to monitor rejection, to archive transplant material, for medical informatics databases, etc.).

In some embodiments, the technology finds use in oncology and fields related to oncology. Particular and non-limiting illustrative examples in the area of oncology are identifying genetic and/or genomic aberrations related to cancer, predisposition to cancer, and/or treatment of cancer. For example, in some embodiments the technology finds use in detecting the presence of a chromosomal translocation associated with cancer; and in some embodiments the technology finds use in identifying novel gene fusion partners to provide cancer diagnostic tests. In some embodiments, the technology finds use in cancer screening, cancer diagnosis, cancer prognosis, measuring minimal residual disease, and selecting and/or monitoring a course of treatment for a cancer.

In some embodiments, the technology finds use in characterizing nucleotide sequences. For example, in some embodiments, the technology finds use in detecting insertions and/or deletions ("indels") in a nucleotide (e.g., genome, gene, etc.) sequence. It is contemplated that the technology described herein provides improved indel detection relative to conventional technologies. In addition, the technology finds use in detecting short tandem repeats (STRs), inversions, large insertions, and in sequencing repetitive (e.g., highly repetitive) regions of a nucleotide sequence (e.g., of a genome).

Although the disclosure herein refers to certain illustrated embodiments, it is to be understood that these embodiments are presented by way of example and not by way of limitation.

EXAMPLES

Example 1—Comparison with Illumina MiSeq

During the development of the technology provided herein, calculations were performed to compare the performance of the technology provided herein (Tables 1 and 2, "SOD Library") with conventional technology provided by Illumina in the MiSeq platform (Tables 1 and 2, "Illumina Amplicon Library"). Data were collected for two scenarios varying, e.g., the number of samples per run, criteria to measure throughput, etc. (see Tables 1 and 2).

As shown in Tables 1 and 2, the technology described herein decreases instrument run-time, has a higher throughput, and produces a higher percentage of reads with quality scores greater than Q30 with respect to NGS library construction using the Illumina technology.

TABLE 1 comparison with Illumina MiSeq (Targeted Sequencing: Amplicon Panel) MiSeq (Sequencing reagent kit v2)[a]

|  | SOD Library | Illumina Amplicon Library |
|---|---|---|
| # of samples per run | 8 | 8 |
| # of amplicons per sample | 50 | 50 |
| Average size of amplicons (bp) | 400 | 400 |
| Required length of SBS read | 1 × 50 | 2 × 250[b] |
| Total run time (hours)[c] | 3 | 37 |
| Avg. coverage for each amplicon per sample[d] | 5357 | 37500 |
| Throughput (# of samples with 1000x coverage/hour)[e] | 14.3 | 8.1 |
| Quality scores (percent of reads with score > Q30)[f] | >90% | >75% |

[a]MiSeq Reagent kit v2: Dual-surface scanning, 12-15 million clusters passing filter
[b]To cover the entire 400 bp amplicon, a 2 × 250 bp pair-end read strategy is implemented where the reads are overlapped by ~100 bp
[c]Actual sequencing portion only (does not include cluster generation time)
[d]To calculate coverage for SOD library: [(Total # of reads)/((insert size − SOD readlength) × (# of samples in a run × # of amplicons per sample))] × SOD readlength: e.g., [(15 × 10^6)/((400 − 50) × (8 × 50))] × 50
[e]To calculate throughput: [(mean coverage)/1000]/(total run time)
[f]Based on MiSeq sequencing specification provided by Illumina, e.g., in their online materials.

TABLE 2 comparison with Illumina MiSeq
(Targeted Panel Sequencing of 400 bp insert)
MiSeq (seq kit v2)[a]

| | Targeted Panel Sequencing (400 bp insert) | | |
|---|---|---|---|
| | SOD Library | Illumina Amplicon Library | |
| # of samples per run | 8 | 8 | 56 |
| # of amplicons per sample | 50 | 50 | 50 |
| Average size of amplicons (bp) | 400 | 400 | 400 |
| Required length of SBS read | 1 × 50 | 2 × 250[b] | 2 × 250[b] |
| Total run time (hours)[c] | 4 | 38 | 38 |
| Mean coverage for each amplicon per sample[d] | 5357 | 37500 | 5357 |
| Throughput (# of samples with 2000x coverage/hour)[e] | 7.1 | 4.1 | 4.1 |
| Quality scores (percent of reads with score > Q30)[f] | >90% | >75% | >75% |

[a]MiSeq Reagent kit v2: Dual-surface scanning, 15 million clusters passing filter
[b]To cover the entire 200 or 400 bp amplicon, a 2 × 150 or 2 × 250 bp (respectively) pair-end read strategy is implemented where the reads are overlapped by ~100 bp
[c]Actual sequencing portion only (does not include cluster generation time)
[d]To calculate coverage for SOD library: [(Total # of reads)/((insert size − SOD readlength) × (# of samples in a run × # of amplicons per sample))] × SOD readlength: e.g., [(15 × 10⁶)/((400 − 50) × (8 × 50))] × 50
[e]To calculate throughput: [(mean coverage)/2000]/(total run time)
[f]Based on MiSeq sequencing specification provided by Illumina, e.g., in their online materials.

Example 2—Comparison with Ion Torrent PGM (Targeted Sequencing: Amplicon Panel)

During the development of the technology provide herein, calculations were performed to compare the performance of the technology provided herein (Tables 3 and 4, "SOD Library") with conventional technology provided by Ion Torrent in the PGM platform (Tables 3 and 4, "Ion Amplicon Library"). Data were collected for two scenarios varying, e.g., the number of samples per run, criteria to measure throughput, etc. (see Tables 3 and 4).

As shown in Tables 3 and 4, the technology described herein decreases instrument run-time and produces a higher percentage of reads with quality scores greater than Q20 with respect to NGS library construction using the Ion Torrent technology.

TABLE 3 comparison with Ion Torrent PGM
Ion PGM (400 bp Sequencing reagent kit v2)[a]

| | SOD Library | Ion Amplicon Library |
|---|---|---|
| # of samples per run | 1 | 1 |
| # of amplicons per sample | 50 | 50 |
| Average size of amplicons (bp) | 400 | 400 |
| Required length of SBS read | 1 × 50 | 1 × 400 (bi-directional)[b] |
| Total run time (hours)[c] | 0.5 | 4 |
| Avg. coverage for each amplicon per sample[d] | 1143 | 8000 |
| Throughput (# of samples with 1000x coverage/hour)[e] | 2.3 | 2.0 |

TABLE 3-continued comparison with Ion Torrent PGM
Ion PGM (400 bp Sequencing reagent kit v2)[a]

| | SOD Library | Ion Amplicon Library |
|---|---|---|
| Quality scores (percent of reads with score > Q20)[f] | >90% | >50% |

[a]PGM 400 bp Sequencing Reagent kit v2
[b]To cover the entire 400 bp amplicon, a 1 × 400 bp bi-directional sequencing is performed
[c]Actual sequencing portion only (does not include OneTouch2 and other pre-sequencing process time)
[d]To calculate coverage for SOD library: [(0.4 × 10⁶)/((400 − 50) × (8 × 50))] × 50
[e]To calculate throughput: [(avg. coverage)/1000]/(total run time)
[f]Projected based on: Loman N. et al. (2012) "Performance comparison of benchtop high-throughput sequencing platforms" Nature Biotechnology, vol. 30-5.

TABLE 4 comparison with Ion Torrent PGM
Ion PGM (318 v2/seq kit)

| | Targeted Panel Sequencing (400 bp insert) | | |
|---|---|---|---|
| | SOD Library | Ion Amplicon Library | |
| # of samples per run | 4 | 4 | 28 |
| # of amplicons per sample | 50 | 50 | 50 |
| Average size of amplicons (bp) | 400 | 400 | 400 |
| Required length of SBS read | 1 × 50 | 1 × 400 (bi-directional)[b] | |
| Total run time (hours)[c] | 0.5 | 7.25 | 7.25 |
| Mean coverage for each amplicon per sample[d] | 4286 | 30000 | 4286 |
| Throughput (# of samples with 2000x coverage/hour)[e] | 17.1 | 8.3 | 8.3 |
| Quality scores (percent of reads with score > Q20)[f] | >90% | >50% | >50% |

[a]Ion PGM chip 318/v2: ~6 million load wells producing reads passing filter
[b]To cover the entire 200-bp or 400-bp amplicon, a 200-bp (bi-directional) or 400-bp (bi-directional) strategy is implemented, respectively
[c]Actual sequencing portion only (does not include ePCR/enrichment)
[d]To calculate coverage for SOD library: [(# of total reads)/((insert size − SOD readlength) × (# of samples × # of amplicon))] × SOD readlength, e.g., [(15 × 10⁶)/((400 − 50) × (8 × 50))] × 50
[e]To calculate throughput: [(mean coverage)/2000]/(total run-time)
[f]Based on Ion Torrent sequencing specification available in the Ion Torrent online materials

Example 3—Comparison Technologies for Long Reads

Tables 5 and 6 compare the performance of the technology provided herein with conventional technologies for sequencing long amplicons of approximately 1000 bp (Table 5) and 2000 bp (Table 6). Run-time does not increase with amplicon size for the present technology because the read size is ~30-50 bases regardless of the size of the target nucleic acid to be sequenced. In some embodiments, a 2000-bp sequence is produced by the technology provided herein in a time that is an order of magnitude less than the conventional technology (see, e.g., Table 6). In some embodiments, the technology provided herein provides a longer sequence read with the same run time as the conventional technology.

TABLE 5 comparison for long-amplicon sequencing 1000 bp

| | SOD Library[a] | Illumina TruSeq Library | Ion gDNA Library |
|---|---|---|---|
| # of samples per run | 8 | 8 | 1 |
| # of amplicons per sample | 50 | 50 | 50 |
| Average size of amplicons (bp) | 1000 | 1000 | 1000 |
| Required length of SBS read | 1 × 50 | 2 × 250 (pair-end) | 1 × 400 (bi-directional) |
| Total run time (hours) | 3 | 37 | 4 |
| Avg. coverage for each amplicon per sample | 1974 | — | — |
| Throughput (# of samples with 1000x coverage/hour) | 5.3 | — | — |
| Quality scores (percent of reads with score > Q30) | >90% | — | — |

[a]SOD library run on a MiSeq with sequencing reagent kit v2

TABLE 6 comparison for long-amplicon sequencing 2000 bp Long Read Application (2 Kb insert size)

| | SOD Library[a] | Illumina Lib | Ion PGM Lib |
|---|---|---|---|
| # of samples per run | 8 | 8 | 4 |
| # of amplicons per sample | 50 | 50 | 50 |
| Average size of amplicons (bp) | 2000 | 2000 | 2000 |
| Required length of SBS read | 1 × 50 | 2 × 250 | 1 × 400 |
| Total run time (hours) | 3 on MiSeq; 0.5 on PGM | 37[b] | 7.25 |
| Mean coverage for each amplicon per sample | 962 | — | — |
| Throughput (# of samples with 2000x coverage/hour) | 2.6 | — | — |
| Quality scores (percent of reads with score > Q30) | >90% | — | — |
| Cost per run (seq reagent and chip only, $) | 725 | — | — |
| Cost per sample ($) | 90.63 | — | — |

[a]SOD library prep time for longer insert size is longer in some embodiments (e.g., from ~6.5 hours to ~8.5 hours)
[b]Illumina "Moleculo" technology

Example 4—Concept Verification of Data Obtained Using a Model Library

During the development of embodiments of the technology provided here, data were collected to verify the technology using a model library. As shown in FIG. 4, a consensus sequence of ~127 bp is constructed from a collection of ~35-bp reads produced according to embodiments of the technology provided. The calculated sequencing run time on an Illumina MiSeq DNA sequencing apparatus to produce the ~127-bp sequence using a library produced by the technology provided herein is approximately 2.5 hours. Using the conventional technology to provide the library, a run time of ~13 hours produces the same ~127-bp sequence read.

Example 5—Ladder Generation Using 3'-O-Propargyl dNTP Termination

During the development of embodiments of the technology provided herein, experiments were conducted to assess the generation of terminated nucleic acid fragments in a reaction comprising a mixture of 3'-O-propargyl-dNTPs and natural (standard) dNTPs. In particular, experiments were conducted to assess the generation of fragments terminated at each position within the target region by incorporation of chain-terminating 3'-O-propargyl-dNTPs by DNA polymerase during synthesis. Polymerase extension assays were conducted using a template nucleic acid having a sequence from human KRAS (e.g., KRAS exon 2 and flanking intron sequences) and a complementary primer:

KRAS Exon 2 Template
(SEQ ID NO: 1)
TTATTATAAGGCCTGCTGAAAATGACTGAATATAAACTTGTGGTAGTTGG

AGCTGGTGGCGTAGGCAAGAGTGCCTTGACGATACAGCTAATTCAGAATC

ATTTTGTGGACGAATATGATCCAACAATAGAGGTAAATCTTGTTTTAATA

TGCATATTACTGGTGCAGGACCATTCT

R_ke2_trP1_T_bio
(SEQ ID NO: 2)
bTAAUCCTCTCTATGGGCAGTCGGTGATAGAATGGTCCTGCACCAGTAA In the R_ke2_trP1_T_bio primer sequence (SEQ ID NO: 2), a "b" indicates a biotin modification and a "U" indicates a deoxyuridine modification. Incorporation of the primers into extension products produces extension products comprising a uracil. The uracil is useful, e.g., for cleavage of the product (e.g., using uracil cleavage reagents) in a number of molecular biological manipulations (e.g., cleaving the product from a solid support).

Experiments were conducted using a mixture of natural dNTPs and all four of the 3'-O-propargyl-dNTPs in a single reaction. The DNA fragment generation reaction mix comprised 20 mM Tris-HCl, 10 mM $(NH_4)SO_4$, 10 mM KCl, 2 mM $MnCl_2$, 0.1% Triton X-100, 1000 pmol dATP, 1000 pmol dCTP, 1000 pmol dGTP, 1000 pmol dTTP, 100 pmol of 3'-O-propargyl-dATP, 100 pmol of 3'-O-propargyl-dCTP, 100 pmol of 3'-O-propargyl-dGTP, 100 pmol of 3'-O-propargyl-dTTP, 6.25 pmol of primer R_ke2_trP1_T_bio (SEQ ID NO: 2), and 2 units of THERMINATOR II DNA polymerase (New England BioLabs) in a 25-μl reaction volume. 0.5 pmol of purified amplicon corresponding to a region in KRAS exon 2 (SEQ ID NO: 1) was used as template. The polymerase extension reaction was thermocycled by heating to 95° C. for 2 minutes, followed by 45 cycles at 95° C. for 15 seconds, 55° C. for 25 seconds, and 65° C. for 35 seconds.

After the polymerase extension reaction, 1 μl of the reaction mix was used directly for DNA fragment size analysis using gel electrophoresis (Agilent 2100 Bioanalyzer and High Sensitivity DNA Assay Chip). Fragment size analysis of the reaction products indicated that the fragment generation reaction successfully produced a ladder of nucleic acid fragments having the expected sizes.

Example 6—Synthesis of 5'-Azido-Methyl-Modified Oligonucleotide

During the development of embodiments of the technology provided herein, an oligonucleotide comprising a 5'-azido-methyl modification was synthesized and characterized. Synthesis of the modified oligonucleotide was performed using phosphoramidite chemical synthesis. In the last synthetic step, phosphoramidite chemical synthesis was used to incorporate a 5'-iodo-dT phosphoramidite at the terminal 5' position. The oligonucleotide attached to the solid support in the reaction column was then treated as follows.

First, sodium azide (30 mg) was resuspended in dry DMF (1 ml), heated for 3 hours at 55° C., and cooled to room temperature. The supernatant was taken up with a 1-ml syringe and passed back and forth through the reaction column comprising the 5'-iodo-modified oligonucleotide and incubated overnight at ambient (room) temperature. After incubation, the column was washed with dry DMF, washed with acetonitrile, and then dried via argon gas. The resulting 5'-azido-methyl-modified oligonucleotide was cleaved from the solid support and deprotected by heating in aqueous ammonia for 5 hours at 55° C. The final product was an oligonucleotide having the sequence shown below:

(SEQ ID NO: 3)
Az-TCTGAGTCGGAGACACGCAGGGATGAGATGGT

The "Az" indicates the azido-methyl modification at the 5' end (e.g., 5'-azido-methyl modification), e.g., to provide an oligonucleotide having a structure according to

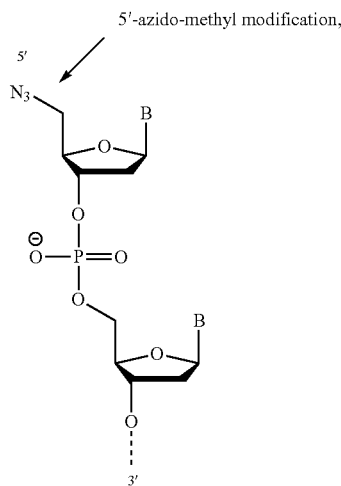

where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

Example 7—Conjugation of 5'-Azido-Methyl-Modified Oligonucleotide and 3'-O-Propargyl-Modified Nucleic Acid Fragments During the development of embodiments of the technology provided herein, experiments were conducted to test the conjugation of a 5'-azido-methyl-modified oligonucleotide (e.g., see Example 6) to 3'-O-propargyl-modified nucleic acid fragments (e.g., see Example 5) by click chemistry. In particular, experiments were conducted in which a 5'-azido-methyl-modified oligonucleotide was chemically conjugated to 3'-O-propargyl-modified DNA fragments using copper (I) catalyzed 1,3-dipolar alkyne-azide cycloaddition chemistry ("click chemistry").

Click chemistry was performed using commercially available reagents (baseclick GmbH, Oligo-Click-M Reload kit) according to the manufacturer's instructions. Briefly, approximately 0.1 pmol of 3'-O-propargyl-modified DNA fragments comprising a 5'-biotin modification were reacted with approximately 500 pmol of 5'-azido-methyl-modified oligonucleotide using the click chemistry reagent in a total volume of 10 µl. The reaction mixture was incubated at 45° C. for 30 minutes. Following the incubation, the supernatant was transferred to a new microcentrifuge tube and a 40-µl volume of the commercially supplied binding and wash buffer (e.g., 1 M NaCl, 10 mM Tris-HCl, 1 mM EDTA, pH 7.5) was added. The conjugated reaction product was isolated from the excess 5'-azido-methyl-modified oligonucleotide by incubating the click chemistry reaction mixture with streptavidin-coated magnetic beads (Dynabeads, MyOne Streptavidin C1, Life Technologies) at ambient (room) temperature for 15 minutes. The beads were separated from the supernatant using a magnet and the supernatant was removed. Subsequently, the beads were washed twice using the binding and wash buffer and then resuspended in 25 µl of TE buffer (10 mM Tris-HCl, 0.1 mM EDTA, pH approximately 8).

The product was cleaved from the solid support (bead) using uracil cleavage (Uracil Glycosylase and Endonuclease VIII, Enzymatics). In particular, uracil cleavage reagents were used to cleave the reaction products at the site of the deoxyuridine modification located near the 5'-terminal location of the conjugated product (see SEQ ID NOs: 2-5). Finally, the supernatant comprising the conjugated product was purified using Ampure XP (Beckman Coulter) following the manufacturer's protocol and eluted in 20 µl of TE buffer.

Example 8—Amplification of Conjugated Product

During the development of embodiments of the technology described herein, experiments were performed to characterize the chemical conjugation of the 5'-azido-methyl-modified oligonucleotide to the 3'-O-propargyl modified nucleic acid fragments and to evaluate the triazole linkage as a mimic of a natural phosphodiester bond in a nucleic acid backbone. To test the ability of a polymerase to recognize the conjugated product as a template and traverse the triazole linkage during synthesis, PCR primers were designed to produce amplicons that span the triazole linkage of the conjugation products:

SEQ ID NO: 4
Primer 1  CCTCTCTATGGGCAGTCGGTGAT

SEQ ID NO: 5
Primer 2  CCATCTCATCCCTGCGTGTCTC

A commercially available PCR pre-mix (KAPA 2G HS, KAPA Biosystems) was used to provide a 25-µl reaction mixture comprising, in addition to components provided by the mix (e.g., buffer, polymerase, dNTPs), 0.25 µM Primer 1 (SEQ ID NO: 4), 0.25 µM of Primer 2 (SEQ ID NO: 5), and 2 µl of purified conjugated product (see Example 7) as template for amplification. The reaction mixture was thermally cycled by incubating the sample at 95° C. for 5 minutes, followed by 30 cycles of 98° C. for 20 seconds, 60° C. for 30 seconds, and 72° C. for 20 seconds. The amplification products were analyzed by gel electrophoresis (e.g., using an Agilent Bioanalyzer 2100 system and High-Sensitivity DNA Chip) to determine the size distributions of the reaction products.

Analysis of the amplification products indicated that the amplification reaction successfully produced amplicons using the conjugated products of the click chemistry reaction (see Example 7) as templates for amplification. In particular, analysis of the amplification products indicated that the polymerase processed along the template and through the triazole linkage to produce amplicons from the template. Further, the amplification produced a heterogeneous population of amplicons having a range of sizes corresponding to the expected sizes produced by amplification of the base-specific terminated DNA fragments via incorporation of the 3'-O-propargyl-dNTP. The fragment analysis also showed the proper fragment size increase corresponding to thirty one (31) additional bases from the conjugated 5'-azido-methyl-modified oligonucleotide.

Example 9—Ligation of NGS Adaptors to Fragment Ladder Products

Figure 5:
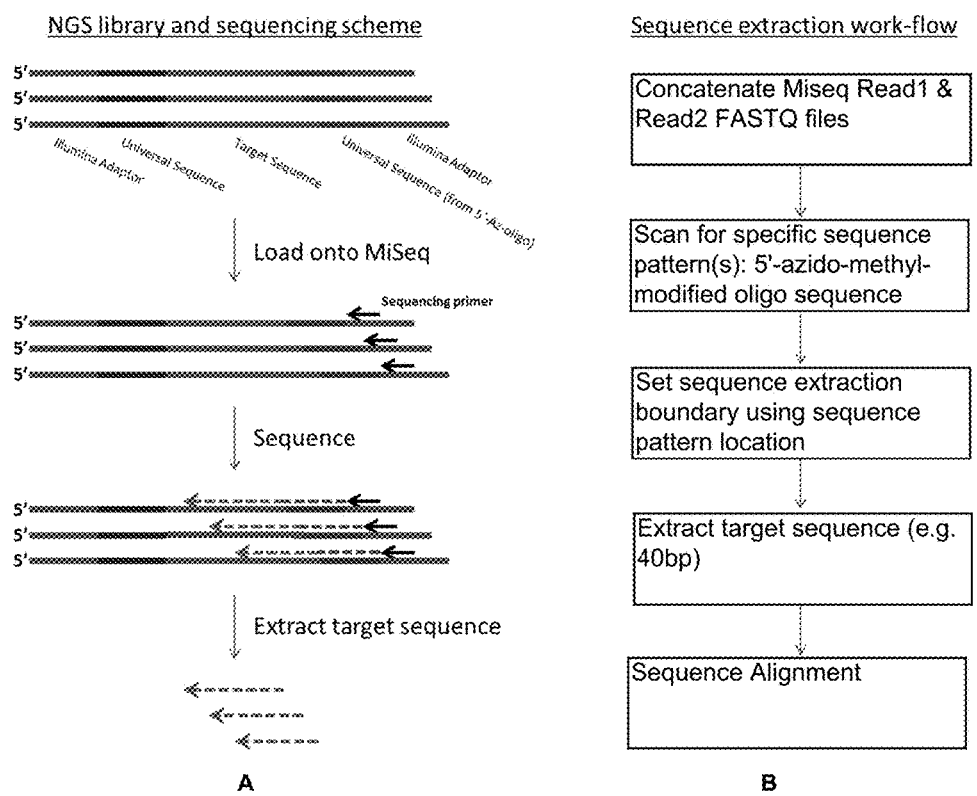
FIG. 5 shows flowcharts relating to embodiments of the technology that find use in sequencing a nucleic acid.

During the development of embodiments of the technology provided herein, experiments were conducted to sequence ladder fragments produced according to the technology provided herein (see FIG. 5). As an initial step in sequencing, experiments were conducted to prepare a sequencing library using DNA ladder products generated in Example 8 as input and a commercial kit for sample preparation. Sequencing libraries were prepared using a TRUSEQ NANO DNA sample preparation kit (Illumina, Inc.) following the manufacturer protocol with the following modification. After the adaptor ligation step, two rounds (instead of one round) of bead-based purification were performed using a 1:1 (v/v) sample to bead-mix ratio. 8 amplification cycles were performed using the provided Illumina PCR primers to enrich the adaptor-ligated products following the manufacturer protocol. The final sequencing library was analyzed by gel electrophoresis (Agilent 2100 Bioanalyzer and High Sensitivity DNA Assay Chip). Fragment size analysis confirmed the successful generation of a NGS library (e.g., for Illumina sequencing) using the fragment ladder products of Example 8. The data indicated that the NGS library had the proper fragment size increase corresponding to the addition of the 126-bp Illumina adaptors and thus that the adaptors were properly ligated to the fragment ladder. FIG. 5 shows a schematic of fragments of the sequencing library. In particular, the fragments comprise an Issumina adaptor on both ends, one or more universal sequence, and a target sequence.

Example 10—Sequencing

During the development of embodiments of the technology provided herein, experiments were conducted to sequence an adaptor-ligated NGS library, e.g., a sequencing library prepared as described in Example 9. The library produced according to Example 9 was successfully sequenced using an Illumina MiSeq sequencer using a 2×75-bp sequencing-by-synthesis kit. Sequencing primers complementary to the adaptor sequences are provided by the kit. After sequencing, more than 89% of the reads had a sequence quality score of Q30 or better.

Data collected from the experiments indicated that the fragment population provides for the unambiguous alignment of the short sequencing reads (30-50 bp) produced by the technology. In particular, the overlapping nucleic acid fragments provided reads that were successfully aligned and assembled despite their small size.

Sequence data were extracted from the sequencer output using a custom data processing work-flow that accommodates for the particular design of the fragment ladder produced according to the technology. For example, the custom software identified reads and processed reads to use 40-bp portions of the 2×75-bp sequence reads for subsequent sequence alignment. Particular components of the custom software concatenate reads (e.g., Read1 and Read2 FASTQ files) produced from the NGS sequencer; identify sequence originating from the target sequence, universal sequence, and adaptors (e.g., identify sequence originating from the 5'-azido-methyl-oligonucleotide); set a sequence extraction boundary using pattern recognition; extract the target sequence from the sequence reads produced from the NGS sequencer; and align the sequences (see FIG. 5).

Example 11—Sequence Alignment

During the development of embodiments of the technology provided herein, experiments were conducted to align sequence data produced from an NGS library as described herein, produce a consensus sequence from the alignment, and align the consensus sequence to a reference sequence. In particular, 40-bp sequence reads that were extracted from the MiSeq sequencing output were aligned against a reference sequence (e.g., a 177-bp sequence comprising human KRAS gene exon 2 partial flanking intron sequences).

Figure 6:
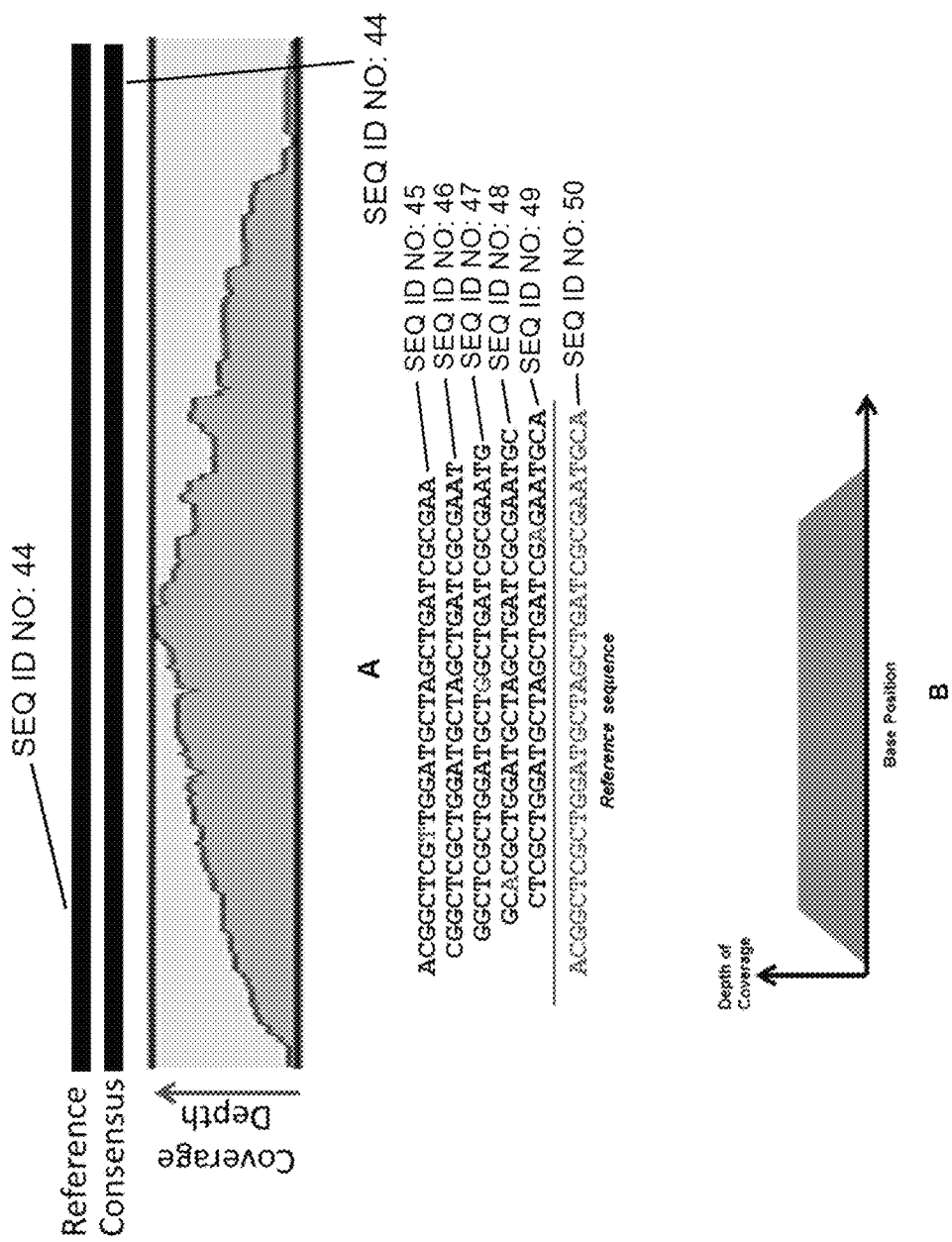
FIG. 6 shows predicted and experimental coverage of a target sequence by the short sequence reads produced by embodiments of the technology.

Alignment of the 40-bp sequencing reads was performed using CLC Genomics Workbench v7 with stringent penalties for mismatches and indels; length and similarity match requirements were appropriately set according to the accompanying instructions for 40-bp reads. The alignment results (FIG. 6A) indicated that 40-bp sequence reads provided complete coverage of the entire reference sequence (177 bp). Further, the plot of coverage depth versus sequence position had the expected "trapezoidal" coverage profile that was elucidated during theoretical alignment simulation (FIG. 6B).

These results indicate that a relatively short sequencing run (e.g. MiSeq with 30 to 50 sequencing-by-synthesis cycles) produces a complete, high-quality sequence of the target. Further, with adjustments to existing methods, e.g., designing primers to bind immediately adjacent to the target site, the length of high-quality sequence can be maximized. Further, the length of high-quality sequence can also be maximized with appropriate generation of the fragment ladder to cover the entire length of the entire length of the target (e.g., by adjusting the ratio of 3'-O-propargyl-dNTPs to dNTPs; see Example 12). In this example, 40 sequencing cycles (to obtain 40 bases of sequence) on the MiSeq took approximately 2.5 hours. Importantly, though, the technology provides an improvement over existing technologies in that the sequencer run-time does not change depending on the target size.

Example 12—Sequencing and Analysis of NGS Libraries

During the development of embodiments of the technology provided herein, experiments were conducted to control the size distribution of terminated nucleic acid fragments produced in a reaction comprising a mixture of 3'-O-propargyl-dNTPs and natural (standard) dNTPs by adjusting the ratio of 3'-O-propargyl-dNTPs to natural (standard) dNTPs. It was contemplated that the molar ratio of 3'-O-propargyl-dNTPs and natural dNTPs affects the fragment size distribution due to competition between the 3'-O-propargyl-dNTPs (that terminate extension) and natural dNTPs (that elongate the polymerase product) for incorporation into the synthesized nucleic acid by the polymerase.

Accordingly, experiments were performed in which the products of fragment ladder generation reactions were assessed at various molar ratios of 3'-O-propargyl-dNTPs to natural dNTPs. Fragment ladder generation reactions were performed using 2:1, 10:1, and 100:1 molar ratios of natural dNTPs to 3'-O-propargyl-dNTPs. The fragment generation reaction mixtures used in these experiments comprised 20 mM Tris-HCl, 10 mM $(NH_4)_2SO_4$, 10 mM KCl, 2 mM $MnCl_2$, 0.1% Triton X-100, 1000 pmol dATP, 1000 pmol dCTP, 1000 pmol dGTP, 1000 pmol dTTP, 6.25 pmol of primer, 2 units of Therminator II DNA polymerase (New England BioLabs), and 0.5 pmol of purified amplicon corresponding to a region in KRAS exon 2 (SEQ ID NO: 1) as template in a 25-µl final reaction volume.

In addition, reactions testing a 2:1 ratio of natural dNTPs to 3'-O-propargyl-dNTPs comprised 500 pmol of 3'-O-propargyl-dATP, 500 pmol of 3'-O-propargyl-dCTP, 500 pmol of 3'-O-propargyl-dGTP, and 500 pmol of 3'-O-propargyl-dTTP. Reactions testing a 10:1 ratio of natural dNTPs to 3'-O-propargyl-dNTPs comprised 100 pmol of 3'-O-propargyl-dATP, 100 pmol of 3'-O-propargyl-dCTP, 100 pmol of 3'-O-propargyl-dGTP, and 100 pmol of 3'-O-propargyl-dTTP. Reactions testing a 100:1 ratio of natural dNTPs to 3'-O-propargyl-dNTPs comprised 10 pmol of 3'-O-propargyl-dATP, 10 pmol of 3'-O-propargyl-dCTP, 10 pmol of 3'-O-propargyl-dGTP, and 10 pmol of 3'-O-propargyl-dTTP The polymerase extension reactions were temperature cycled by incubating at 95° C. for 2 minutes, followed by 45 cycles at 95° C. for 15 seconds, 55° C. for 25 seconds, and 65° C. for 35 seconds. After the polymerase extension reaction, 5'-azido-methyl-modified oligonucleotides were chemically conjugated to the nucleic acid fragments terminated with 3'-O-propargyl-dN using click chemistry as described in Example 6 and Example 7. After the conjugation, the conjugation products were used as templates for amplification to produce amplicons corresponding to the conjugated products as described in Example 8. Fragment size analysis was performed on the conjugated products.

Fragment size analysis of the amplified conjugation products produced from the products of the three different molar ratio conditions indicated that the fragment size depended on the ratio of 3'-O-propargyl-dNTPs to natural dNTPs. Analysis of the fragment sizes shows a fragment size distribution shift as a function of the molar ratios of dNTP to 3'-O-propargyl-dNTP. At the 2:1 molar ratio, larger populations of shorter fragments were detected compared to the other two molar ratio conditions. At the 10:1 molar ratio, a larger fraction of longer fragments was present relative to the 2:1 molar ratio. At the 100:1 molar ratio, the major population of fragments comprised longer DNA fragments relative to the other two molar ratios.

The ladder fragments produced with the three different molar ratios were used as separate inputs to generate NGS (Illumina) libraries for sequencing on the MiSeq sequencer as described in Example 9. Furthermore, sequence reads were obtained as described in Example 10 and sequence data from the target sequence was extracted and analyzed as described in Example 11.

The coverage profiles of the three libraries that were prepared using the three different molar ratios of dNTP to 3'-O-propargyl-dNTP (molar ratios of 2:1, 10:1, and 100:1) correlated with the DNA ladder fragment size distribution created by the respective molar ratios. For example, the 2:1 molar ratio of dNTP to 3'-O-propargyl-dNTP was expected to terminate polymerase extension at a high frequency due to the relatively high abundance of 3'-O-propargyl-dNTP and thus produce nucleic acid ladder fragments that are relatively shorter that at higher ratios of dNTP to 3'-O-propargyl-dNTP. In contrast, the 100:1 molar ratio was expected to terminate polymerase extension at a low frequency due to the relatively low abundance of 3'-O-propargyl-dNTP and thus produce nucleic acid ladder fragments that are relatively longer that at lower ratios of dNTP to 3'-O-propargyl-dNTP.

The data collected from the fragment size analysis of the DNA ladder products generated using the three different molar ratios confirmed these predictions. In particular, the data indicate that varying the molar ratio of dNTP to 3'-O-propargyl-dNTP provides for the control of DNA ladder fragment size.

Furthermore, sequencing of the DNA ladder products generated using the three different molar ratios and analysis of the sequence produced from the ladder products showed that the sequence coverage profiles correlated with the molar ratio of dNTP to 3'-O-propargyl-dNTP used during DNA ladder generation. In particular, the data indicated that the 2:1 molar ratio provided more coverage of sequence near the binding site of the sequencing primer and the 100:1 molar ratio provided more coverage further from the binding site of the sequencing primer. Accordingly, the technology provides the ability to control DNA ladder fragment generation for a variety of sequencing applications. In particular, increasing coverage distant from the sequencing primer binding site is useful for sequencing applications related to long (e.g., greater than 100 base pairs) sequencing applications. Sequencing using multiple sequencing libraries produced at different molar ratios provides sequence data having high coverage of sequences that are near, intermediate, and far from the binding site of the sequencing primer.

Example 13—Tagging with Primers Comprising an Index Sequence

During the development of embodiments of the technology provided herein, experiments were conducted to assess the use of index or barcode sequences to track and construct the sequence of the original target template from the sequence produced from library generation, NGS, and alignment. In the first set of experiments, target nucleic acids were copied and tagged by polymerase extension reactions using target-specific primers comprising a uniquely identifying index sequence. As used herein, this and similar molecular barcoding approaches are referred to as a "copy and tag reaction" or a "copy and ID-tag reaction".

Figure 7:
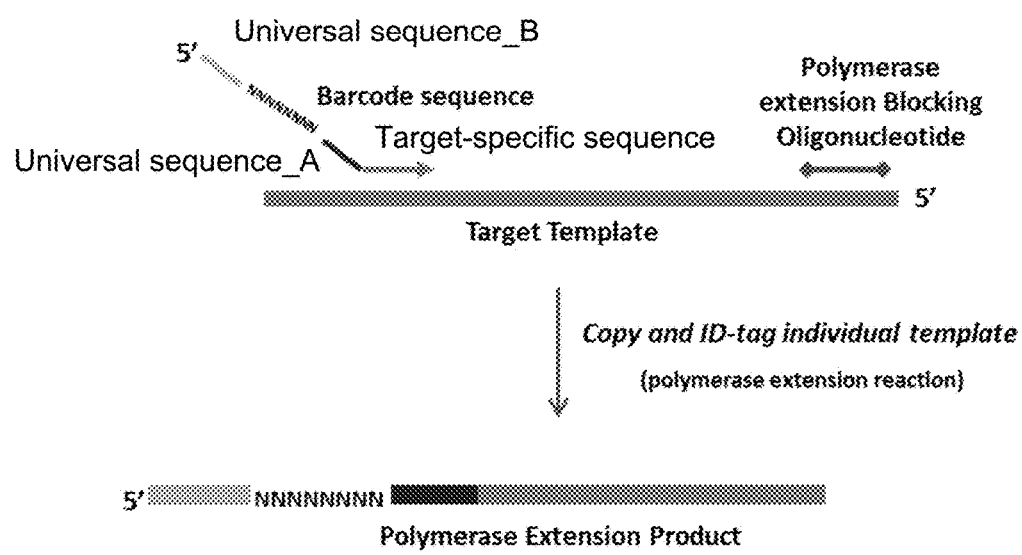
FIG. 7 shows a schematic of an embodiment of the technology related to a "copy and tag" scheme using polymerase extension of a primer comprising a barcode sequence and universal sequences.

In this scheme, a polymerase extension primer was designed that comprises two regions (FIG. 7): a 3' region comprising a target-specific priming sequence and a 5' region comprising two different universal sequences (e.g., universal sequence A and universal sequence B) flanking a degenerate sequence (e.g., comprising 8 bp). Oligonucleotide primers were synthesized according to this scheme and used in polymerase extension reactions with a second oligonucleotide designed to stop the polymerase extension and thus "copy and tag" only the target region of interest:

```
polymerase extension primer Eg_e19_R_SOD_v03-01-
bio
                                      (SEQ ID NO: 6)
bTAAUTAGTGGCTGACGGGTATCTCTCACCTTTNNNNNNNNNCAGACATGA

GAAAAGGTGGGC polymerase extension blocker Eg_e19_SOD_SC-200_v1
                                      (SEQ ID NO: 7)
C*A*ATTGTGAGATGGTGCCACATGCTGCam
```

In the sequences of the polymerase extension primer and polymerase extension blocker used in polymerase extension reaction during "copy and tag" procedure (SEQ ID NOs: 6 and 7 above), a "b" indicates a 5'-biotin modification, a "U" indicates a deoxyuridine modification, a "*" indicates a phosphorothioate bond, and "am" indicates a 3'-amino modification.

Polymerase extension reactions were performed using a commercially available high-fidelity polymerase master mix kit (KAPA HiFi HotStart PCR kit, KAPA Biosystems) to produce a reaction mixture comprising 1 pmol of polymerase extension primer (e.g., Eg_e19_R_SOD_v03-01-bio), 1 pmol of polymerase extension blocker (e.g., Eg_e19_SOD_SC-200_v1), and 100 ng of purified genomic DNA extracted from a human lung adenocarcinoma/non-small cell lung cancer cell line (Cell line NCI-H1975 available from ATCC under accession CRL-5908) in a 25-µl reaction volume. Polymerase extension reactions were incubated at 95° C. for 2 minutes, 98° C. for 30 seconds, 58° C. for 90 seconds, and 65° C. for 30 seconds. The dNTP and KAPA HiFi polymerase were added immediately after the completion of the 58° C. incubation step.

The polymerase extension reaction products were purified using bead-based purification (Ampure XP, Beckman Coulter) following the manufacturer protocol to remove polymerase extension primers, polymerase extension blockers, and other extension reaction components. Then, a solid phase capture-based purification using streptavidin-coated magnetic microspheres (Dynabeads, MyOne Streptavidin C1, Life Technologies) was used to isolate the polymerase extension reaction products from the genomic DNA template. After isolating the polymerase extension reaction products, a 2× binding and wash buffer (2 M NaCl, 20 mM Tris-HCl, 2 mM EDTA, pH 7.5) was added to the eluent from the bead purification at a 1:1 (v/v) ratio and incubated with the streptavidin beads at ambient (room) temperature for 15 minutes. The beads were separated from the supernatant using a magnet and the supernatant was removed. Next, the beads were washed twice using binding and wash buffer and resuspended in 25 µl of TE buffer (10 mM Tris-HCl, 0.1 mM EDTA, pH approximately 8). The beads were incubated with a solution of 0.1 M NaOH and 0.1 M NaCl for 1 minute to remove any traces of remaining genomic DNA. The beads were then separated from the supernatant using a magnet (the supernatant was discarded), the beads were washed twice using binding and wash buffer, and resuspended in 25 µl of TE buffer (10 mM Tris-HCl, 0.1 mM EDTA, pH approximately 8).

Finally, to release the bead-bound product, a uracil cleavage system (Uracil Glycosylase and Endonuclease VIII, Enzymatics) was used to cleave the bead-bound polymerase extension product at the deoxyuridine modification incorporated into the 5' end of the polymerase extension product as a result of extension of the polymerase extension primer (see SEQ ID NO: 6). The supernatant comprising the polymerase extension product was purified using Ampure XP (Beckman Coulter) following the manufacturer protocol and eluted in 20 µl of TE buffer.

Figure 8:
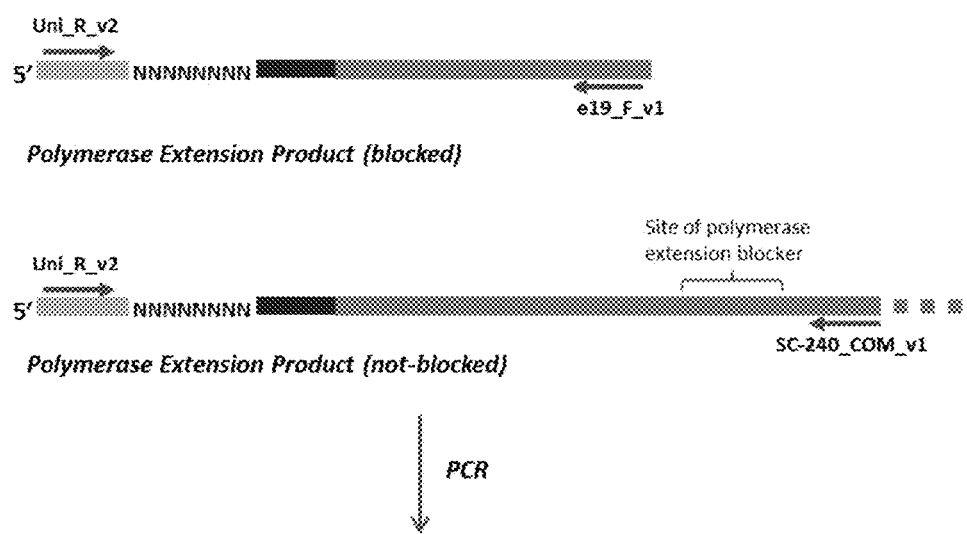
FIG. 8 shows a scheme for the experimental detection of "copy and tag" reaction products and for evaluation the effectiveness of the polymerase extension blocker.

Amplification primers Uni_R_v2 and e19_F_v1 were designed, synthesized, and used to amplify the purified polymerase extension product to confirm generation of the copy and tag product as described schematically in FIG. 8. Amplification primers Uni_R_v2 and SC-240_COM_v1 were used to confirm that the polymerase extension blocker effectively blocked polymerase extension past the site at which the polymerase extension blocker binds to the template.

```
Uni_R_v2
                                         (SEQ ID NO: 8)
AGTGGCTGACGGGTATCTCTC e19_F_v1
                                         (SEQ ID NO: 9)
TGCCAGTTAACGTCTTCCTTCT

SC-240_COM_v1
                                         (SEQ ID NO: 10)
ATCACTGGGCAGCATGTGG
```

Two amplification reactions were performed on the polymerase extension product. A first reaction comprised the primers Uni_R_v2 and e19_F-v1, which amplify both blocked (via polymerase extension blocker) and non-blocked polymerase extension products. A second reaction comprised the primers Uni_R_v2 and SC-240_COM_v1, which amplify only non-blocked polymerase extension product. The two types of reaction mixtures were produced using a commercially available amplification mix (KAPA 2G HS, KAPA Biosystems) and 0.25 µM of each primer (as indicated above for the two reactions) in a 25-µl final reaction volume. A 5-µl volume of purified polymerase extension product was used as template for each amplification reaction. The amplification reactions were thermocycled by incubating the reaction mixtures at 95° C. for 5 minutes, followed by 30 cycles of 98° C. for 20 seconds, 60° C. for 30 seconds, and 72° C. for 20 seconds. The amplification products were analyzed by gel electrophoresis (e.g., using an Agilent Bioanalyzer 2100 system and a High-Sensitivity DNA chip) to determine the fragment size distributions.

Data collected from fragment size analysis indicated that the amplification reaction comprising primers Uni_R_v2 and e19_F_v1 produced a product of the expected size. Furthermore, the data also indicated that the amplification reaction comprising primers Uni_R_v2 and SC-240_COM_v1 did not generate a detectable product, thus indicating that the polymerase extension blocker effectively stop the polymerase reaction. Accordingly, the technology provides for precise control of the copy and tag reaction to produce products only from a target region of interest.

Example 14—Tagging with Adaptors Comprising an Index Sequence

Further, in a second set of experiments conducted during the development of embodiments described herein, target nucleic acids were copied and subsequently tagged by adaptor ligation using adaptors comprising a uniquely identifying index sequence. In this molecular barcoding scheme based on adaptor ligation (see, e.g., FIG. 9), a DNA adaptor was constructed using two oligonucleotides. The first oligonucleotide was designed to have a stretch of degenerate sequence (e.g., comprising 8 to 12 bases) flanked on both the 5' end and the 3' end by two different universal sequences (e.g., universal sequence A and universal sequence B; see FIG. 9). The second oligonucleotide was designed to comprise a universal sequence C (e.g., at the 5' end) and a sequence (e.g., at the 3' end) that is complementary to universal sequence B and that has an additional T at the 3'-terminal position. To produce the DNA adaptor, the two oligonucleotides were mixed in equal molar amounts, incubated at 95° C. for 5 minutes, and then cooled slowly to ambient (room) temperature to provide for efficient hybridization of the complementary portions of the two oligonucleotides (e.g., universal sequence B and its complementary sequence). Ligation of these adaptors to target DNA provides for the unique 'ID-tagging' of each individual target DNA molecule (e.g., each individual PCR amplicon), e.g., in a reaction comprising a molar excess of unique ID-tag sequence adaptors relative to the number of individual target molecules.

Experiments were conducted to tests embodiments of this technology using the following oligonucleotides:

```
ST-adN10-phos-v1
                                      (SEQ ID NO: 11)
pGTGGCTGACGGGTATCTCTCNNNNNNNNNNATCACCGACTGCCCATAGA

GAGG

ST-ad-T-v1
                                      (SEQ ID NO: 12)
GCACTGGATCACGTCATACCTACGAGAGATACCCGTCAGCCA*C*T
```

In the sequences of the two oligonucleotides used to form the adaptor (SEQ ID NOs: 11 and 12 above), a "p" indicates a 5'-phosphate modification, an "N" indicates a degenerate base position (e.g., the position can be A, C, G, or T), and a "f" indicates a phosphorothioate bond.

As a first step, an amplification reaction was performed to amplify a 158-bp region in exon 18 (with flanking intron sequence) of the human EGFR gene using the following primers:

```
E_e18_f_v1p
                                      (SEQ ID NO: 13)
pCCAGTGGAGAAGCTCCCAAC

E_e18_r_v1p
                                      (SEQ ID NO: 14)
pCAGACCATGAGAGGCCCTG
```

In the sequences of the two EGFR primers (SEQ ID NOs: 13 and 14 above), a "p" indicates a 5'-phosphate modification. Reaction mixtures were produced using a commercially available PCR master mix kit (KAPA 2G HotStart PCR kit, KAPA Biosystems), 10 pmol each of the EGFR primers (SEQ ID NOs: 13 and 14), and 10 ng of purified genomic DNA extracted from a human lung adenocarcinoma/non-small cell lung cancer cell line (Cell line NCI-H1975 available from ATCC under accession CRL-5908) in 25-µl reaction volume. The reaction mixtures were thermocycled by incubating at 95° C. for 2 minutes, followed by 23 cycles of 98° C. for 20 seconds, 63° C. for 30 seconds, and 68° C. for 20 seconds. After amplification, 1 µl of the reaction mix was used directly for DNA fragment size analysis using gel electrophoresis (e.g., Agilent 2100 Bioanalyzer and High Sensitivity DNA Assay Chip). Data collected from fragment analysis indicated that the amplification generated a product having the expected size of 158 bp.

Next, the amplification product was purified to remove unincorporated primers and amplification reaction components using a bead-based purification method (Ampure XP, Beckman Coulter) following the manufacturer protocol.

After purification, an adaptor comprising an index sequence (e.g., as described above) was ligated to the amplicon. The amplicon produced by the amplification reaction above comprised a 5' phosphate (e.g., from incorporation of the 5'-phosphate modified primers) and a 3'-dA-overhang (e.g., from a DNA polymerase that adds a non-templated A at the 3'-end of extension products). The ligation reaction was performed using a commercially available ligation kit (T4 DNA Ligase-Rapid, Enzymatics). In particular, a ligation reaction mixture was produced using the kit "Rapid" ligation buffer, 25 pmol of adaptor, and approximately 0.25 pmol of the amplicon in a 50-µl reaction volume.

After the ligation reaction, the ligation reaction mix was incubated at 25° C. for 10 minutes and immediately purified twice using bead-based purification (Ampure XP, Beckman Coulter) following the manufacturer protocol except that the sample input volume to bead solution volume was changed from 1:1.8 to 1:1.

Figure 10:
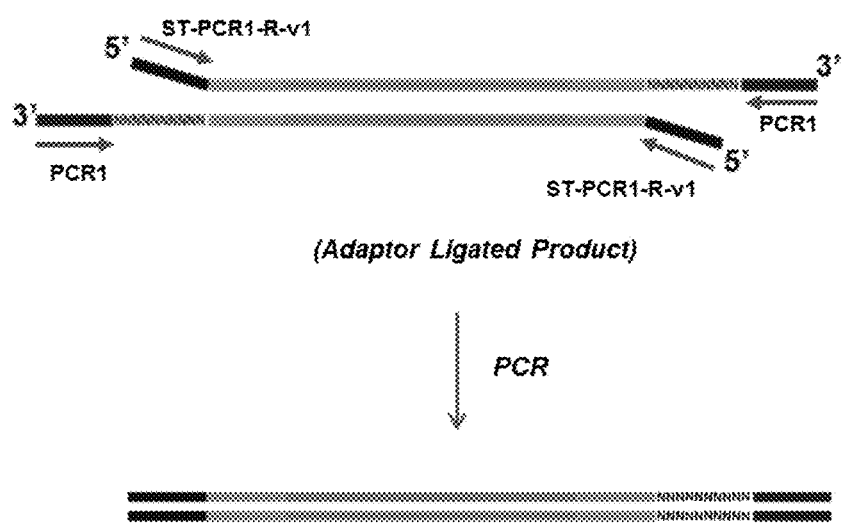
FIG. 10 shows a scheme for the experimental detection of adaptor ligated products.

The purified ligated product was used as a template in a limited-cycle (e.g., 8-cycle) enrichment amplification to amplify the ligated product (FIG. 10). The amplification reaction comprised primers designed to amplify the ligated product comprising the 'ID-tag' tag portion (e.g., 10 degenerate bases) and having an expected length of 249 bp:

```
PCR1
                                      (SEQ ID NO: 15)
CCTCTCTATGGGCAGTCGGTGAT

ST-PCR1-R-v1
                                      (SEQ ID NO: 16)
GCACTGGATCACGTCATACCTAC
```

The amplification was performed using a commercially available high-fidelity polymerase PCR master mix kit (KAPA HiFi HotStart PCR kit, KAPA Biosystems) to produce a reaction mixture comprising 0.25 µM of each primer and the purified adaptor-ligated product as template in a 25-µl reaction volume. The amplification reaction mixtures were thermocycled by incubating at 95° C. for 5 minutes, followed by 8 cycles of 98° C. for 20 seconds, 60° C. for 30 seconds, and 72° C. for 20 seconds. After amplification, 1 µl of the reaction mix was used directly for fragment size analysis by gel electrophoresis (Agilent 2100 Bioanalyzer and High Sensitivity DNA Assay Chip. Data collected from the fragment analysis indicated that the amplification produced an amplicon of the expected size from the adaptor-ligated product (e.g., a 249-bp amplicon comprising a portion corresponding to the EGFR amplicon of 158 bp produced above and a ligated adaptor).

Example 15—Circularization of Target Nucleic Acid

Figure 11:
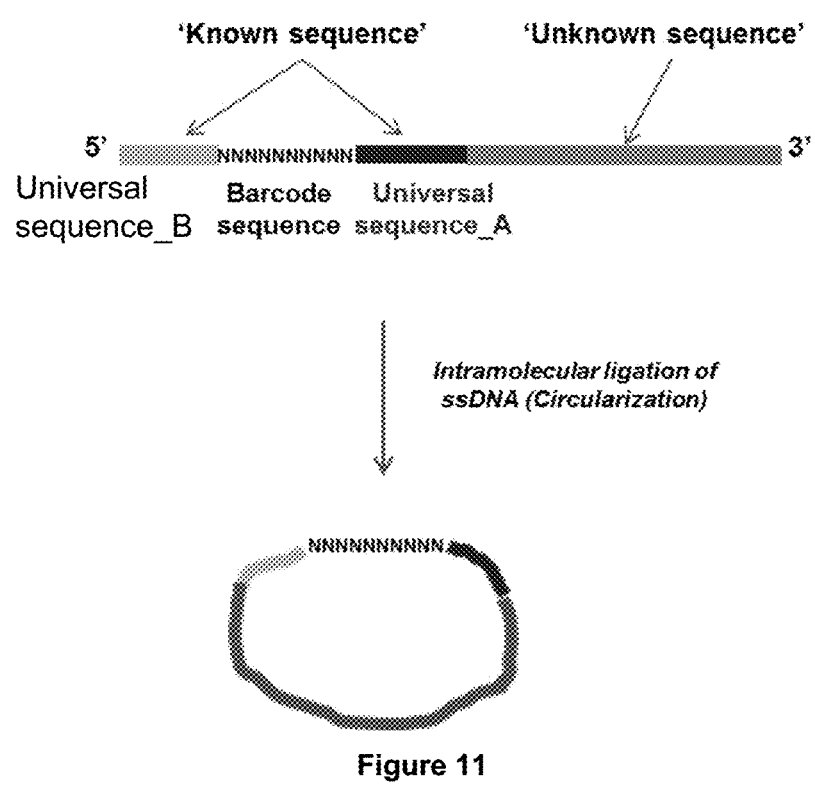
FIG. 11 shows a scheme for intramolecular ligation (circularization) of single stranded DNA as a step in generating ladder fragments according to the technology provided herein.

During the development of embodiments of the technology provided herein, experiments were conducted to evaluate a molecular technique based on intramolecular ligation (circularization) of target nucleic acid to orient different regions of the target nucleic acid in a specific arrangement. The method comprises circularizing a target nucleic acid, which places a known sequence (e.g., a universal priming sequence) adjacent to an unknown sequence (e.g., a region of interest to query, e.g., by sequencing) in specific orientation (FIG. 11).

In these experiments, the circularization reactions were performed using a commercially available ssDNA ligase kit (CircLigase II, Epicentre-Illumina) following the manufacturer protocol. The experiments tested synthetic input templates that were oligonucleotides ("ultramers") having lengths of 100, 150 and 200 bases:

```
Ultramer-200 bp
                                      (SEQ ID NO: 17)
pGCAGCATGTGGCACCATCTCACAATTGCCAGTTAACGTCTTCCTTCTCT

CTGGTGAGAAAGTTAAAATTCCCGTCGCTATCAAGGAATTAAGAGAAGCA
```

-continued

ACATCTCCGAAAGCCAACAAGGAAATCCTCGATGTGAGTTTCTGCTTTGC

TGTGTGGGGGTCCATGGCTCTGAACCTCAGGCCCACCTTTTCTCATGTCT

G

Ultramer-150 bp (SEQ ID NO: 18)

pGCAGCATGTGGCACCATCTCACAATTGCCAGTTAACGTCTTCCTTCTCT

CTATCTCCGAAAGCCAACAAGGAAATCCTCGATGTGAGTTTCTGCTTTGC

TGTGTGGGGGTCCATGGCTCTGAACCTCAGGCCCACCTTTTCTCATGTCT

G

Ultramer-100 bp (SEQ ID NO: 19)

pGCAGCATGTGGCACCATCTCACAATTGCCAGTTAACGTCTTCCTTCTCT

CTGATGTGAGTTTCTGCTTTGCTTCCTCAGGCCCACCTTTTCTCATGTCT

G

In the sequences of the ultramers (SEQ ID NOs: 17, 18, and 19 above), a "p" indicates a 5'-phosphate modification.

Figure 12:
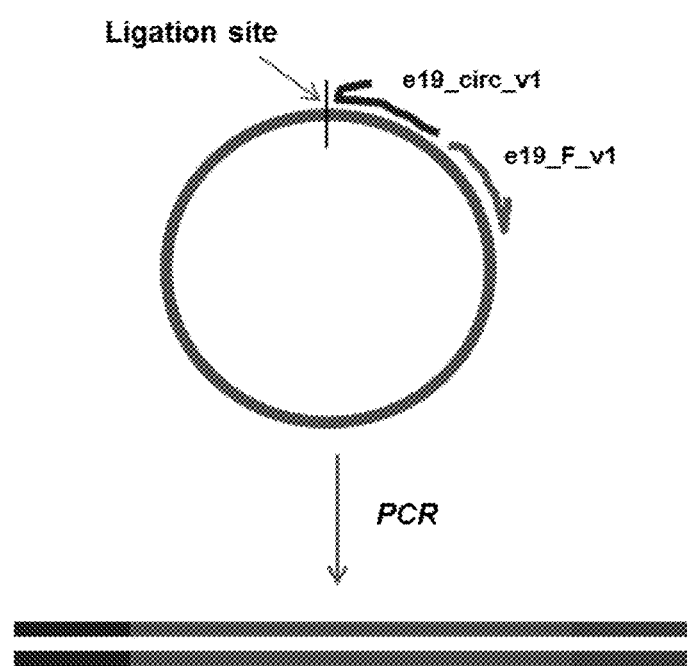
FIG. 12 shows a scheme for the experimental detection of circular templates related to embodiments of the technology related to the generation of circular templates for fragment ladder generation.

After the circularization reaction, the products were treated with exonuclease I and III (NEB) for 30 minutes at 37° C. to remove non-circularized template. After exonuclease treatment, the exonucleases were inactivated by incubating at 80° C. for 10 minutes. To confirm circularization of the templates, primers were designed to amplify circle-specific amplification products (FIG. 12):

e19_F_v1

(SEQ ID NO: 20)

TGCCAGTTAACGTCTTCCTTCT e19_circ_v1

(SEQ ID NO: 21)

G*A*TGGTGCCACATGCTGC

In the sequences of the circular template primers (SEQ ID NOs: 20 and 21 above), a "*" indicates a phosphorothioate bond.

Amplification reaction mixtures were produced using Taq-Gold (Abbott Molecular), 0.2 µM of each primer, and one of the three differently sized reaction products as template in a 25-µl reaction volume. The reaction mixtures were thermocycled by incubating at 95° C. for 5 minutes, followed by 38 cycles of 98° C. for 20 seconds, 60° C. for 30 seconds, and 68° C. for 30 seconds. After amplification, 10 µl of the reaction mix was used directly for DNA fragment size analysis by gel electrophoresis using pre-cast 2% agarose gels (E-Gel EX 2% Agarose Gel, Life Technologies). The data collected indicated that the amplification produced a product of the expected size from the circular templates, thus confirming the generation of circular nucleic acids from the three test ultramers. Furthermore, the absence of circle-specific products in negative controls comprising linear templates indicates that the primers produce circle-specific products.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method of generating a sequencing library, the method comprising:
   a) amplifying a target nucleotide sequence using a primer comprising a target specific sequence and a universal sequence A to provide an amplicon, wherein the amplicon may be single stranded or double stranded;
   b) ligating a first adaptor oligonucleotide comprising a universal sequence B to the amplicon to form an adaptor-amplicon; and
   c) generating a ladder fragment library for use as a sequencing library, wherein said ladder fragment library comprises a plurality of nucleic acid fragments terminated by a 3'-O-propargyl nucleotide.

2. The method of claim 1 wherein the primer further comprises a barcode nucleotide sequence associated with the target nucleic acid.

3. The method of claim 2 wherein the barcode nucleotide sequence comprises 1 to 20 nucleotides.

4. The method of claim 1 wherein the first adaptor oligonucleotide is ligated to the 3' end of the amplicon.

5. The method of claim 1 further comprising circularizing the adaptor-amplicon to form a circular template.

6. The method of claim 1 further comprising ligating a second adaptor oligonucleotide comprising a universal sequence C to the 3' ends of the fragments of the ladder fragment library to generate a sequencing library.

7. The method of claim 6 comprising use of a click chemistry reaction to ligate the second adaptor oligonucleotide comprising a universal sequence C to the 3' ends of the fragments of the ladder fragment library to generate the sequencing library.

8. The method of claim 1 wherein the first adaptor oligonucleotide comprises 10 to 80 nucleotides.

9. The method of claim 1, wherein the nucleotide sequences of the fragments of the ladder fragment library correspond to overlapping nucleotide subsequences within the target nucleotide sequence and the nucleotide sequences of the fragments have 3' ends corresponding to different nucleotides of the target nucleotide sequence.

10. The method of claim 1 wherein each nucleotide sequence of each fragment of the ladder fragment library comprises 15 to 1,000 nucleotides.

11. The method of claim 1 wherein generating said ladder fragment library comprises using a primer complementary to said universal sequence A.

* * * * *

SEQUENCE LISTING

```
<160> NUMBER OF SEQ ID NOS: 50

<210> SEQ ID NO 1
<211> LENGTH: 177
<212> TYPE: DNA
<213> ORGANISM: HOMO SAPIENS

<400> SEQUENCE: 1
ttattataag gcctgctgaa aatgactgaa tataaacttg tggtagttgg agctggtggc     60
gtaggcaaga gtgccttgac gatacagcta attcagaatc attttgtgga cgaatatgat    120
ccaacaatag aggtaaatct tgttttaata tgcatattac tggtgcagga ccattct        177

<210> SEQ ID NO 2
<211> LENGTH: 48
<212> TYPE: DNA
<213> ORGANISM: ARTIFICIAL
<220> FEATURE:
<223> OTHER INFORMATION: synthetic

<400> SEQUENCE: 2
taaucctctc tatgggcagt cggtgataga atggtcctgc accagtaa                  48

<210> SEQ ID NO 3
<211> LENGTH: 32
<212> TYPE: DNA
<213> ORGANISM: ARTIFICIAL
```

<220> FEATURE:
<223> OTHER INFORMATION: synthetic

<400> SEQUENCE: 3
tctgagtcgg agacacgcag ggatgagatg gt         32

<210> SEQ ID NO 4
<211> LENGTH: 23
<212> TYPE: DNA
<213> ORGANISM: ARTIFICIAL
<220> FEATURE:
<223> OTHER INFORMATION: synthetic

<400> SEQUENCE: 4
cctctctatg ggcagtcggt gat         23

<210> SEQ ID NO 5
<211> LENGTH: 22
<212> TYPE: DNA
<213> ORGANISM: ARTIFICIAL
<220> FEATURE:
<223> OTHER INFORMATION: synthetic

<400> SEQUENCE: 5
ccatctcatc cctgcgtgtc tc         22

<210> SEQ ID NO 6
<211> LENGTH: 61
<212> TYPE: DNA
<213> ORGANISM: ARTIFICIAL
<220> FEATURE:
<223> OTHER INFORMATION: synthetic
<220> FEATURE:
<221> NAME/KEY: misc_feature
<222> LOCATION: (33)..(40)
<223> OTHER INFORMATION: n is a, c, g, t or u

<400> SEQUENCE: 6
taautagtgg ctgacgggta tctctcacct ttnnnnnnnn cagacatgag aaaaggtggg    60
c                                                                   61

<210> SEQ ID NO 7
<211> LENGTH: 27
<212> TYPE: DNA
<213> ORGANISM: ARTIFICIAL
<220> FEATURE:
<223> OTHER INFORMATION: synthetic

<400> SEQUENCE: 7
caattgtgag atggtgccac atgctgc         27

<210> SEQ ID NO 8
<211> LENGTH: 21
<212> TYPE: DNA
<213> ORGANISM: ARTIFICIAL
<220> FEATURE:
<223> OTHER INFORMATION: synthetic

<400> SEQUENCE: 8
agtggctgac gggtatctct c         21

<210> SEQ ID NO 9
<211> LENGTH: 22
<212> TYPE: DNA
<213> ORGANISM: ARTIFICIAL
<220> FEATURE:

<223> OTHER INFORMATION: synthetic

<400> SEQUENCE: 9
tgccagttaa cgtcttcctt ct                                              22

<210> SEQ ID NO 10
<211> LENGTH: 19
<212> TYPE: DNA
<213> ORGANISM: ARTIFICIAL
<220> FEATURE:
<223> OTHER INFORMATION: synthetic

<400> SEQUENCE: 10
atcactgggc agcatgtgg                                                  19

<210> SEQ ID NO 11
<211> LENGTH: 53
<212> TYPE: DNA
<213> ORGANISM: ARTIFICIAL
<220> FEATURE:
<223> OTHER INFORMATION: synthetic
<220> FEATURE:
<221> NAME/KEY: misc_feature
<222> LOCATION: (21)..(30)
<223> OTHER INFORMATION: n is a, c, g, or t

<400> SEQUENCE: 11
gtggctgacg ggtatctctc nnnnnnnnnn atcaccgact gcccatagag agg            53

<210> SEQ ID NO 12
<211> LENGTH: 44
<212> TYPE: DNA
<213> ORGANISM: ARTIFICIAL
<220> FEATURE:
<223> OTHER INFORMATION: synthetic

<400> SEQUENCE: 12
gcactggatc acgtcatacc tacgagagat acccgtcagc cact                      44

<210> SEQ ID NO 13
<211> LENGTH: 20
<212> TYPE: DNA
<213> ORGANISM: ARTIFICIAL
<220> FEATURE:
<223> OTHER INFORMATION: synthetic

<400> SEQUENCE: 13
ccagtggaga agctcccaac                                                 20

<210> SEQ ID NO 14
<211> LENGTH: 19
<212> TYPE: DNA
<213> ORGANISM: ARTIFICIAL
<220> FEATURE:
<223> OTHER INFORMATION: synthetic

<400> SEQUENCE: 14
cagaccatga gaggccctg                                                  19

<210> SEQ ID NO 15
<211> LENGTH: 23
<212> TYPE: DNA
<213> ORGANISM: ARTIFICIAL
<220> FEATURE:
<223> OTHER INFORMATION: synthetic

<400> SEQUENCE: 15

```
cctctctatg ggcagtcggt gat                                              23
```

<210> SEQ ID NO 16
<211> LENGTH: 23
<212> TYPE: DNA
<213> ORGANISM: ARTIFICIAL
<220> FEATURE:
<223> OTHER INFORMATION: synthetic

<400> SEQUENCE: 16

```
gcactggatc acgtcatacc tac                                              23
```

<210> SEQ ID NO 17
<211> LENGTH: 200
<212> TYPE: DNA
<213> ORGANISM: ARTIFICIAL
<220> FEATURE:
<223> OTHER INFORMATION: synthetic

<400> SEQUENCE: 17

```
gcagcatgtg gcaccatctc acaattgcca gttaacgtct tccttctctc tggtgagaaa      60
gttaaaattc ccgtcgctat caaggaatta agagaagcaa catctccgaa agccaacaag     120
gaaatcctcg atgtgagttt ctgctttgct gtgtggggt ccatggctct gaacctcagg      180
cccacctttt ctcatgtctg                                                 200
```

<210> SEQ ID NO 18
<211> LENGTH: 150
<212> TYPE: DNA
<213> ORGANISM: ARTIFICIAL
<220> FEATURE:
<223> OTHER INFORMATION: synthetic

<400> SEQUENCE: 18

```
gcagcatgtg gcaccatctc acaattgcca gttaacgtct tccttctctc tatctccgaa      60
agccaacaag gaaatcctcg atgtgagttt ctgctttgct gtgtggggt ccatggctct     120
gaacctcagg cccacctttt ctcatgtctg                                      150
```

<210> SEQ ID NO 19
<211> LENGTH: 100
<212> TYPE: DNA
<213> ORGANISM: ARTIFICIAL
<220> FEATURE:
<223> OTHER INFORMATION: synthetic

<400> SEQUENCE: 19

```
gcagcatgtg gcaccatctc acaattgcca gttaacgtct tccttctctc tgatgtgagt      60
ttctgctttg cttcctcagg cccacctttt ctcatgtctg                           100
```

<210> SEQ ID NO 20
<211> LENGTH: 22
<212> TYPE: DNA
<213> ORGANISM: ARTIFICIAL
<220> FEATURE:
<223> OTHER INFORMATION: synthetic

<400> SEQUENCE: 20

```
tgccagttaa cgtcttcctt ct                                               22
```

<210> SEQ ID NO 21
<211> LENGTH: 18
<212> TYPE: DNA

```
<213> ORGANISM: ARTIFICIAL
<220> FEATURE:
<223> OTHER INFORMATION: synthetic

<400> SEQUENCE: 21
gatggtgcca catgctgc                                                     18

<210> SEQ ID NO 22
<211> LENGTH: 169
<212> TYPE: DNA
<213> ORGANISM: HOMO SAPIENS

<400> SEQUENCE: 22
gaactacttg gaggaccgtc gcttggtgca ccgcgacctg gcagccagga acgtactggt        60
gaaaacaccg cagcatgtca agatcacaga ttttgggctg gccaaactgc tgggtgcgga       120
agagaaagaa taccatgcag aaggaggcaa agtaaggagg tggctttag                   169

<210> SEQ ID NO 23
<211> LENGTH: 120
<212> TYPE: DNA
<213> ORGANISM: HOMO SAPIENS

<400> SEQUENCE: 23
gacctggcag ccaggaacgt actggtgaaa acaccgcagc atgtgcaaga tcacagattt        60
tgggctggcc aaactgctgg gtgcggaaga gaaagaatac catgcagaag gaggcaaagt       120

<210> SEQ ID NO 24
<211> LENGTH: 35
<212> TYPE: DNA
<213> ORGANISM: HOMO SAPIENS
<220> FEATURE:
<221> NAME/KEY: misc_feature
<222> LOCATION: (35)..(35)
<223> OTHER INFORMATION: n is a, c, g, or t

<400> SEQUENCE: 24
gcagcatgtc aagatcacag attttgggct ggccn                                   35

<210> SEQ ID NO 25
<211> LENGTH: 35
<212> TYPE: DNA
<213> ORGANISM: HOMO SAPIENS

<400> SEQUENCE: 25
gcagcatgtc aagatcacag attttgggct ggcca                                   35

<210> SEQ ID NO 26
<211> LENGTH: 35
<212> TYPE: DNA
<213> ORGANISM: HOMO SAPIENS
<220> FEATURE:
<221> NAME/KEY: misc_feature
<222> LOCATION: (35)..(35)
<223> OTHER INFORMATION: n is a, c, g, or t

<400> SEQUENCE: 26
cagcatgtca agatcacaga ttttgggctg gccan                                   35

<210> SEQ ID NO 27
<211> LENGTH: 35
<212> TYPE: DNA
<213> ORGANISM: HOMO SAPIENS
<220> FEATURE:
<221> NAME/KEY: misc_feature
```

```
<222> LOCATION: (1)..(4)
<223> OTHER INFORMATION: n is a, c, g, or t

<400> SEQUENCE: 27
nnnncatgtc aagatcacag attttgggct ggcca                              35

<210> SEQ ID NO 28
<211> LENGTH: 35
<212> TYPE: DNA
<213> ORGANISM: HOMO SAPIENS

<400> SEQUENCE: 28
cagcatgtca agatcacaga ttttgggctg gccaa                              35

<210> SEQ ID NO 29
<211> LENGTH: 35
<212> TYPE: DNA
<213> ORGANISM: HOMO SAPIENS
<220> FEATURE:
<221> NAME/KEY: misc_feature
<222> LOCATION: (35)..(35)
<223> OTHER INFORMATION: n is a, c, g, or t

<400> SEQUENCE: 29
agcatgtcaa gatcacagat tttgggctgg ccaan                              35

<210> SEQ ID NO 30
<211> LENGTH: 35
<212> TYPE: DNA
<213> ORGANISM: HOMO SAPIENS

<400> SEQUENCE: 30
agcatgtcaa gatcacagat tttgggctgg ccaaa                              35

<210> SEQ ID NO 31
<211> LENGTH: 35
<212> TYPE: DNA
<213> ORGANISM: HOMO SAPIENS
<220> FEATURE:
<221> NAME/KEY: misc_feature
<222> LOCATION: (34)..(35)
<223> OTHER INFORMATION: n is a, c, g, or t

<400> SEQUENCE: 31
catgtcaaga tcacagattt tgggctggcc aaann                              35

<210> SEQ ID NO 32
<211> LENGTH: 35
<212> TYPE: DNA
<213> ORGANISM: HOMO SAPIENS

<400> SEQUENCE: 32
gcatgtcaag atcacagatt tgggctggc caaac                               35

<210> SEQ ID NO 33
<211> LENGTH: 35
<212> TYPE: DNA
<213> ORGANISM: HOMO SAPIENS

<400> SEQUENCE: 33
catgtcaaga tcacagattt tgggctggcc aaact                              35

<210> SEQ ID NO 34
<211> LENGTH: 35
<212> TYPE: DNA
```

```
<213> ORGANISM: HOMO SAPIENS

<400> SEQUENCE: 34
atgtcaagat cacagatttt gggctggcca aactg                           35

<210> SEQ ID NO 35
<211> LENGTH: 35
<212> TYPE: DNA
<213> ORGANISM: HOMO SAPIENS

<400> SEQUENCE: 35
atgtcaagat cacagattttt ggctggccaa actgc                          35

<210> SEQ ID NO 36
<211> LENGTH: 35
<212> TYPE: DNA
<213> ORGANISM: HOMO SAPIENS

<400> SEQUENCE: 36
atgtcaagtc acagattttg gctggccaa actgc                            35

<210> SEQ ID NO 37
<211> LENGTH: 35
<212> TYPE: DNA
<213> ORGANISM: HOMO SAPIENS

<400> SEQUENCE: 37
tgtcaagatc acagattttg ggctggccaa actgc                           35

<210> SEQ ID NO 38
<211> LENGTH: 35
<212> TYPE: DNA
<213> ORGANISM: HOMO SAPIENS
<220> FEATURE:
<221> NAME/KEY: misc_feature
<222> LOCATION: (1)..(1)
<223> OTHER INFORMATION: n is a, c, g, or t

<400> SEQUENCE: 38
ngtcaagatc acagattttg ggctggccaa actgc                           35

<210> SEQ ID NO 39
<211> LENGTH: 35
<212> TYPE: DNA
<213> ORGANISM: HOMO SAPIENS
<220> FEATURE:
<221> NAME/KEY: misc_feature
<222> LOCATION: (1)..(3)
<223> OTHER INFORMATION: n is a, c, g, or t

<400> SEQUENCE: 39
nnncaagatc acagattttg ggctggccaa actgc                           35

<210> SEQ ID NO 40
<211> LENGTH: 35
<212> TYPE: DNA
<213> ORGANISM: HOMO SAPIENS

<400> SEQUENCE: 40
tgtcagatca cagattttgg gctggccaaa ctgct                           35

<210> SEQ ID NO 41
<211> LENGTH: 35
<212> TYPE: DNA
<213> ORGANISM: HOMO SAPIENS
```

<400> SEQUENCE: 41
gtcaagatca cagattttgg gctggccaaa ctgct                                35

<210> SEQ ID NO 42
<211> LENGTH: 35
<212> TYPE: DNA
<213> ORGANISM: HOMO SAPIENS
<220> FEATURE:
<221> NAME/KEY: misc_feature
<222> LOCATION: (1)..(1)
<223> OTHER INFORMATION: n is a, c, g, or t

<400> SEQUENCE: 42
ncaagatcac agattttggg ctggccaaac tgctg                                35

<210> SEQ ID NO 43
<211> LENGTH: 35
<212> TYPE: DNA
<213> ORGANISM: HOMO SAPIENS

<400> SEQUENCE: 43
tcaagatcac agattttggc tggccaaact gctgg                                35

<210> SEQ ID NO 44
<211> LENGTH: 177
<212> TYPE: DNA
<213> ORGANISM: HOMO SAPIENS

<400> SEQUENCE: 44
ttattataag gcctgctgaa aatgactgaa tataaacttg tggtagttgg agctggtggc     60
gtaggcaaga gtgccttgac gatacagcta attcagaatc attttgtgga cgaatatgat   120
ccaacaatag aggtaaatct tgttttaata tgcatattac tggtgcagga ccattct      177

<210> SEQ ID NO 45
<211> LENGTH: 31
<212> TYPE: DNA
<213> ORGANISM: HOMO SAPIENS

<400> SEQUENCE: 45
acgggctcgt tggatgctag ctgatcgcga a                                    31

<210> SEQ ID NO 46
<211> LENGTH: 30
<212> TYPE: DNA
<213> ORGANISM: HOMO SAPIENS

<400> SEQUENCE: 46
cggctcgctg gatgctagct gatcgcgaat                                      30

<210> SEQ ID NO 47
<211> LENGTH: 30
<212> TYPE: DNA
<213> ORGANISM: HOMO SAPIENS

<400> SEQUENCE: 47
ggctcgctgg atgctggctg atcgcgaatg                                      30

<210> SEQ ID NO 48
<211> LENGTH: 30
<212> TYPE: DNA
<213> ORGANISM: HOMO SAPIENS

```
<400> SEQUENCE: 48
gcacgctgga tgctagctga tcgcgaatgc                                    30

<210> SEQ ID NO 49
<211> LENGTH: 30
<212> TYPE: DNA
<213> ORGANISM: HOMO SAPIENS

<400> SEQUENCE: 49
ctcgctggat gctagctgat cgagaatgca                                    30

<210> SEQ ID NO 50
<211> LENGTH: 34
<212> TYPE: DNA
<213> ORGANISM: HOMO SAPIENS

<400> SEQUENCE: 50
acggctcgct ggatgctagc tgatcgcgaa tgca                               34
```